(12) United States Patent
Fuertinger et al.

(10) Patent No.: US 11,295,866 B2
(45) Date of Patent: Apr. 5, 2022

(54) SYSTEM AND METHOD OF CONDUCTING IN SILICO CLINICAL TRIALS

(71) Applicant: Fresenius Medical Care Holdings, Inc., Waltham, MA (US)

(72) Inventors: Doris Fuertinger, Graz (AT); Franz Kappel, Graz (AT); Peter Kotanko, New York, NY (US); Stephan Thijssen, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1100 days.

(21) Appl. No.: 14/974,861

(22) Filed: Dec. 18, 2015

(65) Prior Publication Data
US 2016/0180053 A1 Jun. 23, 2016

Related U.S. Application Data

(60) Provisional application No. 62/093,977, filed on Dec. 18, 2014.

(51) Int. Cl.
*G16H 50/50* (2018.01)

(52) U.S. Cl.
CPC .................................. *G16H 50/50* (2018.01)

(58) Field of Classification Search
CPC ............................. G16H 10/60; G16H 50/50
See application file for complete search history.

(56) References Cited

U.S. PATENT DOCUMENTS

| 2002/0095258 A1* | 7/2002 | Agur | G16H 20/10 |
| | | | 702/19 |
| 2004/0115647 A1 | 6/2004 | Paterson et al. | |
| 2005/0131663 A1* | 6/2005 | Bangs | G06F 19/00 |
| | | | 703/11 |
| 2006/0272652 A1* | 12/2006 | Stocker | G16H 50/50 |
| | | | 128/898 |

(Continued)

FOREIGN PATENT DOCUMENTS

| WO | 03054725 A2 | 7/2003 |
| WO | 2007022020 A2 | 2/2007 |
| WO | 2013036836 A2 | 3/2014 |

OTHER PUBLICATIONS

Fuertinger, Doris H., A model of erythropoiesis in adults with sufficient iron availability, J. Math. Biol. (2013) 66: 1209-1240 (Year: 2013).*

(Continued)

*Primary Examiner* — John P Go
(74) *Attorney, Agent, or Firm* — Nelson Mullins Riley & Scarborough LLP; Reza Mollaaghababa; Andrew W. Schultz

(57) ABSTRACT

Described herein are computer systems and methods for generating, in silico, one or more virtual patients. The one or more virtual patients can be used, for example, to conduct a virtual clinical trial, such as to determine an efficacy of a therapy or medical device. The one or more virtual patients mathematically represent a physiological system in an actual patient for a health condition. Also, the one or more virtual patients can be used, for example, to determine an adverse effect from a therapy or any other deviation from a therapy, or compliance of a patient suffering from a health condition on a therapeutic protocol.

43 Claims, 24 Drawing Sheets

(56) References Cited

U.S. PATENT DOCUMENTS

| | | | |
|---|---|---|---|
| 2007/0026365 A1* | 2/2007 | Friedrich | G06F 19/324 |
| | | | 434/127 |
| 2007/0038475 A1* | 2/2007 | Schlessinger | G16H 10/20 |
| | | | 705/2 |
| 2007/0148625 A1* | 6/2007 | Biltz | G09B 23/28 |
| | | | 434/262 |
| 2008/0256006 A1 | 10/2008 | Buscema et al. | |
| 2013/0052136 A1* | 2/2013 | Chamney | G01N 33/726 |
| | | | 424/9.2 |
| 2013/0085772 A1* | 4/2013 | Gaweda | G16H 50/20 |
| | | | 705/2 |
| 2014/0128791 A1* | 5/2014 | Fuertinger | G16H 20/17 |
| | | | 604/6.11 |
| 2014/0200181 A1* | 7/2014 | Fuertinger | G16H 50/20 |
| | | | 514/7.7 |

OTHER PUBLICATIONS

International Search Report and Written Opinion for corresponding PCT Application PCT/US2015/066793, dated Feb. 26, 2016; date of completion Feb. 16, 2016.
Albert, Blood Volume measurement, In: Nuclear Medicine In Vitro. 2 ed. Philadelphia: JB Lippincott Co., 1983.
Alfrey et al., Implications of neocytolysis for optimal management of anemia in chronic kidney disease Nephron Clin Pract. 2007; 106 (4): 149-156.
Barosi et al., Classification of anaemia on the basis of ferrokinetic parameters. Br J Haematol. Oct. 1985;61(2):357-370.
Besarab et al., The effects of normal as compared with low hematocrit values in patients with cardiac disease who are receiving hemodialysis and epoetin. N Engl J Med. Aug. 27, 1998;339(9):584-590.
Bratosin et al. Programmed cell death in mature erythrocytes: a model for investigating death effector pathways operating in the absence of mitochondria. Cell Death Differ. Dec. 2001;8(12):1143-56.
Chang et al., Changes of red blood cell surface markers in a blood doping model of neocytolysis. J Investig Med. Jun. 2009;57(5):650-654.
Chan et al., Regulation of transferrin receptor mRNA expression Distinct regulatory features in erythroid cells. Eur J Biochem. Mar. 15, 1994;220(3):683-92.
Crepaldi et al. Iron management in hemodialysis patients: optimizing outcomes in Vicenza, Italy. Hemodial Int. Jun. 1, 2003;7(3):216-21.
Drueke et al., Normalization of hemoglobin level inpatients with chronic kidney disease and anemia. N Engl J Med. Nov. 16, 2006;355(20):2071-2084.
Finch et al., Iron metabolism; hematopoiesis following phlebotomy; iron as a limiting factor. J Clin Invest Aug. 1950;29(8): 1078-86.
Finch et al., The Journal of American Society of Hematology, 60(6): 1241-1246, 1982.
Fishbane et al., Hemoglobin cycling in hemodialysis patients treated with recombinant human erythropoietin. Kidney Int. Sep. 2005;68(3): 1337-43.
Fisher, Experimental Biology and Medicine, 28: 1-24, 2003.
Fleming et al., The regulation of hepcidin and its effects on systemic and cellular iron metabolism. Hematology Am Soc Hematol Educ Program. 2008:151-158.
Foller et al., Enhanced susceptibility to suicidal death of erythrocytes from transgenic mice overexpressing erythropoietin. Am J Physiol Regul Integr Comp Physiol Sep. 2007;293(3):R1127-1134.
Foller et al., Erythrocyte programmed cell death. IUBMB Life. Oct. 2008;60(10):661-8.
Fuertinger et al., A model of erythropoiesis in adults with sufficient iron availability. J Math Biol. May 2013;66(6): 1209-40.
Goodnough, Nephrology Dialysis Transplantation, 17:14-18, 2002.
Goodnough et al., Detection, evaluation, and management of iron-restricted erythropoiesis. Blood. Dec. 2, 2010; 116(23):4754-61.
Goodnough et al., Detection,evaluation, and management of pre-operative anaemia in the elective orthopaedic surgical patient: NATA guidelines. Br J Anaesth. Jan. 2011; 106(1): 13-22.
Greer et al., Wintrobe's Clinical Hematology, vol. 1. Lippincott Williams & Wilkins, 12th edition, 2009.
International Preliminary Report on Patentability received in PCT/US2015/066793 dated Jun. 29, 2017; 11 pages.
Jandl, Textbook of Hematology, 2nd Ed. Little, Brown and Company, 1996.
Kalantar-Zadeh et al., Time-dependent associations between iron and mortality in hemodialysis patients. J Am Soc Nephrol. Oct. 2005; 16(10):13070-3080.
Lang et al., Erythrocyte ion channels in regulation of apoptosis. Adv Exp Med Biol. 2004;559:211-217.
Lang et al., Mechanisms and significance of eryptosis. Antioxid Redox Signal. Jul.-Aug. 2006;8 (7-8): 1183-1192.
Lang et al., Eryptosis, a window to systemic disease. Cell Physiol Biochem. 2008;22(5-6):373-380.
Lichtman et al., Williams Hematology, 7th edition, New York, McGraw-Hill, 2005.
Loria et al., Red cell life span in iron deficiency anaemia. Br J Haematol. May 1967;13(3):294-302.
Myssina et al., Inhibition of erythrocyte cation channels by erythropoietin. J Am Soc Nephrol. Nov. 2003;14(11):2750-2757.
Parfrey, Target hemoglobin level for EPO therapy in CKD. Am J Kidney Dis. Jan. 2006;47(1):171-173.
Pfeffer et al., A trial of darbepoetin alfa in type 2 diabetes and chronic kidney disease. N Engl J Med. Nov. 19, 2009;361(21):2019-32.
Polenakovic et al., Is erythropoietin a survival factor for red blood cells? J Am Soc Nephrol. Aug. 1996;7(8): 1178-82.
Ponka, Tissue-specific regulation of iron metabolism and heme synthesis: distinct control mechanisms in erythroid cells. Blood. Jan. 1, 1997;89(1):1-25.
Ponka et al., The transferrin receptor: role in health and disease. Int J Biochem Cell Biol. Oct. 1999;31(10):1111-37.
Recommended methods for measurement of red-cell and plasma volume: International Committee for Standardization in Haematology. J Nucl Med. Aug. 1980;21(8):793-800.
Rice et al., The negative regulation of red cell mass by neocytolysis: physiologic and pathophysiologic manifestations. Cell Physiol Biochem. 2005;15(6):245-50.
Singh et al., Correction of anemia with epoetin alfa in chronic kidney disease. N Engl J Med. Nov. 16, 2006;355(20):2085-98.
Strippoli et al., Hemoglobin targets for the anemia of chronic kidney disease: a meta-analysis of randomized, controlled trials. J Am Soc Nephrol. Dec. 2004;15(12):3154 65.
Wish, Assessing iron status: beyond serum ferritin and transferrin saturation. Clin J Am Soc Nephrol. Sep. 2006;1 Suppl 1:S4-8.
Wu et al., Generation of committed erythroid BFU-E and CFU-E progenitors does not require erythropoietin or the erythropoietin receptor. Cell. Oct. 6, 1995;83(1):59-67.
D. H. Fuertinger. A model for erythropoiesis. PhD thesis, University of Graz, Austria, 2012 (167 pages).
Extended European Search Report dated Sep. 12, 2018 for Application No. 15871203.4; pp. 1-8.

* cited by examiner

FIG. 4A

| | A | B | C | D | E | F | G | H | I | J |
|---|---|---|---|---|---|---|---|---|---|---|
| 1 | Patient | sex | race | age | diabetic | weight | height | TBV | S0 | aw1 a |
| 2 | 100001 | F | B | 52 | 1 | 69.4 | 163 | 4000 | 0.0664 | 0.8 |
| 3 | 100002 | M | B | 53 | 0 | 73.15 | 178 | 5000 | 0.083 | 0.9 |
| 4 | 100003 | M | B | 66 | 0 | 53.98 | 170 | 4150 | 0.06889 | 0.95 |
| 5 | 100004 | M | B | 64 | 1 | 95.95 | 165 | 5350 | 0.08881 | 1.5 |
| 6 | 100005 | F | B | 78 | 1 | 57.81 | 163 | 3650 | 0.06059 | 0.8 |
| 7 | 100006 | M | B | 56 | 0 | 64.06 | 168 | 4400 | 0.07304 | 0.85 |
| 8 | 100007 | F | B | 80 | 1 | 81.94 | 163 | 4450 | 0.07387 | 1.05 |
| 9 | 100008 | F | NHW | 73 | 0 | 45.82 | 158 | 3115 | 0.0581 | 0.95 |
| 10 | 100009 | F | B | 76 | 1 | 55.39 | 169 | 3750 | 0.06225 | 0.95 |
| 11 | 100010 | F | B | 61 | 0 | 87.47 | 171 | 4850 | 0.08051 | 1.1 |
| 12 | 100011 | M | B | 48 | 0 | 71.21 | 172 | 4800 | 0.07965 | 0.8 |
| 13 | 100012 | F | B | 42 | 0 | 76.94 | 161 | 4200 | 0.06972 | 0.8 |
| 14 | 100013 | M | B | 62 | 1 | 81.95 | 175 | 5300 | 0.08798 | 1.2 |
| 15 | 100014 | F | W | 47 | 0 | 99.4 | 172 | 5300 | 0.08798 | 1.25 |
| 16 | 100015 | F | B | 73 | 1 | 84.3 | 174 | 4850 | 0.08051 | 1.05 |
| 17 | 100016 | M | B | 62 | 1 | 78.67 | 169 | 4900 | 0.08134 | 1 |
| 18 | 100017 | F | W | 72 | 0 | 72.84 | 163 | 4500 | 0.0747 | 1.2 |
| 19 | 100018 | F | B | 62 | 1 | 86.15 | 175 | 5050 | 0.08383 | 1 |
| 20 | 100019 | M | B | 50 | 0 | 61.92 | 174 | 4550 | 0.083 | 1.2 |
| 21 | 100020 | M | B | 73 | 0 | 67.77 | 174 | 5000 | 0.083 | 1 |
| 22 | 100021 | F | NHW | 47 | 1 | 53.6 | 173 | 3800 | 0.07055 | 0.8 |
| 23 | 100022 | M | W | 70 | 0 | 101 | 175 | 5800 | 0.09628 | 1 |
| 24 | 100023 | F | Whisp | 25 | 0 | 41.11 | 144 | 2600 | 0.04316 | 0.52 |
| 25 | 100024 | F | B | 80 | 1 | 101.61 | 167 | 5300 | 0.08798 | 1 |
| 26 | 100025 | M | B | 80 | 1 | 99.2 | 185 | 6120 | 0.101592 | 0.7 |
| 27 | 100026 | F | Whisp | 40 | 1 | 57.42 | 165 | 3680 | 0.061088 | 1 |
| 28 | 100027 | M | Whisp | 66 | 1 | 81.15 | 170 | 5020 | 0.083332 | 1.2 |
| 29 | 100028 | F | B | 47 | 1 | 135.56 | 164 | 6240 | 0.103584 | 0.8 |
| 30 | 100029 | M | Whisp | 25 | 0 | 53.89 | 156 | 3730 | 0.061918 | 0.8 |
| 31 | 100030 | M | W | 26 | 1 | 56.28 | 159 | 3890 | 0.064574 | 0.95 |
| 32 | 100031 | F | B | 58 | 1 | 68.06 | 170 | 4600 | 0.07636 | 1 |
| 33 | 100032 | M | B | 75 | 1 | 69.27 | 166 | 4100 | 0.06806 | 1 |
| 34 | 100033 | M | B | 59 | 1 | 74.17 | 175 | 4960 | 0.082336 | 1 |
| 35 | 100034 | F | W | 58 | 1 | 93.78 | 168 | 4970 | 0.082502 | 0.9 |
| 36 | 100035 | F | W | 62 | 1 | 75.46 | 163 | 4220 | 0.070052 | 0.9 |
| 37 | 100036 | F | B | 85 | 1 | 46.1 | 162 | 3220 | 0.053452 | 0.6 |

| aw2 | aw3 | aw4 | aw5 | RBCLifespan | HaHlife (h) | end_Epo | k_ac | k_vt | TBVincrease |
|---|---|---|---|---|---|---|---|---|---|
| 0.8 | 0.8 | 0.8 | 0.8 | 69.1982195 | 4.37117168 | 167.7750708 | 0.006788383 | 0.18668809 | 382.09 |
| 0.9 | 0.9 | 0.9 | 0.9 | 76.9818062 | 9.34351983 | 180.954594 | 0.005959809 | 0.169908533 | 439.43 |
| 0.95 | 0.95 | 0.95 | 0.9 | 81.12728018 | 4.41516092 | 99.98926199 | 0.007785942 | 0.21 | 344.92 |
| 0.95 | 0.95 | 0.95 | 0.71 | 81.1277218 | 4.41516092 | 99.98926199 | 0.007785942 | 0.21 | 344.92 |
| 1.5 | 1.2 | 1.2 | 1.23 | 69.2111845 | 8.64237175 | 22.32843007 | 0.009469928 | 0.288137 | 603.13 |
| 0.8 | 0.8 | 0.8 | 0.77 | 72.3897306 | 10.5 | 89.20439832 | 0.010257891 | 0.22449929 | 275.66 |
| 0.8 | 0.8 | 0.8 | 0.87 | 82.9258734 | 10.5 | 89.20439832 | 0.01 | 0.02 | 376.01 |
| 1.1 | 1.1 | 1.1 | 0.83 | 84.73230397 | 7.591020181 | 92.9258734 | 0.007956035 | 0.1785474 | 293.46 |
| 0.95 | 0.95 | 1.05 | 0.7 | 64.20767400 | 12.3279 | 162.367545 | 0.007956035 | 0.03660774 | 544.32 |
| 0.75 | 0.75 | 0.75 | 0.8 | 71.369256 | 12.3279 | 162.367545 | 0.0106 | 0.02 | 297.56 |
| 0.9 | 0.9 | 0.9 | 0.93 | 69.25772272 | 9.9542802 | 77.98439272 | 0.005909614 | 0.481000324 | 513.98 |
| 1.6 | 1.6 | 1.6 | 0.85 | 68 | 9.9542802 | 77.98439272 | 0.0106 | 0.2 | 320.51 |
| 1.75 | 1.75 | 1.75 | 1.05 | 71.647374274 | 4.114747474 | 153.4875115 | 0.00738279 | 0.00793 | 529.31 |
| 1.55 | 1.55 | 1.55 | 0.97 | 85.20648314 | 6.2824316 | 44.22044943 | 0.01108 | 0.02 | 698.32 |
| 0.9 | 0.9 | 0.9 | 1.2 | 93.20948703 | 9.392802 | 107.0046626 | 0.01108 | 0.02 | 544.32 |
| 1.4 | 1.4 | 1.4 | 1 | 91.29164511 | 5.5 | 97.0685525 | 0.006353334 | 0.059582599 | 701.52 |
| 1.2 | 1.2 | 1.2 | 1.15 | 71.057068464 | 5.11560552 | 135 | 0.01021937 | 0.0801364 | 416.19 |
| 1 | 1 | 1 | 1.18 | 85.84481712 | 4.40619817 | 77.61200414 | 0.01 | 0.027 | 256.43 |
| 0.52 | 0.52 | 0.52 | 0.65 | 70 | 4.9 | 156.85061 | 0.0071995 | 0.007 | 263 |
| 1 | 1 | 1 | 1.1 | 55.57459709 | 5.5 | 155.1875009 | 0.01 | 0.01 | 247.13 |
| 0.6 | 0.6 | 0.6 | 0.95 | 60.9030378 | 4.82936539 | 78.70099732 | 0.006 | 0.02937023 | 544.3 |
| 0.8 | 0.8 | 0.8 | 0.8 | 67.8489712 | 9.56783 | 85.33200007 | 0.00811963 | 0.0065721 | 544.3 |
| 1.3 | 1.3 | 1.3 | 0.75 | 50.5 | 8.5 | 66.776 | 0.009 | 0.2 | 718.99 |
| 1 | 1 | 1 | 1.27 | 60.5 | 9 | 155.1875009 | 0.009 | 0.007 | 441.24 |
| 1.25 | 1.25 | 1.29 | 0.95 | 70.12964 | 6.270238 | 151.907819 | 0.005071 | 0.007793 | 302.28 |
| 1.1 | 1.1 | 1.1 | 0.77 | 70.307991 | 7.9923824 | 115.244715 | 0.007793 | 0.381479 | 434.6 |
| 1.4 | 1.4 | 1.4 | 0.95 | 54.139057 | 6.348749 | 192.49707 | 0.010796 | 0.004403 | 297.52 |
| 1.8 | 1.8 | 1.8 | 1.02 | 67.302215 | 6.941148 | 122.4875326 | 0.009152 | 0.001782 | 504.82 |
| 0.9 | 0.9 | 0.9 | 0.9 | 85.027637 | 10.678875 | 67 | 0.01227 | 0.065009 | 322.8 |
| 0.5 | 0.5 | 0.5 | 0.8 | 71.991278 | 11.965223 | 153.8902706 | 0.007563 | 0.015359 | 511.97 |
| 0.5 | 0.5 | 0.5 | 0.802 | 65.864603 | 4.574863 | 193.047723 | 0.005991 | 0.015359 | 183.52 |

| | Model – Equations (Dynamical System) |
|---|---|
| BFU-E | $\frac{\partial}{\partial t}p(t,x^p) + \frac{\partial}{\partial x^p}p(t,x^p) = \beta^p p(t,x^p),$ |
| CFU-E | $\frac{\partial}{\partial t}q(t,x^q) + \frac{\partial}{\partial x^q}q(t,x^q) = (\beta^q - \alpha^q(E(t)))q(t,x^q),$ |
| Erythoblasts | $\frac{\partial}{\partial t}r(t,x^r) + \frac{\partial}{\partial x^r}r(t,x^r) = \beta^r r(t,x^r),$ |
| BM Reticulocytes | $\frac{\partial}{\partial t}s(t,x^s) + v^s(E(t))\frac{\partial}{\partial x^s}s(t,x^s) = -\alpha^s s(t,x^s),$ |
| Erythrocytes | $\frac{\partial}{\partial t}m(t,x^m) + \frac{\partial}{\partial x^m}m(t,x^m) = -\alpha^m(E(t),x^m)m(t,x^m),$ |
| endogenous Epo | $\frac{d}{dt}E^{end}(t) = \frac{1}{TBV}E^{end}_{in}(t) - c^{end}_{deg}E^{end}(t),$ |
| exogenous Epo | $\frac{d}{dt}E^{ex}(t) = \frac{1}{TBV}E^{ex}_{in}(t) - c^{ex}_{deg}E^{ex}(t),$ |

FIG. 12

| | VDC (N=60) |
|---|---|
| | Mean ± STD (Min, Max) |
| Age | 59.42 ± 14.70 (25.23, 85.72) |
| IDWG | 2.56 ± 0.88 (0.38, 5.19) |
| Weight | 78.64 ± 19.67 (41.75, 136.11) |
| Albumin | 4.01 ± 0.28 (3.32, 4.53) |
| EPO Dose | 17.94 ± 17.66 (0.00, 98.46) |
| Ferritin | 1006 ± 544 (87, 3323) |
| EKTV | 1.49 ± 0.20 (1.08, 2.15) |
| TSAT | 34.80 ± 8.84 (17.80, 56.60) |
| NLR | 3.59 ± 2.01 (1.03, 10.41) |
| Height | 166.50 ± 9.69 (131.00, 187.00) |
| Vintage | 3.63 ± 3.30 (0.00, 14.47) |
| | Percentage (%) |
| Race | 48.33 |
| Male | 51.67 |
| Diabetic | 58.33 |
| Access Catheter | 8.33 |

SYSTEM AND METHOD OF CONDUCTING IN SILICO CLINICAL TRIALS

RELATED APPLICATION

The present application claims priority to provisional application No. 62/093,977, entitled "System And Method Of Conducting In Silico Clinical Trials," filed on Dec. 18, 2014. This application incorporates the content of the provisional application by reference in its entirety.

BACKGROUND OF THE INVENTION

Clinical trials are conducted to collect data and other information regarding the safety and efficacy of drugs and medical devices. There are several steps and stages of approval in the clinical trials process before a drug or device can be sold in the consumer market. These steps typically require millions of dollars of investment and take years to complete.

Drug and device testing begins with extensive laboratory research which can involve years of experiments in animals and human cells. If the initial laboratory research is successful, the Food and Drug Administration (FDA) can approve to continue research and testing in humans. Once approved, human testing of drugs and medical devices can begin and is typically conducted in four phases. Each phase is considered a separate trial and, after completion of a phase, investigators are required to submit their data for approval from the FDA before continuing to the next phase.

A Phase I clinical trial assesses the safety of a drug or device in healthy volunteers. This initial phase of testing, which can take several months to complete, usually includes a small number of healthy volunteers (20 to 100). The study is designed to determine the effects of the drug or device on humans including how it is absorbed, metabolized, and excreted. This phase also investigates the side effects that occur as dosage levels are increased.

A Phase II clinical trial tests the efficacy of a drug or medical device. This second phase of testing can last from several months to a couple of years, and typically involves up to several hundred patients. Most phase II studies are randomized trials where one group of patients receives the new drug, while a second "control" group receives a standard treatment or placebo. Often these studies are "blinded," meaning that neither the patients nor the researchers know who has received the drug. This allows investigators to provide the pharmaceutical company and the FDA with comparative information about the relative safety and effectiveness of the new drug.

A Phase III clinical trial involves randomized and blind testing in several hundred to several thousand patients. This large-scale testing, which can last several years, provides a more thorough understanding of the effectiveness of the drug or device as well as the range of possible adverse reactions. Once Phase III is complete, a pharmaceutical company can request FDA approval for marketing the drug.

Finally, a Phase IV clinical trial, often called Post Marketing Surveillance Trial, can be conducted after a drug or device has been approved for consumer sale. Objectives at this stage are: (1) to compare a drug with other drugs already in the market; (2) to monitor a drug's long-term effectiveness and impact on a patient's quality of life; and (3) to determine the cost-effectiveness of a drug therapy relative to other traditional and new therapies. Phase IV studies can result in a drug or device being taken off the market or restrictions of use being placed on the product depending on the findings in the study.

Conducting all phases of a clinical trial to test a new drug or medical device presents many challenges to investigators. Some challenges include the time and financial demands of clinical trials, the complexity of FDA regulations, inadequate research training among many clinicians, pressures to which both investigators and volunteers are subjected during the course of a trial, and data collection challenges (e.g., medical records, quality control).

Therefore, there is a need for reliable, cost-effective predictive models for performing a clinical trial, in silico, to supplement and/or replace actual clinical trials.

SUMMARY OF THE INVENTION

Described herein are methods and computer systems for generating, in silico, one or more virtual patients. The one or more virtual patients can be used, for example, to conduct a virtual clinical trial, e.g., to determine safety and efficacy of a therapy. The virtual patients can mathematically represent one or more physiological systems in an actual patient. As discussed in more detail below, the virtual patients can be used, for example, to assess the effect of a therapy, to optimize a therapy for administration to actual patients, and to reject a therapy based on observed adverse effects on virtual patients, etc.

In one aspect, the present invention relates to a method for determining efficacy of a therapy. The method comprises generating in silico a plurality of virtual patients for modeling a health condition based on data collected from a population of previously treated patients. The collected data represents at least one measured biological response of the previously treated patients to a previously administered therapeutic regimen. The method further comprises applying a simulated therapy to the virtual patients and determining one or more physiological parameters in the virtual patients in response to the simulated therapy.

The above method for determining efficacy of a therapy can further comprise adjusting the simulated therapy based on the determined one or more physiological parameters of the virtual patients, applying the adjusted simulated therapy to the virtual patients, and determining one or more physiological parameters in response to the adjusted simulated therapy.

In some embodiments, the method further comprises repeating the adjusting, applying, and determining steps so as to optimize the simulated therapy for application to one or more actual patients.

In a related aspect, the invention relates to a method for performing a clinical trial in silico. The method comprises generating in silico one or more virtual patients, wherein the one or more virtual patients are generated based on data collected from a population of previously treated patients suffering from a health condition. The method further comprises applying a simulated therapy to each of the one or more virtual patients and determining one or more physiological parameters in the virtual patients in response to the simulated therapy.

In some embodiments, the simulated therapy includes a simulated non-compliance with a prescribed therapy.

In one embodiment, the above method for performing a clinical trial can further comprise the following iterative steps to derive an optimal therapy for the health condition: modifying one or more parameters of the simulated therapy, thereby creating a modified simulated therapy, administering the modified simulated therapy to each of the virtual patients, and determining one or more physiological parameters in the virtual patients in response to the modified simulated therapy.

In one aspect, the invention relates to a computer system for determining efficacy of a therapy. The computer system comprises a generation module to generate in silico a plurality of virtual patients for modeling a health condition based on data collected from a population of previously treated patients suffering from the health condition, where the collected data represents at least one measured biological response of the previously treated patients to a previously administered therapeutic regimen, and a simulation module to apply a simulated therapy to the virtual patients and to determine one or more physiological parameters of the virtual patients in response to the simulated therapy.

In one embodiment of the computer system, the simulation module is further configured to adjust the simulated therapy based on the one or more physiological parameters thereby creating a modified simulated therapy. The simulation module applies the modified simulated therapy to the virtual patients, and determines one or more physiological parameters of the virtual patients in response to the applied modified simulated therapy.

In one aspect, the invention relates to a method of generating a virtual patient. The method comprises generating in silico at least one mathematical model representing one or more physiological systems. The model can include one or more adjustable parameters for each of the one or more physiological systems. To generate a virtual patient corresponding to an actual patient, the values of the adjustable parameters can be determined based on physiological data, including a response of that actual patient to administration of a therapeutic regimen.

In one aspect, the invention relates to a method for assessing modifications to a therapy. The method comprises generating in silico a plurality of virtual patients based on data collected from a population of previously treated patients; utilizing the virtual patients to devise a simulated therapy, determining one or more physiological parameters of the virtual patients in response to application of the simulated therapy to the virtual patients, modifying one or more parameters of the simulated therapy and determining one or more physiological parameters of the virtual patients in response to application of the modified simulated therapy to the virtual patients, and identifying one or more patients, if any, that respond adversely to the modified simulated therapy based on the determined physiological parameters.

In one aspect, the invention relates to a method of determining compliance of a patient suffering from a health condition with a therapeutic protocol. The method comprises generating in silico a virtual patient representing the actual patient. A simulated therapeutic protocol can be applied to the virtual patient, and one or more physiological parameters of the virtual patient can be determined in response to the simulated therapeutic protocol. Further, one or more respective physiological parameters of the respective actual patient can be measured and compared with the physiological parameters determined in the virtual patient to assess the actual patient's compliance with the therapeutic protocol.

In some embodiments, the data collected from the population of previously treated patients comprises gender, age, weight, height, ethnicity, metabolic/chemistry, complete blood count, or a combination thereof. In some embodiments, the data collected further comprises medications used by the previously treated patients, past medical history data, past surgical history data, or a combination thereof. In one embodiment, the past medical history data comprises information regarding diabetes, blood pressure/hypertension, cancer, congestive heart failure, kidney disease, or a combination thereof.

In some embodiments, the methods and computer systems described herein further comprise determining whether at least one of a plurality of determined physiological parameters of at least one of a plurality of virtual patients is indicative of an adverse effect from a simulated therapy.

In some embodiments, one or more physiological parameters in a plurality of virtual patients are determined in response to an applied therapy at a plurality of times over a predetermined time interval.

In some embodiments, the one or more physiological parameters comprises one or more metabolic parameters. The metabolic parameters can comprise, for example, blood parameters and/or urine parameters. By way of example, the blood parameters can comprise any of hemoglobin concentration and hematocrit level.

In some embodiments, each of the virtual patients comprises at least one in silico model representing a physiological system. By way of example, the model can be an erythropoiesis model, which can represent, at least in part, the physiological system responsible for production of red blood cells.

In some embodiments, the therapy comprises any of at least one pharmacological therapy, at least one non-pharmacological therapy, or a combination thereof. In one embodiment, the at least one pharmacological therapy comprises an anemia therapy. The anemia therapy can comprise administering at least one of an erythropoiesis stimulating agent (ESA), iron, or a combination thereof. In some embodiments, the erythropoiesis stimulating agent comprises exogenous erythropoietin. In one embodiment, the one or more non-pharmacological therapies comprises a fluid therapy, a dietary therapy, an exercise therapy, or a combination thereof.

BRIEF DESCRIPTION OF THE DRAWINGS

The foregoing will be apparent from the following more particular description of exemplary embodiments of the invention, as illustrated in the accompanying drawings in which like reference characters refer to the same parts throughout the different views. The drawings are not necessarily to scale, emphasis instead being placed upon illustrating embodiments of the present invention.

FIG. 4A illustrates data collected from a population of patients shown as a user interface on a computer system.

FIG. 4B is a table of data collected from patients in a target population.

In FIG. 5A, the dashed line represents the actual hemoglobin concentration of an actual patient and the solid line represents the simulated hemoglobin concentration for the patient.

FIG. 10 is a list of equations used to represent various aspects of the aforementioned anemia (erythropoiesis) model.

FIG. 12 is a table of data from virtual patients in a virtual dialysis clinic (VDC).

DETAILED DESCRIPTION OF THE INVENTION

Figure 1:
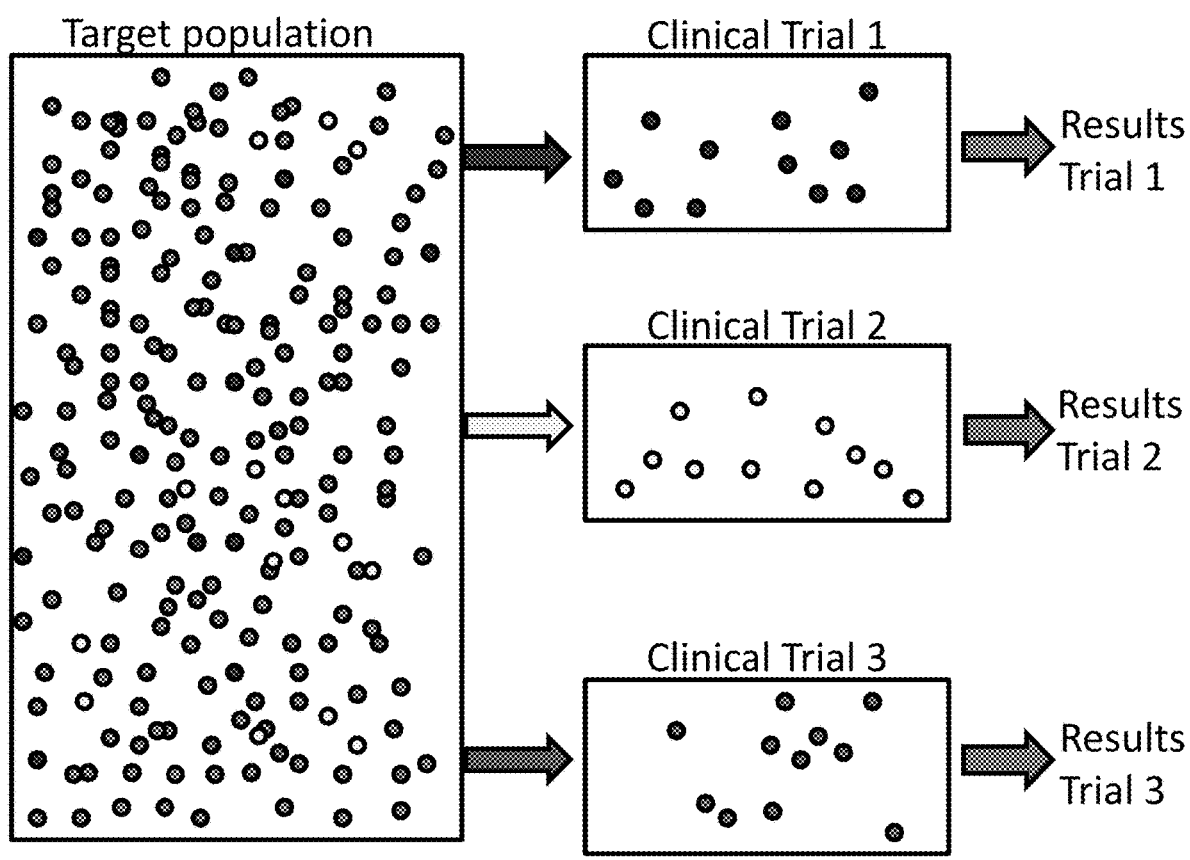
FIG. 1 illustrates patient selection for 3 clinical trials from a target population.

In one aspect, the present teachings relate generally to methods and systems for assessing therapies in silico using one or more virtual patients. As discussed in more detail below, each virtual patient can be a mathematical construct representing in silico one or more physiological systems of a respective actual patient. In this manner, a plurality of virtual patients can be constructed that mimic a plurality of actual patients. As discussed in more detail below, such virtual patients can be employed, for example, to optimize a therapy for administration to actual patients, reject a therapy based on observed adverse effect on one or more virtual patients, assess how modifications in a therapy can affect actual patients, etc. In some embodiments, a collection of virtual patients generated in accordance with the present teachings can be employed to conduct in silico clinical trials. Such in silico clinical trials can provide a number of advantages, such as inclusion of individuals (such as, pregnant women, infants) that are typically difficult to include in clinical trials, the possibility of modifying a therapy and obtaining information regarding modified therapy on a much shorter time scale than is possible in conventional clinical trials.

Certain exemplary embodiments will now be described to provide an overall understanding of the principles of the computer systems and methods disclosed herein. One or more examples of these embodiments are illustrated in the accompanying drawings. Those skilled in the art will understand that the computer systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

So that the invention may more readily be understood, certain terms are first defined.

As used herein, the terms "virtual patient," "avatar" and "virtual dummy" are used interchangeably and refer to a mathematical construct (model) that represents one or more physiological systems (or subsystems) of an actual patient. The term "actual patient" as used herein refers to a live or dead individual. As used herein, the terms "about" or "approximately" for any numerical values or ranges indicate a suitable dimensional tolerance that allows the composition, part, or collection of elements to function for its intended purpose as described herein. These terms indicate at most a ±5% variation about a central value.

As used herein, the terms "a" or "an" refers to one or more of this kind of entity; for example, "an adverse effect" should be understood as one or more adverse effects e.g., from a therapy (e.g., drug). Therefore, the terms "a," "an," "one or more" as well as "at least one" can be used interchangeably herein.

Virtual Dialysis Clinic (Virtual Clinical Trials)

Described herein is a Virtual Dialysis Clinic ("VDC") or a method and system for performing a virtual clinical trial, in silico, for a health condition. For example, the methods and systems described herein can provide a complementary approach to the current standards in clinical trials and health care practice (see FIG. 2A). In some cases, the methods and systems describe herein can replace conventional clinical trials. The VDC approach can bypass and/or address ethical, legal, and scientific challenges typically encountered in current approaches to clinical trials for determining novel therapies and diagnostics.

Clinical research regarding new therapeutics and/or diagnostics follow a generally well-defined pathway in the form of clinical trials (Phases 1, 2, 3 and 4). These trials take place in volunteers (phases 1-3), who are either healthy (phase 1) or come from the intended target population (phases 2 and 3). Each volunteer undergoes specific pre-test screening to assess their eligibility, using inclusion and exclusion criteria set by the study design. The most rigorous standard, a phase 3 trial, is a randomized, controlled trial (RCT). Randomization is applied to account for observed and unobserved baseline covariates. Further, there are clinical and statistical (e.g., power, confidence, etc.) considerations that inform sample size decisions (e.g., how many individuals need to be enrolled in a study to observe a positive or negative effect, how many total patients having a certain disease or condition should be enrolled in a clinical trial). The patient population in a phase 3 trial is, in most cases, a highly selective group. However, some of the major concerns with any clinical trial are the generalizability of the study findings to the intended target population, population size, safety (e.g. adverse effects), and costs.

FIG. 1 schematically illustrates three conventional clinical trials. The target population comprises all individuals (represented by the dots) that would be selected to enter one of the three clinical trials: clinical trial 1, clinical trial 2 or clinical trial 3. As shown schematically in the figure, each individual of the target population can participate in only one of the three clinical trials, thus limiting the number of individuals available for each trial. Further, it may not be possible to include certain individuals in the clinical trials, e.g., due to safety and/or ethical concerns. Moreover, each clinical trial can require many months, or even years, to complete, and can cost hundreds and even millions of dollars. As discussed further below, the teachings of the invention for performing clinical trials in silico address such and other shortcomings of conventional clinical trials.

Figure 2A:
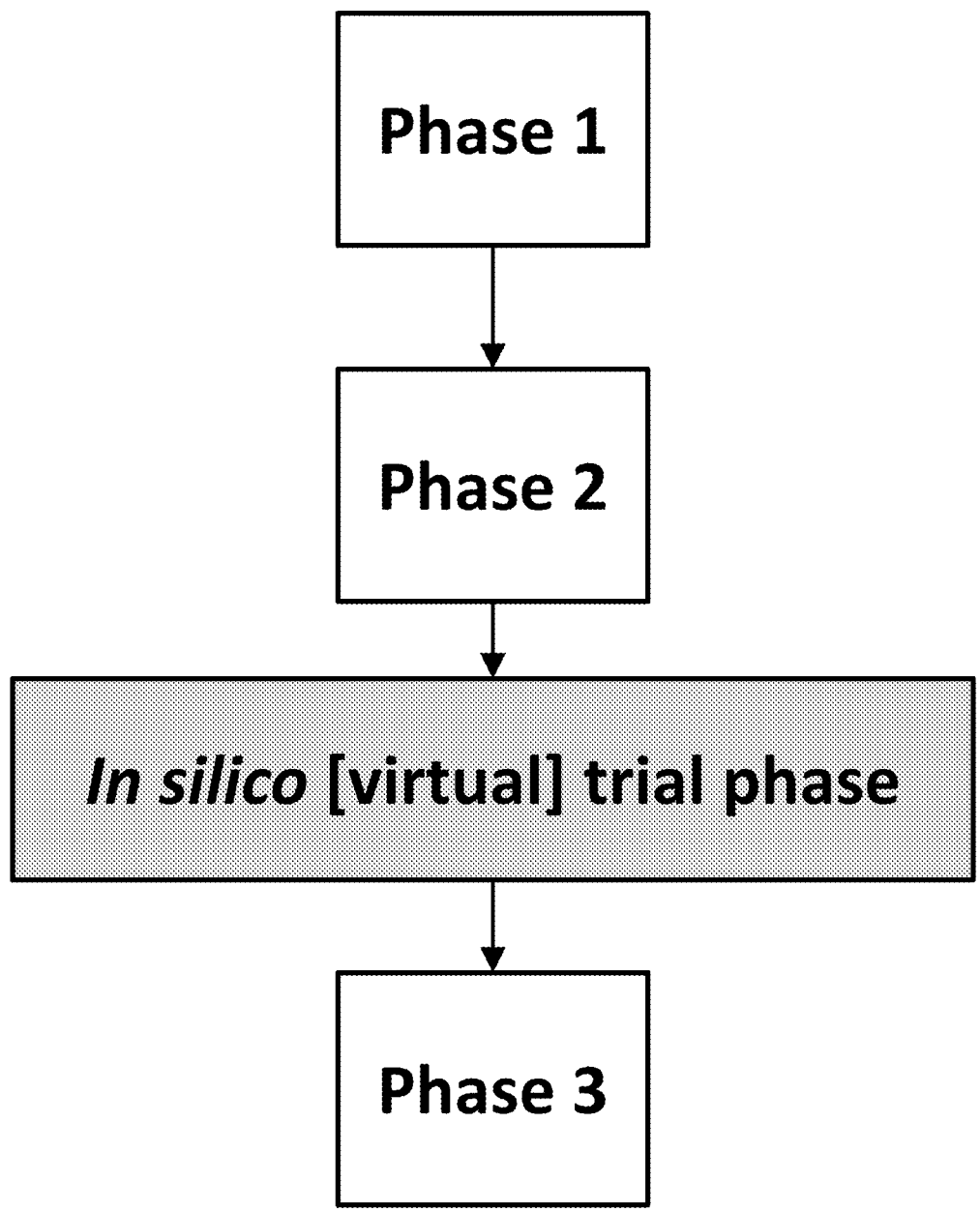
FIG. 2A is a flow diagram of an in silico trial used to supplement actual clinical trials.

FIG. 2A represents a flow diagram of a clinical trial that is supplemented with a virtual trial in accordance with one embodiment of the present teachings. In Phase 1, a therapeutic (e.g., drug) is tested for safety, dosage, and side effects in a small number of healthy volunteers. Phase 2 examines the drug's safety and effectiveness in a small number of volunteers (those having the disease or is in need of treatment).

Rather than moving after phase 2 to a conventional phase 3 trial, an in silico (virtual) trial (e.g., VDC) according to the present teachings can be performed, e.g. to inform the conduct of a subsequent phase of the clinical trial. Such a virtual trial can include, for example, extensive high-throughput testing for safety and effectiveness employing computer simulations in appropriate physiological models of existing patients. Based on information and data gathered from the virtual clinical trial, a phase 3 trial can be performed, optimized based on the results of the virtual trial. A phase 3 clinical trial looks at the effectiveness, side effects, and comparison with other treatments in a large number of volunteer patients.

A virtual trial, in silico, is run in an initial step similarly to a phase 1, 2 or 3 clinical trial (see, e.g., FIG. 3A) in that a question is typically defined to be addressed in the trial (e.g., How does better fluid management affect erythropoiesis stimulating agents (ESA) and iron utilization?; What is the effect of iron delivery in the dialysate on ESA utilization?; How does an anti-inflammatory intervention affect anemia control?). Next, mathematical models are designed and used to describe the physiology pertinent to the trial question at hand. A representative and/or random actual patient sample is drawn from a larger target population. As discussed in more detail below, mathematical techniques are employed to create patient specific virtual patients based on the actual patients in the drawn patient population. One or more test treatment options are applied, in silico, to the virtual patients. The responses of the virtual patients to the applied test treatment options can inform which option(s) can provide the most promising treatments for application to actual patient population. In some embodiments, the most promising treatment options can be selected for further clinical (actual) testing.

Figure 2B:
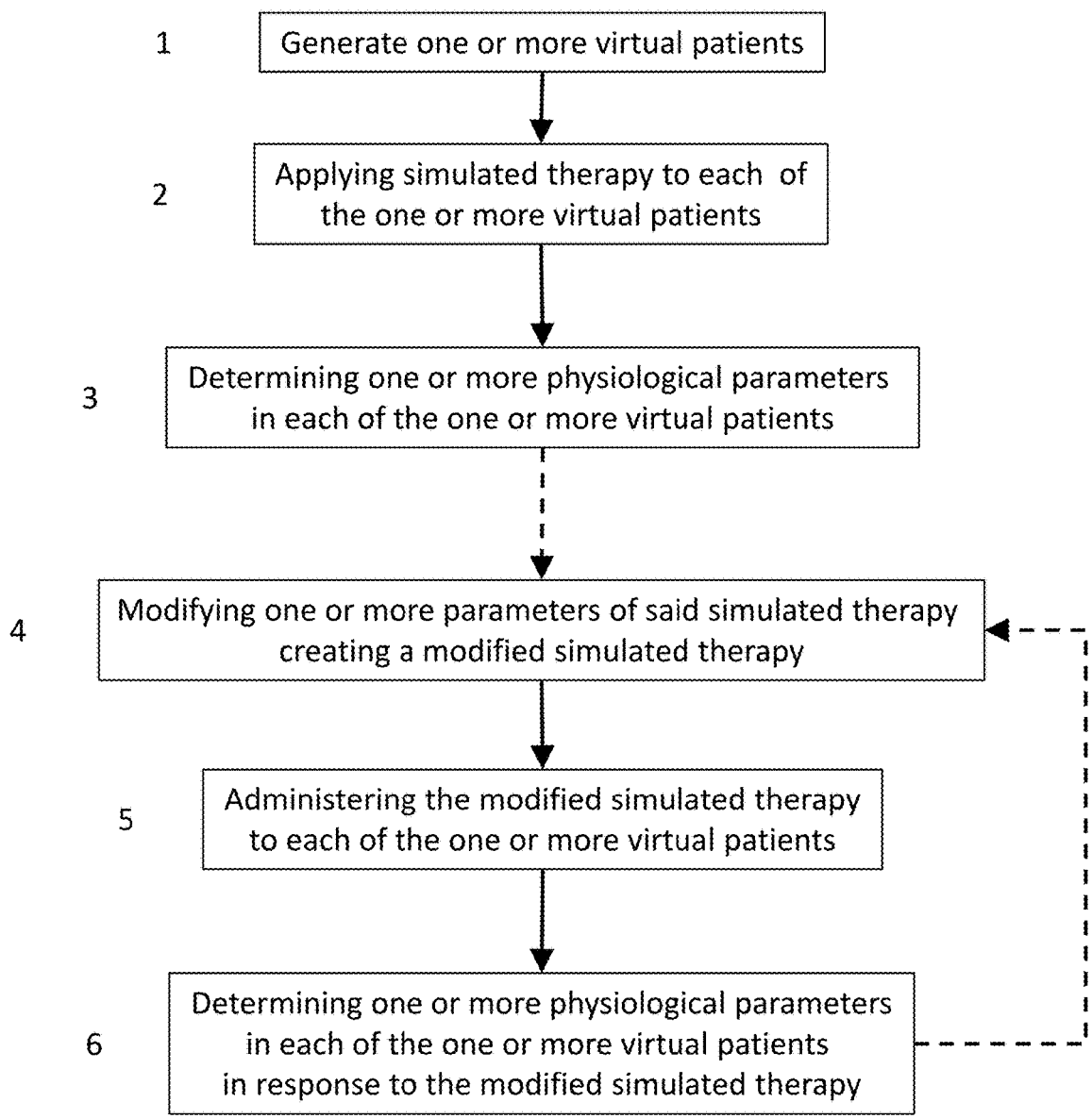
FIG. 2B is a flow diagram of one embodiment of a method according to an embodiment to perform a virtual trial.

For example, as shown in the flow chart depicted in FIG. 2B, in one embodiment, the invention relates to a method for performing a clinical trial, in silico, (herein also referred to as a "virtual clinical trial" or for brevity a "virtual trial") for a health condition, where the method comprises generating in silico one or more virtual patients (step 1). The virtual patients are generated based on data collected from a population of previously treated actual patients suffering from the health condition. The method further comprises applying a simulated therapy to each of the one or more virtual patients (step 2) and determining one or more physiological parameters in the virtual patients in response to the simulated therapy (step 3).

The above method of performing a clinical trial can further comprise performing iteratively the following steps so as to derive an optimal therapy for the health condition: (i) modifying one or more parameters of the simulated therapy, thereby creating a modified simulated therapy (step 4); (ii) administering the modified simulated therapy to each of the virtual patients (step 5); and (iii) determining one or more physiological parameters in the virtual patients in response to the modified simulated therapy (step 6).

Figure 2C:
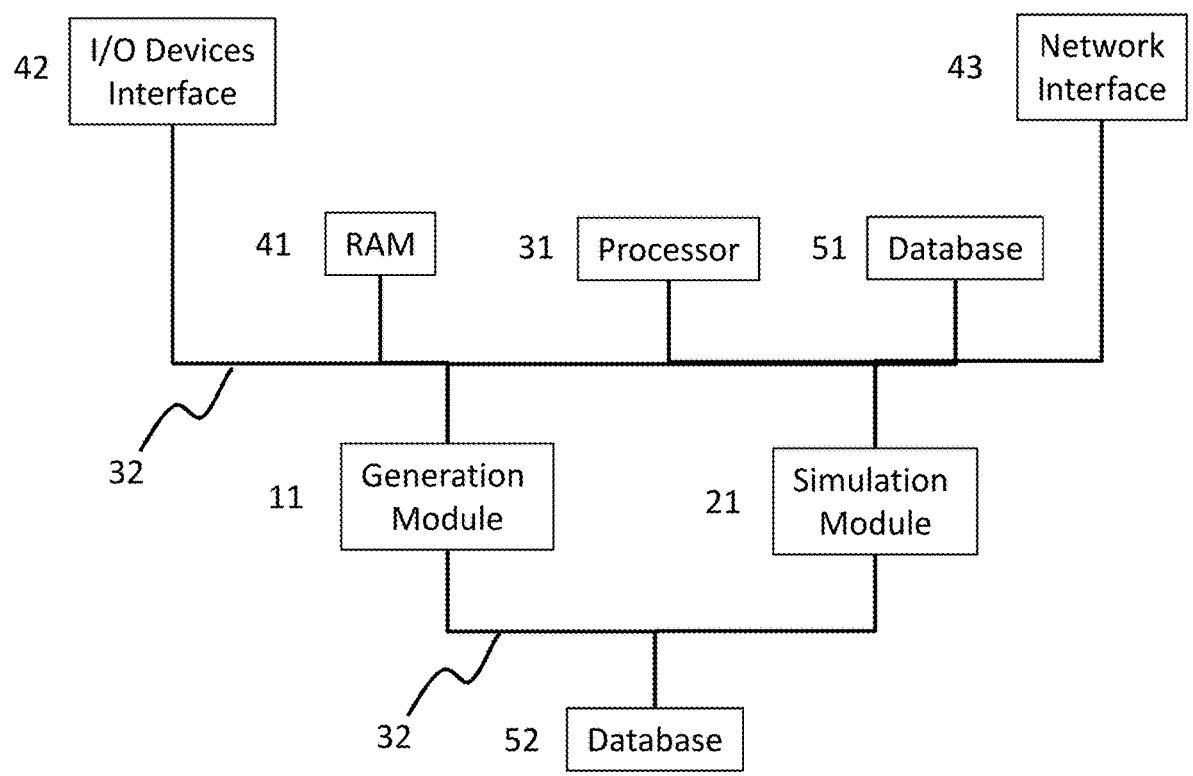
FIG. 2C is a flow diagram of one embodiment of a computer system according to the present teachings.

In another embodiment, the invention relates to a computer system for performing a clinical trial (e.g., determining efficacy of a therapy). By way of example, FIG. 2C schematically depicts a computer system 10 according to an embodiment of the present teachings for determining in silico the efficacy of a therapy. The computer system 10 comprises a generation module 11, a simulation module 21, a processor 31, a random access memory (RAM) 41, an input/output interface 42, and one or more databases, such as database 51 and database 52. Although two databases are depicted in this exemplary embodiment, in other embodiments a single database, or more than two databases, can be employed. A bus 32, which can comprise a set of hardware lines, allows transferring data and instructions among various components of the computer system. The input/output interface 42 allows connecting the computer system to a variety of input/output devices, such as keyboard, mouse, display, printers, speakers, etc. Further, network interface 44 allows the computer system 10 to communicate with other network-enabled devices. The RAM 41 in turn provides volatile storage for computer software instructions and data used to implement the present teachings.

The generation module 11 generates in silico a plurality of virtual patients based on data collected from a population of previously treated patients, e.g., patients suffering from a health condition. The data collected from actual patients can be inputted into the computer system 10 via one or more input/out device and can be stored in database 51 and/or database 52 The generation module 11 can access the stored data to generate virtual patients as mathematical constructs based on the actual patients' data, e.g., in a manner discussed in more detail below. The generated virtual patients can also be stored in database 51 and/or database 52 and can be accessed by the simulation module 21.

The simulation module 21 is configured to apply a simulated therapy to the virtual patients to determine one or more physiological parameters of the virtual patients in response to the simulated therapy. The determined physiological parameters can be stored in database 51 and/or database 52. For example, virtual patients providing a mathematical model of erythropoiesis can be employed to determine hemoglobin concentration and hematocrit level in response to simulated administration of an EPO regimen.

The simulation module 21 can further be configured to adjust the simulated therapy based on the one or more physiological parameters thereby creating a modified simulated therapy. The simulation module 21 can apply the modified simulated therapy to the virtual patients, and determine one or more physiological parameters of the virtual patients in response to the modified simulated therapy. The simulation module 21 can iteratively repeat the process of modifying the therapy and determining one or more physiological parameters until an optimal therapy is obtained. For example, if an initial simulated EPO administration were to result in low hemoglobin concentration, the level of EPO and/or its frequency of administration may be increased and the level of hemoglobin concentration in response to this modified therapy can be determined, to decide whether additional modifications to the EPO regimen is needed.

In some embodiments, the simulation modulation can be configured to recognize one or more physiological parameters determined in response to an applied simulated therapy that are indicative of an adverse effect. Further details regarding a computer system according to various embodiments of the present teachings can be found further below in connection with the description of FIG. 15.

Figure 2D:
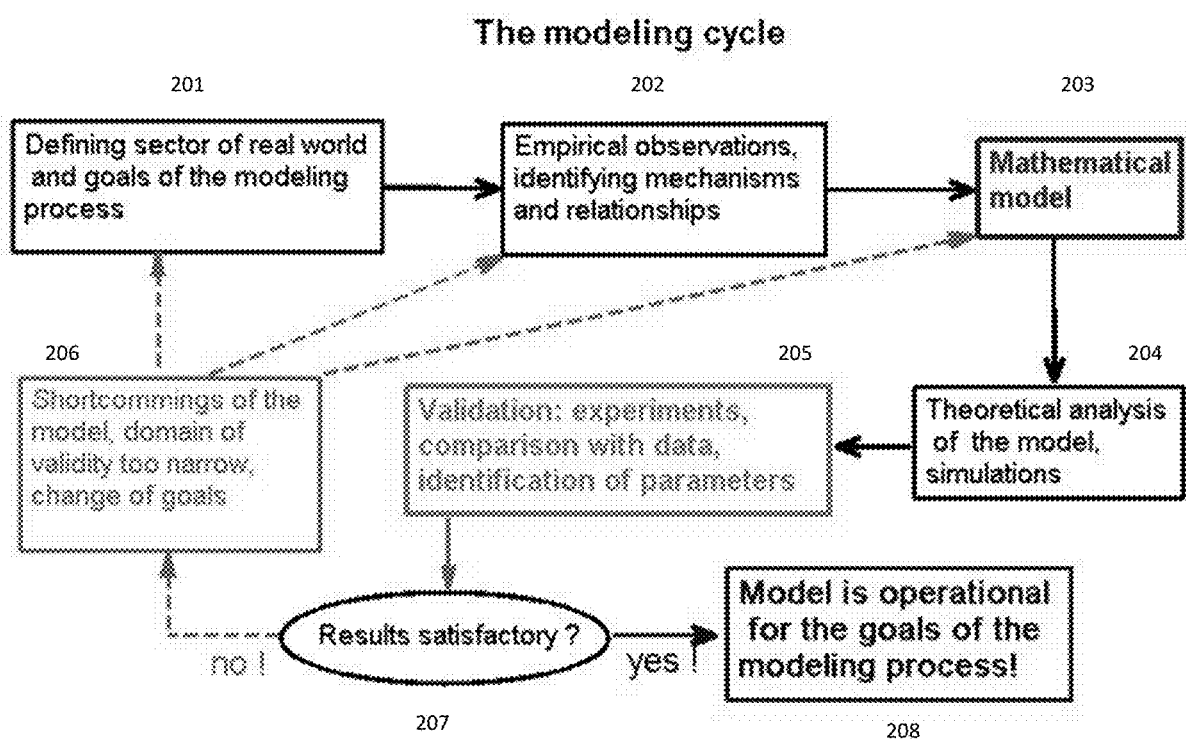
FIG. 2D is a flow diagram modeling a process to determine operational goals of a clinical trial.

Referring to FIG. 2D, a modeling cycling process can be based on a number of factors. First, goals of the modeling process can be defined (201). After empirical observations, and understanding mechanisms and relationships of various factors (202), a mathematical model (203) can be created. Simulations (204) using that mathematical model are then tested and validated with actual experiments (205). These results are examined (207). If the results are not satisfactory, the model can be refined and/or redefined (206). The goals of the model can also be changed according to the findings. However, the results can align with the goals of the model and would then be ready for implementation (208) in a virtual trial.

Figure 3A:
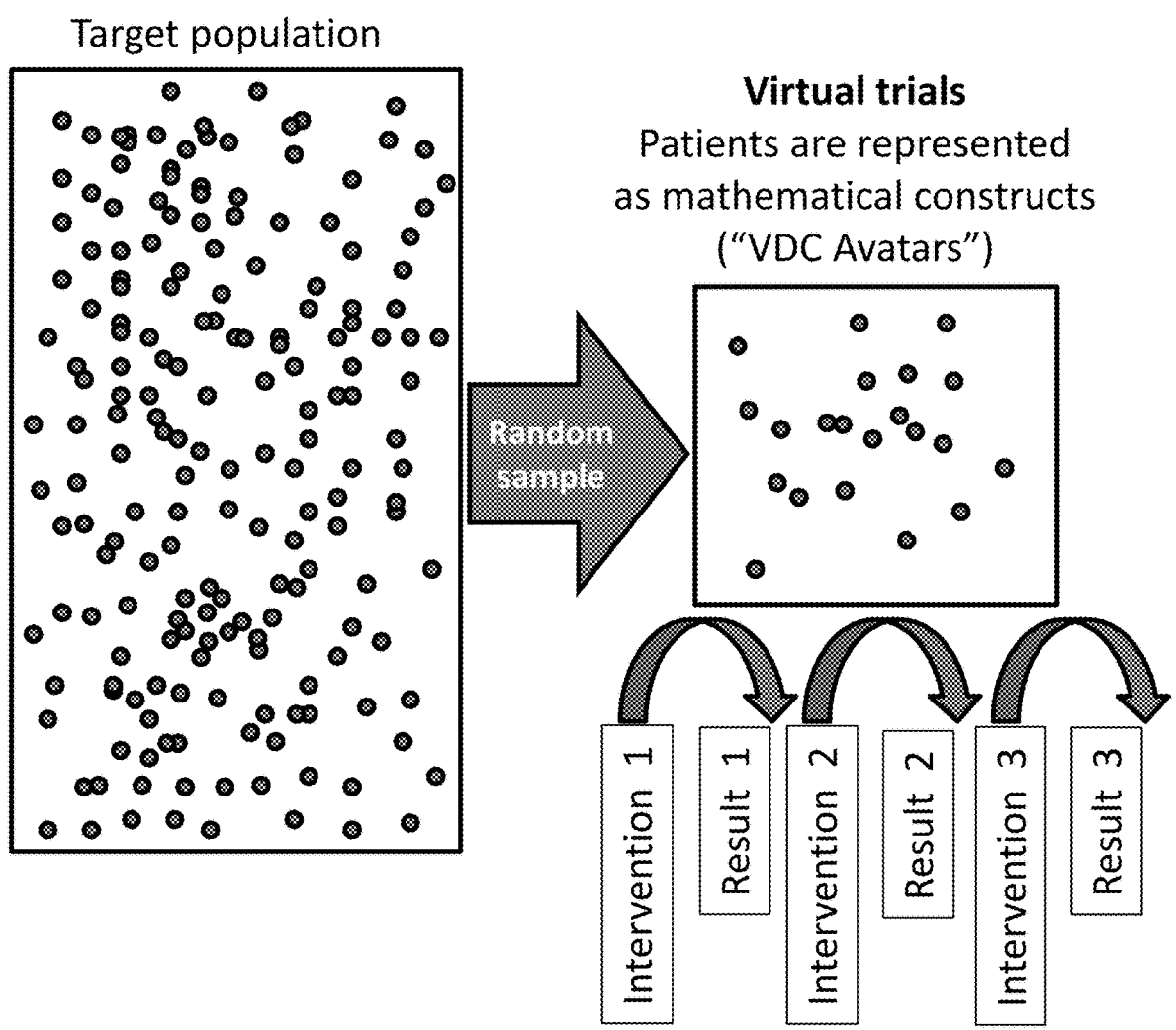
FIG. 3A illustrates generation of virtual patients from a target population for one or more virtual trials.
Figure 3B:
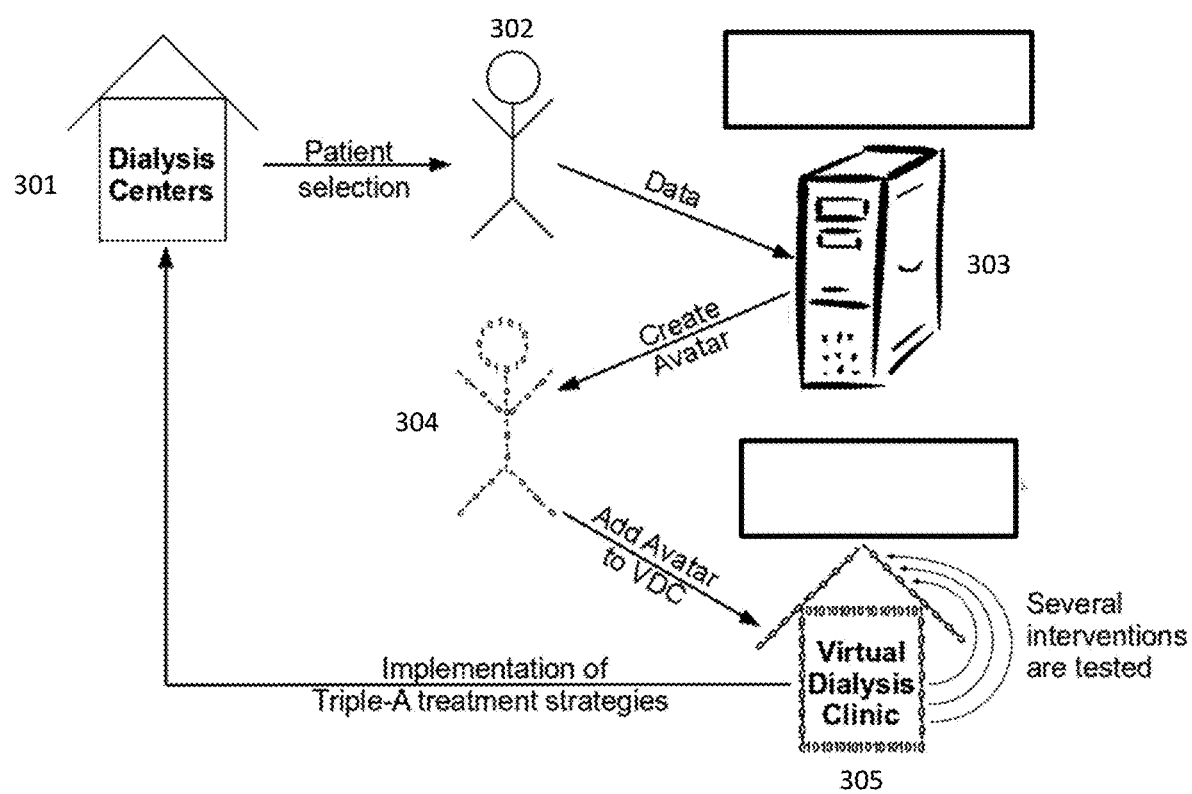
FIG. 3B illustrates a flow diagram of generation of virtual patients according to the present teachings.

Referring to FIGS. 3A-3B, a (one or more) virtual or in silico trial can be performed on a randomized population of virtual patients. For example, intervention 1 can be performed on a random sample of virtual patients, generating result 1. Intervention 2 can also be performed on the random sample of virtual patients, generating result 2. Intervention 3 can be performed on the random sample of virtual patients, generating result 3. Because the virtual trials are performed in silico, interventions 1, 2 and 3 can be done simultaneously or sequentially. For example, in some instances it is preferred to have interventions 1, 2, and 3 performed simultaneously so that results 1, 2, and 3 are known at or around the same time. In other instances, it is preferred to have intervention 1 performed first. Intervention 2 can be then created, modified, or otherwise changed based on result 1 from intervention 1. Then, intervention 3 can also be created, modified, or otherwise changed based on result 2 from intervention 2. For illustration purposes only, FIG. 3A illustrates 3 different interventions providing 3 results. However, it is possible to compute tens, hundreds, and even thousands of interventions (e.g., therapies) on the virtual patients.

FIG. 3B also depicts a diagram of performing a virtual trial according to the present teachings. Virtual patients (avatars) 304 can be created and generated from data obtained from actual patients (e.g., from a dialysis center 301). These virtual patients can be used in any number of virtual clinical trials 305, where one or more interventions are tested. These interventions can be modified or changed according to the outcomes of the virtual clinical trials. Any one of the interventions can then be performed in actual clinics on patients based on the results of the virtual trials.

For example, the mean data from a population of virtual patients in a virtual dialysis clinic is shown in the table in FIG. 12. This data corresponds to the mean values of various parameters, such as age, weight, albumin, EPO dose, ferritin, and others.

Compared to traditional clinical trials, virtual trials according to the present teachings have many advantages. Virtual trials are safe because no actual patients are used. Also, virtual trials can be performed faster since the in silico models can be employed to provide high-throughput evaluations of therapeutic and/or diagnostic alternatives. In some cases, the results of virtual trials can be more reliable than those of traditional clinical trials. For example, in some virtual trials, the absence of inclusion and/or exclusion criteria can increase generalizability and reliability. Virtual trials can also be more inclusive than traditional clinical trials, since classes of patients or individuals that may be excluded from a traditional clinical trial, such as pregnant women, children, and the elderly, can be included in a virtual trial. Further, virtual trials can be more economical than conventional clinical trials, for example, large multicenter clinical trials. In particular, no expensive trial infrastructure is required when performing a virtual trial.

In some embodiments, a virtual trial can determine efficacy of a therapy, medical device and/or a diagnostic intervention. A virtual trial can determine any clinical effect, any outcome, or any change similar to an actual clinical trial. For example, in a virtual trial according to the present teachings, one or more physiological parameters of the virtual patients in response to an applied simulated therapy can be determined. The one or more physiological parameters can allow a clinician or investigator to determine efficacy of the therapy. Further, the physiological parameters may indicate little or no effect, or a positive effect, from the (simulated) therapy. The physiological parameters may indicate an adverse effect from the (simulated) therapy.

Figures 6A, 6B:
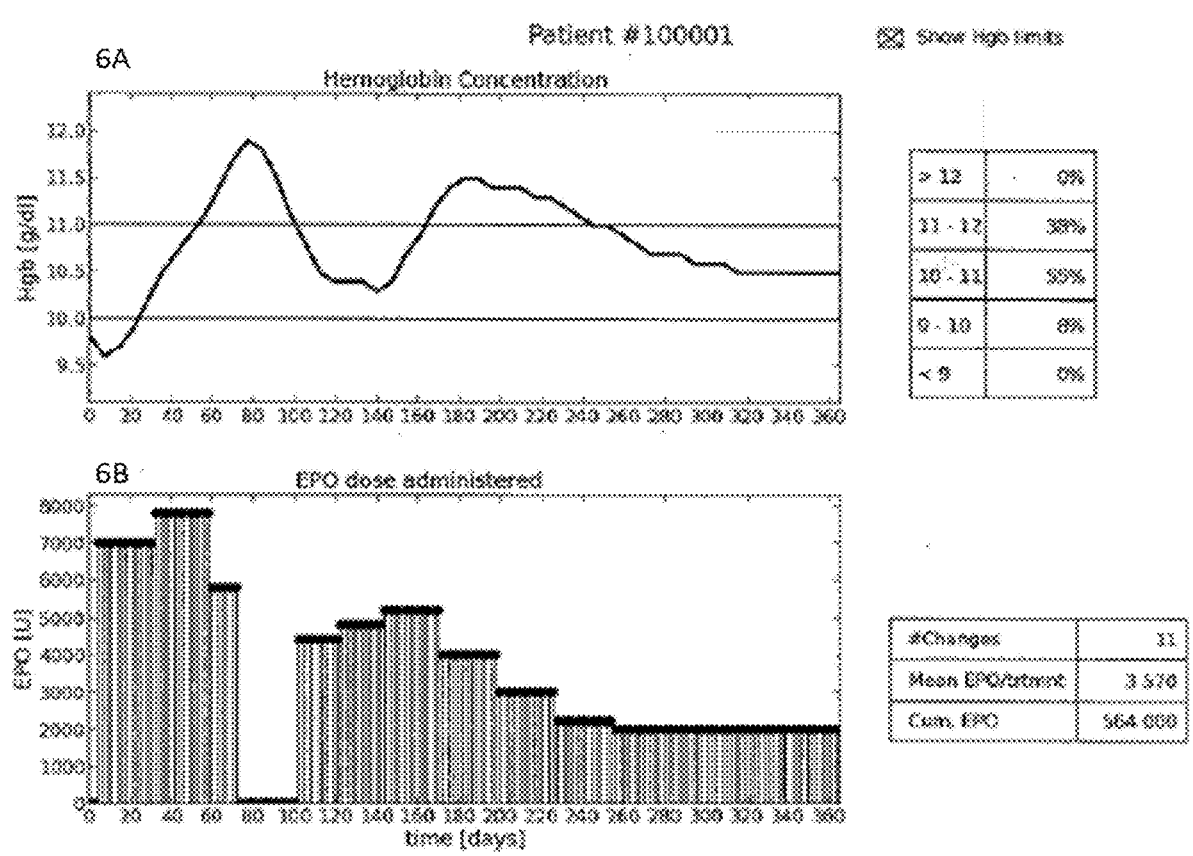
FIGS. 6A-6B illustrate hemoglobin concentration and EPO dose administered as a function of time in a virtual patient.
Figures 7A, 7B, 7C:
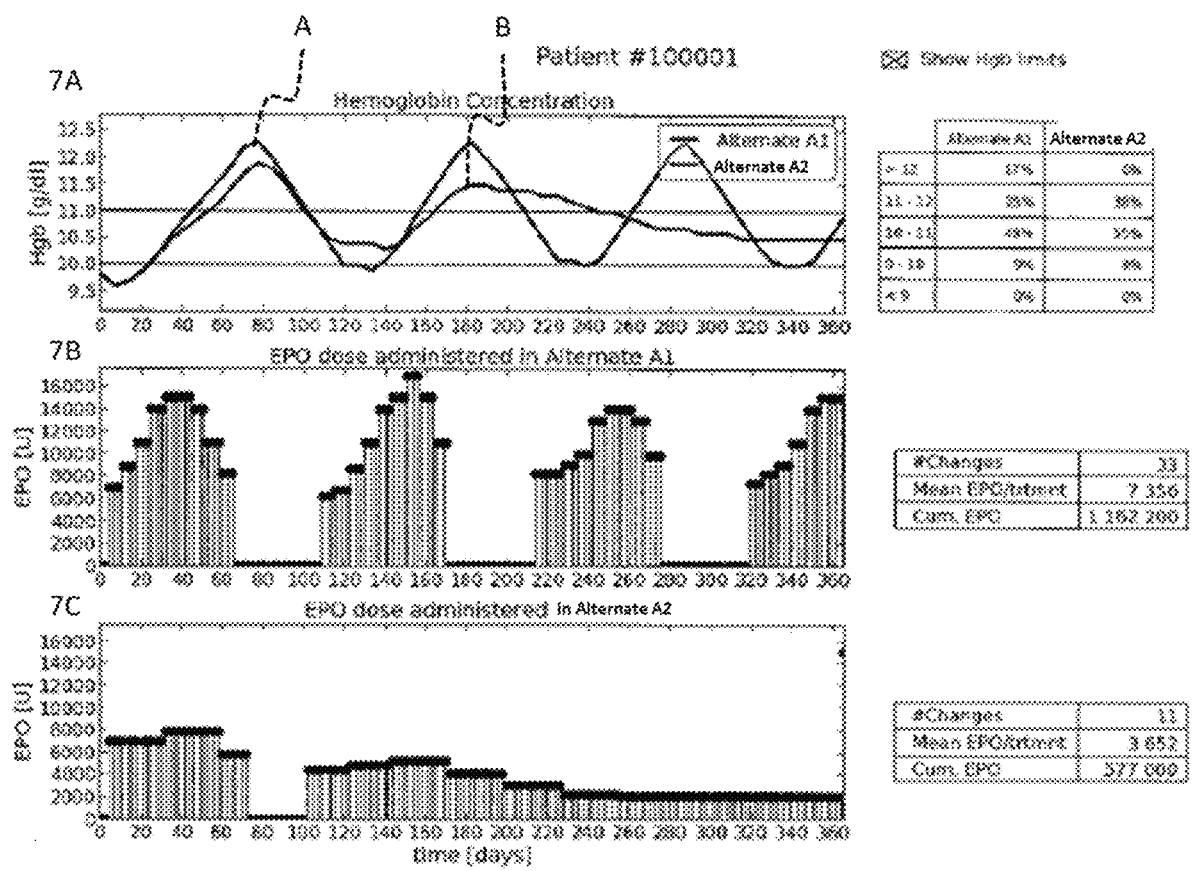
FIGS. 7A-7C illustrate hemoglobin concentration and two different simulated EPO dose administered to a virtual patient as a function of time.
Figures 8A, 8B, 8C:
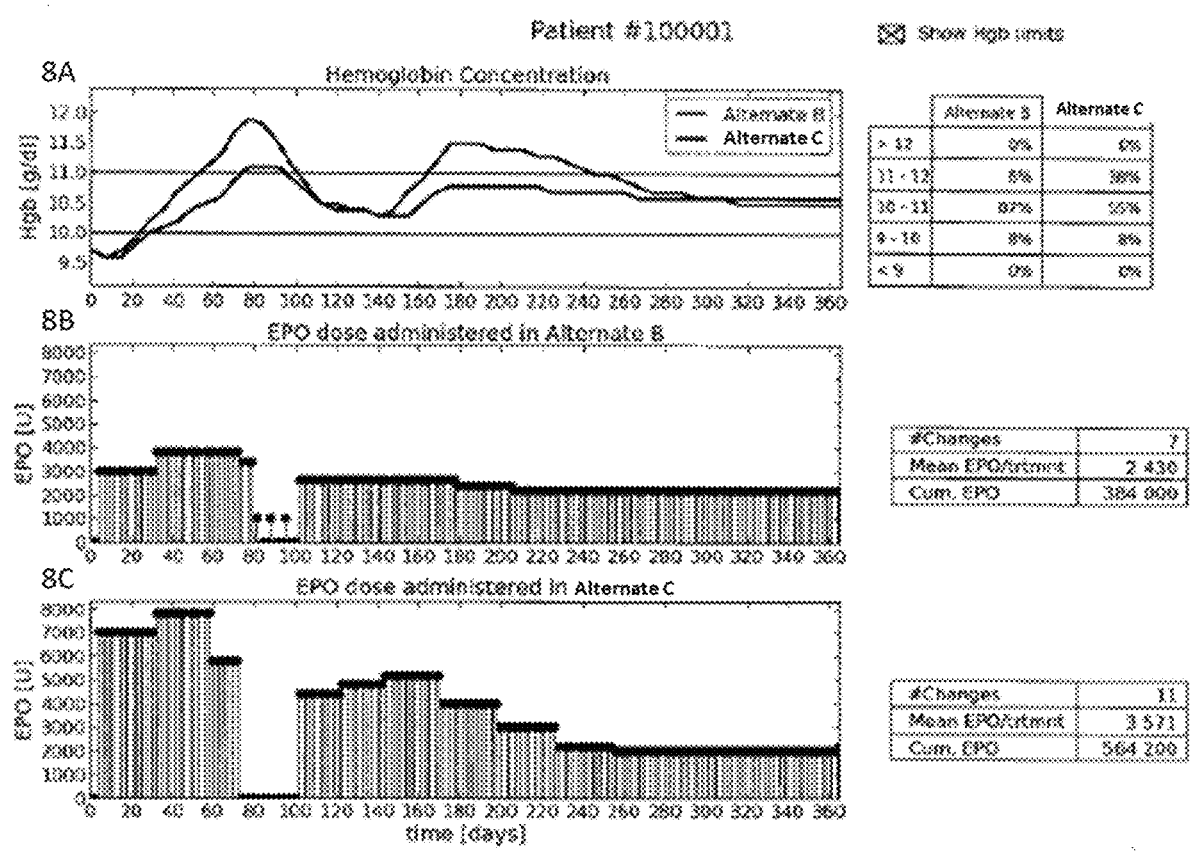
FIGS. 8A-8C illustrate hemoglobin concentration and two different simulated EPO dose administered to a virtual patient as a function of time.

The method for determining efficacy of a therapy can further comprise adjusting the simulated therapy based on the determined one or more physiological parameters of said virtual patients, applying the adjusted therapy to the virtual patients, and determining one or more physiological parameters in response to the adjusted simulated therapy (e.g., FIGS. 6A, 7A, and 8A). The method can further comprise repeating these steps so as to optimize the simulated therapy for application to one or more actual patients.

The one or more physiological parameters can be any parameter measured, determined, or otherwise known in an individual. For example, the one or more physiological parameters can comprise one or more metabolic parameters. Metabolic parameters, for example, can comprise blood or urine parameters. By way of example, blood parameters can comprise hemoglobin, hematocrit, complete blood count (white blood cell, white blood cell differential, neutrophil count, lymphocyte count, monocyte count, eosinophil count), red blood cell, MCV (mean corpuscular volume), MCH (mean corpuscular hemoglobin), MCHC (mean corpuscular hemoglobin concentration), platelet count, or combinations thereof. Other blood parameters can comprise a comprehensive metabolic panel. A comprehensive metabolic panel comprises serum glucose, calcium, BUN (blood urea nitrogen), creatinine, sodium, potassium, chloride, carbon dioxide, total protein, albumin, bilirubin, ALP (alkaline phosphatase), AST (aspartate aminotransferase), ALT (alanine aminotransferase), or combinations thereof.

In a virtual trial described herein, one or more physiological parameters can be determined at a single point or multiple points in time. Multiple points of time can be defined over a predetermined time interval (e.g., 1 day, 1 month, 1 year) or can be open-ended (e.g., indefinitely). Also, a physiological parameter can be determined at any frequency for a given or predetermined time interval. For example, a red blood cell count can be determined every day for as long as a certain therapy is administered.

In a virtual clinical trial, a therapy can comprise a pharmacological therapy, a non-pharmacological therapy, or a combination thereof. For example, a pharmacological therapy can comprise an anemia therapy, a diabetes therapy, a hypertension therapy, a cholesterol therapy, neuropharmacologic drugs, drugs modulating cardiovascular function, drugs modulating inflammation, immune function, production of blood cells; hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. A non-pharmacological therapy can comprise a fluid therapy, a dietary therapy, an exercise therapy, a medical device, diagnostic, extracorporeal therapies, radiotherapy, therapies using sound, including ultrasound, and/or electrotherapies.

In some embodiments, an anemia therapy comprises administering at least one erythropoiesis stimulating agent (ESA), iron, drugs stimulating endogenous erythropoietin release and synthesis (e.g. hypoxia inducible factor (HIF) stabilizers), and/or biosimilars. The ESA can comprise exogenous erythropoietin (EPO), or synthetic EPO. In other embodiments, the EPO comprises recombinant EPO.

By way of example, FIGS. 6A through 8C illustrate graphs of hemoglobin concentration as a function of time in virtual patients in response to simulated administration of EPO according to different regimens. The virtual patients were generated based on an EPO model described in PCT/US2012/054264, entitled "System and Method of Modeling Erythropoiesis and Its Management," which is herein incorporated by reference in its entirety. Each hemoglobin concentration curve (e.g., FIGS. 6A, 7A, and 8A) correspond to an administration of EPO, in silico, over the same time period (360 days). Each of the predicted hemoglobin concentrations is due to a hypothetical administration of EPO. For example, FIGS. 6A and 6B illustrate the effect of simulated administration of EPO on hemoglobin concentration in a virtual patient over a number of days. The EPO dose generally tracks with hemoglobin concentration, i.e., the higher the EPO dose, the greater the hemoglobin concentration and the lower the EPO dose, the lower the hemoglobin concentration.

Different simulated therapies can be administered and compared, such as those illustrated in FIGS. 7A-7C. In FIG. 7B, a bolus-like administration of EPO is applied to a virtual patient for 60 days, with a break in EPO administration (i.e., no EPO administered) for about 40 days. The virtual patients were generated based on an EPO model described in PCT/US2012/054264. This pattern of EPO administration is then repeated. The corresponding hemoglobin concentration determined in the virtual patient is shown in FIG. 7A (graph A). Graph A shows that the hemoglobin concentration exhibits an oscillatory behavior with the peak of the response shifted (delayed) relative to the peak of EPO administration and the minimum of the response shifted relative to the periods of no EPO administration, indicating a delay in response relative to a change in EPO administration. Graph A further shows that the hemoglobin concentration deviates from the desired range of 10 to 11 g/dl during certain temporal periods.

In FIG. 7C, the EPO administration is generally at a lower, more even dose level than that shown in FIG. 7B. The response of the virtual patient to the administration of EPO according to FIG. 7C is shown in graph B in FIG. 7A. Graph B shows a more even response with lower maximum-to-minimum variation.

Similarly, FIGS. 8A-8C also illustrate different simulated EPO administrations (FIGS. 8B and 8C) and how they would affect a virtual patient's hemoglobin concentration (FIG. 8A). The virtual patients were generated based on an EPO model described in PCT/US2012/054264. Specifically, graph A in FIG. 8A shows the temporal variation of the hemoglobin concentration in a virtual patient subjected to the EPO regimen shown in FIG. 8B and graph B in FIG. 8A shows the temporal variation of the hemoglobin concentration in a virtual patient subjected to the EPO regimen shown in FIG. 8C.

The data obtained by applying different EPO regimens to virtual patients can inform selecting an optimal regimen for actual patients. For example, the data provided in FIGS. 7A-7C and 8A-8C discussed above shows that the EPO regimen depicted in FIG. 8C causes a response in hemoglobin concentration that remains within the desired range (i.e., between 10 and 11 g/dl) over essentially the entire period of 360 days, and hence may be more suitable than the other depicted regimens for administration to actual patients.

In some embodiments, a simulated therapy can be adjusted based on the determined one or more physiological parameters. Subsequently, one or more physiological parameters can be determined from the adjusted simulated therapy. The process can be repeated until, e.g., an optimal simulated therapy is obtained, which results in the physiological parameters being in a desired range. It would be generally apparent to one of skill in the art that the physiological parameters determined in the adjusted simulated therapy can be the same or different than the physiological parameters determined in the simulated therapy. In certain embodiments, the one or more physiological parameters are the same in the simulated therapy and the adjusted therapy. In other embodiments the one or more physiological parameters in the simulated therapy can be partially or completely different than the one or more physiological parameters in the adjusted simulated therapy. It will also be appreciated that by virtue of adjusting a therapy, other, different parameters (e.g., physiological parameters) can become important in the virtual trial.

As noted above, a simulated therapy can be adjusted multiple times based on the determined one or more physiological parameters. After each adjusted simulated therapy, one or more physiological parameters can be determined. The simulated therapy can be then readjusted or refined to maximize the outcome (e.g., efficacy) of a therapy. For example, in one embodiment, an optimal therapy for a health condition can be ascertained by iteratively applying a simulated therapy to a plurality of virtual patients, determining values of one or more physiological parameters in the virtual patients in response to the therapy, applying an adjusted simulated therapy to the virtual patients, determining one or more physiological parameters in response to the adjusted therapy until the physiological parameters are within a desired range, indicating that an optimal therapy is achieved.

In one embodiment, the invention relates to a method and system for assessing modifications to a therapy. The method comprises generating in silico a plurality of virtual patients based on data collected from a population of previously treated patients, utilizing said virtual patients to devise a simulated therapy, determining one or physiological parameters of said virtual patients in response to application of said simulated therapy to said virtual patients, modifying one or more parameters of said simulated therapy and determining one or more physiological parameters of said virtual patients in response to application of said modified simulated therapy to said virtual patients, and identifying one or more patients, if any, that respond adversely to said modified simulated therapy based on said determined physiological parameters.

In the above method, the identification of a therapy that leads to adverse effects in one or more patients can be useful in eliminating that therapy from a set of therapies that can be recommended for administration to actual patients.

In one embodiment, the invention relates to a method of determining the effects of non-compliance with a therapeutic protocol in a patient suffering from a health condition. The method comprises generating in silico a virtual patient representing said patient, wherein said virtual patient models said health condition. The method further comprises applying a simulated therapeutic protocol that takes non-compliance into account to said virtual patient, determining one or more physiological parameters of said virtual patient in response to said simulated therapeutic protocol, measuring corresponding one or more physiological parameters of a patient, and comparing said measured one or more physiological parameters with said determined one or more physiological parameters to assess the effects of non-compliance with said therapeutic protocol.

The results of the simulations (e.g., simulated therapy) can be used to make informed decisions about the actual roll-out of specific treatment options. Multiple computer simulations of treatment options in a population can generate extensive amounts of data that would otherwise take months to years to collect in an actual clinical trial. Also, results can be extrapolated to the target population. The most promising treatment options can be selected for further clinical testing or administration to actual patient without further testing.

Virtual Patients

As discussed above, the methods according to the present teachings rely on the generation of patient-specific virtual patients. As discussed in more detail below, each virtual patient is generated so as to mimic at least one physiological system (or subsystem) of an actual patient. In other words, in many embodiments, there is a one-to-one correspondence between a virtual patient and an actual patient based on which the virtual patient is generated. As discussed in more detail below, a virtual patient can be represented by a mathematical model whose adjustable parameters are determined based on data collected from an actual patient. By way of example, the data can be measured hemoglobin concentration in an actual patient suffering from diabetes in response to administration of a regimen of EPO to that patient.

Figure 4A:
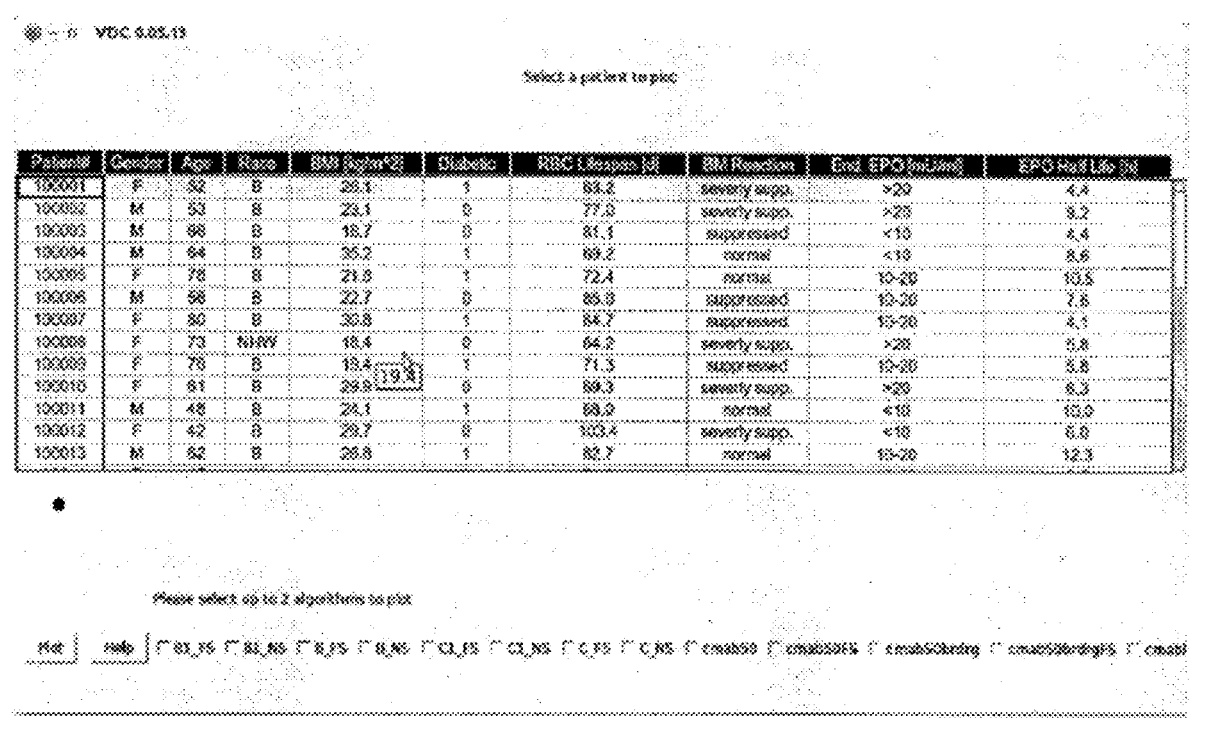

As noted above, a virtual patient is generated, in silico, based on data collected from an actual patient (see, e.g., Table 1 below). A plurality of virtual patients can be created based on data collected from a population of actual patients. For example, FIGS. 4A-4B represent an augmented data set of the VDC, including previously collected data from actual patients (e.g., a dummy patient ID, gender, age, race, BMI, diabetes status) and parameter values determined using advanced mathematical techniques (RBC lifespan, BM (bone marrow) reaction, endogenous EPO concentration and EPO half-life). Each actual patient in a target population can be represented as a mathematical construct (e.g., as a virtual patient). The collected data can represent at least one measured biological response of the previously treated patients to a previously administered therapeutic regimen.

TABLE 1

| Biological characteristics. | |
|---|---|
| | Biological key characteristics |
| "Normal" TBV | 3567 mL |
| Stem cells | $5.92 * 10^{\char`\^}6$ |
| RBC lifespan | 92 days |
| EPO half-time | 4.8 h |
| End. Edo | 5.3 mU/mL |
| Bone marrow reaction | Normal |

Each virtual patient can mathematically represent one or more physiological systems of an actual patient. Previously collected data from the actual patient allows for the construct of such a virtual patient. For example, the collected data can represent at least one measured biological response in the actual patient to a previously administered therapeutic regimen. The data collected from a population of previously treated actual patients can further comprise gender, age, weight, height, ethnicity, metabolic parameters, chemistry parameters, complete blood count, or combinations thereof. Any clinically relevant data or patient information can be used in the construct of a virtual patient. For example, medications taken by the actual patient, past medical history, past surgical history, family history, or combinations thereof can also comprise the data collected from the population of actual patients. Past medical information can include information regarding diabetes, blood pressure/hypertension, cancer, congestive heart failure, kidney disease. Past medical information can also include any information found in the International Statistical Classification of Diseases and Related Health Problems (ICD), such as the ICD-9, including: diseases of the blood and blood-forming organs and certain disorders involving the immune mechanism; endocrine, nutritional and metabolic diseases; mental and behavioral disorders; diseases of the nervous system; diseases of the eye and adnexa; diseases of the ear and mastoid process; diseases of the circulatory system; diseases of the respiratory system; diseases of the digestive system; diseases of the skin and subcutaneous tissue; diseases of the musculoskeletal system and connective tissue; diseases of the genitourinary system; pregnancy, childbirth and the puerperium; certain conditions originating in the perinatal period; congenital malformations, deformations and chromosomal abnormalities; injury, poisoning and certain other consequences of external causes; external causes of morbidity; infectious and parasitic diseases. Collected data from a population of patients can further comprise any information found in their medical records or patient charts.

As previously described, in one embodiment, one or more mathematical models can be used to create a virtual patient. Mathematical models can be used to represent any biological or physiological system, component or subcomponent. For example, any one of the following biological systems can be represented mathematically: circulatory system (lungs with heart, blood and blood vessels), integumentary system (skin, hair, fat, and nails), skeletal system (structural support and protection with bones, cartilage, ligaments and tendons), reproductive system (the sex organs, such as ovaries, fallopian tubes, uterus, vagina, mammary glands, testes, vas deferens, seminal vesicles and prostate), digestive system (digestion and processing food with salivary glands, esophagus, stomach, liver, gallbladder, pancreas, intestines, rectum and anus), urinary system (kidneys, ureters, bladder and urethra involved in fluid balance, electrolyte balance and excretion of urine), respiratory system (the organs used for breathing, the pharynx, larynx, bronchi, lungs and diaphragm), endocrine system (hormones made by endocrine glands such as the hypothalamus, pituitary gland, pineal body or pineal gland, thyroid, parathyroid and adrenals, i.e., adrenal glands), lymphatic system (structures involved in the transfer of lymph between tissues and the blood stream; includes the lymph and the nodes and vessels, includes functions including immune responses and development of antibodies), muscular system (manipulation of the environment, provides locomotion, maintains posture, and produces heat; includes skeletal muscles, smooth muscles and cardiac muscle), and nervous system (collecting, transferring and processing information with brain, spinal cord and peripheral nervous system).

Specific models (modules) can be created for more specific physiological systems, such as, for example, bone mineral metabolism, acid-base metabolism, cardiopulmonary system and tissue oxygenation, and sodium and other mineral homeostasis.

Other physiological systems to which a model (or module) can be created include cardiovascular system; endocrine system; models related to blood cell physiology and immunology; inflammation; hepatic and gastrointestinal function; renal function; and/or musculo-skeletal function.

For example, a virtual patient can be constructed using an anemia model described herein. The model can be fitted to actual patient data (e.g., hemoglobin concentration) to obtain values for certain parameters of the model. In some embodiments, other parameters, such as blood volume and the number of stem cells committed to the erythroid lineage can be estimated based on gender, weight, and height of the patient. Other parameters can be adapted for each individual patient, such as, red blood cell life span, endogenous EPO production, half-life of epoetin-alfa, bone marrow reaction to EPO, rate of apoptosis of CFU-E cells, and maturation velocity of reticulocytes.

By way of example, measured data indicating the hemoglobin concentration of a diabetic actual patient in response to administration of an EPO regimen to that patient can be used to determine values for certain parameters of a virtual patient representing that actual patient. For example, such data can be utilized to determine one or more adjustable parameters of a mathematical model for Erythropoiesis. For example, the parameters can be adjusted so as to obtain a simulated response (e.g., a response characterized by hemoglobin concentration) to simulated administration of the shown EPO regimen that is sufficiently close to the actual response. In some cases, a merit function can be employed to quantify the difference between the simulated response and the actual response. The parameters can be adjusted until the merit function indicates an acceptable difference between the simulated and the actual responses.

Figure 5A:
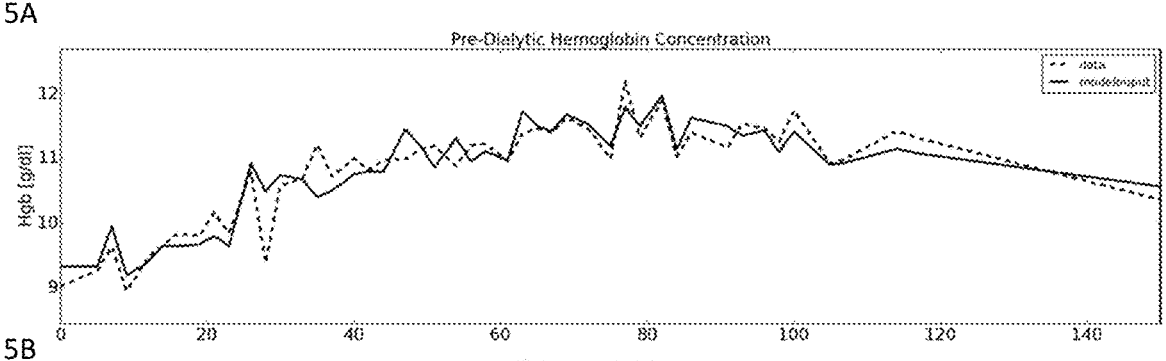
FIGS. 5A-5B illustrate hemoglobin concentration and EPO dose administered as a function of time in a patient.
Figure 5B:
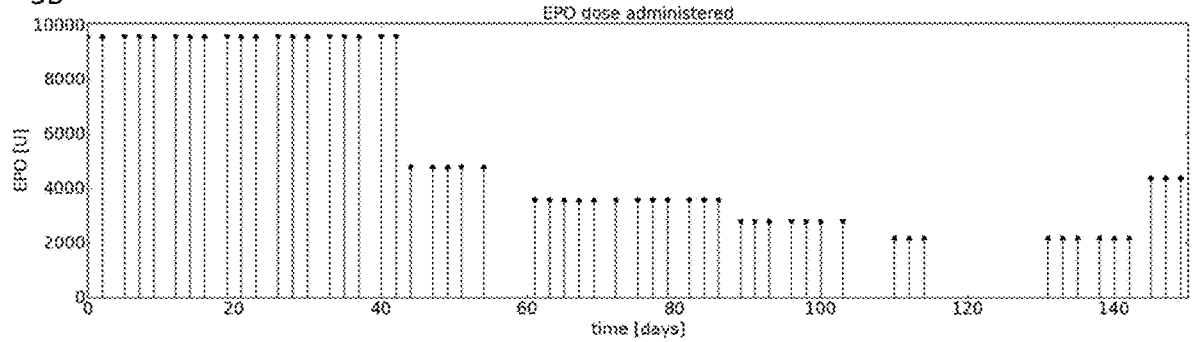

By way of further illustration, FIGS. 5A and 5B, represent, respectively, measured hemoglobin concentration over a period of time and EPO administered to that patient over the same period of time. The patient was a female individual, 163 cm in height, and about 66.9-68.2 kg in weight during the course of treatment. From this patient information, it was determined that the average red blood cell lifespan was approximately 63.2 days, endogenous EPO production was greater than 20 mU/ml (milli-units per milliliter), the bone marrow was severely depressed and the half-life of Epoetin alfa was about 4.4 hours. This data was utilized for determine values for certain parameters of a mathematical model for generating red blood cells (by adjusting the parameters to obtain a desired fit to the data).

As noted above, for each patient, a patient specific virtual patient or avatar is created. A database of virtual patients can be created from a database of actual patients. From the database of virtual patients, one or more virtual patients can be selected for each virtual clinical trial. In some cases, specific virtual patients can be selected to determine the answers to questions that would be difficult or impossible to answer in an actual clinical trial. As noted above, individuals that would not be typically included in a clinical trial can be easily included in a virtual trial. Virtual patients who are, for example, very old, very young, and/or pregnant can be included in a virtual trial.

For example, an anemia therapy (erythropoiesis) model can be used to create a virtual patient to study medicines and therapies effecting red blood cell production, hemoglobin, hematocrit, or combinations thereof. Each of the essential aspects of erythropoiesis can be represented in each virtual patient, described herein. The virtual patients can then be subjected to one or more anemia treatment schemes. Other mathematical models can be used to represent other physiological systems. For example, as shown in FIG. 10, mathematical models can be used to represent anemia (erythropoiesis) fluid status, inflammation, and/or iron metabolism. Additional details regarding the erythropoiesis model is described below.

Further details regarding an erythropoiesis model suitable for generating a virtual patient according to the present teachings for modeling red blood cell production in actual patients can be found in U.S. Published Patent Application No. 2014/0128791, entitled "System and Method of Modeling Erythropoiesis Including Iron Homeostasis," which is herein incorporated by reference in its entirety.

Figure 11:
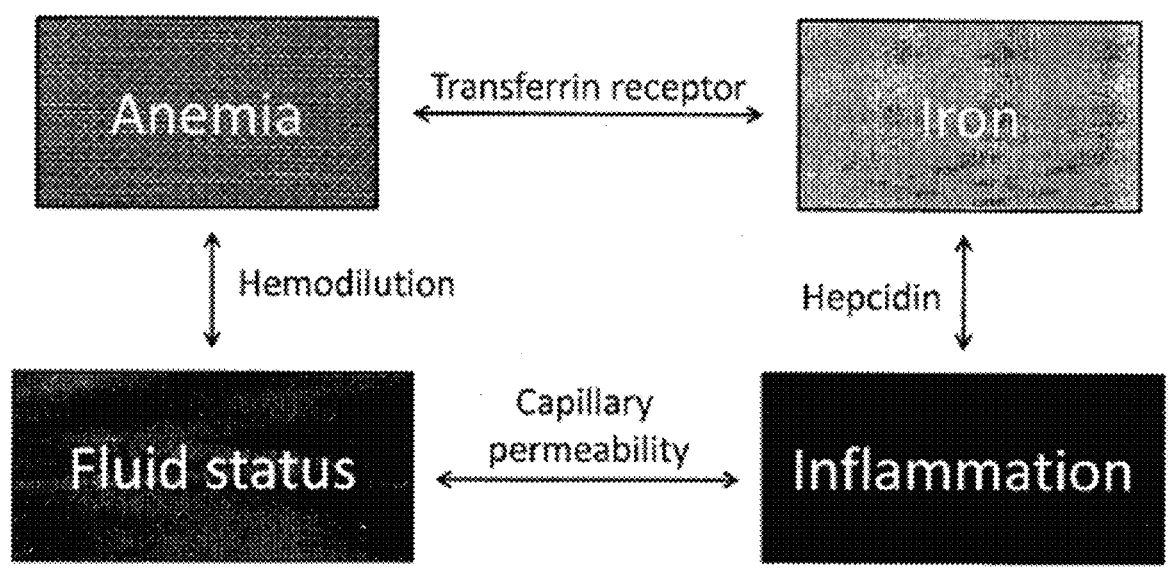
FIG. 11 illustrates the interrelationship between different physiological systems that can be represented in a mathematical model.

Referring to the scheme illustrated in FIG. 11, in some embodiments, various modules representing physiological systems of an actual patient can interact in silico to obtain a better understanding of the response for a patient to various therapeutic protocols. For example, the depicted model can allow answering questions such as: How does better fluid management affect ESA and iron utilization? What is the effect of iron delivery in the dialysate on ESA utilitization? How does an anti-inflammatory intervention affect anemia control?

Additional modules can comprise any module for a physiological system or pathway. For example, there can be a module for bone mineral metabolism, acid-base metabolism, cardiopulmonary system, renal and/or sodium model in, e.g., chronic kidney disease.

Anemia Therapy (Erythropoiesis) Model
Red Blood Cell Physiology

Red blood cells (erythrocytes) are essential for the distribution of oxygen through the body to organs and tissues. They take up oxygen in the lungs and deliver it to tissues while squeezing through the capillaries. To fulfill this task properly, they are highly specialized. For instance, being shaped like biconcave disks optimizes the oxygen exchange. Furthermore, the nuclei, organelles, and mitochondria have been expelled in earlier developmental stages, and therefore more space for hemoglobin, the molecule which oxygen binds to, is available. Erythrocytes are very deformable and can therefore pass capillaries half their diameter. During microcirculation, they have to withstand high shear stresses, rapid elongation, folding, and deformation. Over time, the cell membrane is damaged by these extraordinary stresses. Because of the lack of nuclei and organelles, red blood cells cannot divide or repair their cell membranes. Senescent erythrocytes lose their flexibility due to their fragmented membranes. These stiff cells could do harm to small capillaries or even clog them. To avoid this potential harm, old erythrocytes are recognized by phagocytes and destroyed. This phagocytosis mainly takes place in the spleen and cells of the reticulo-endothelial system (RES). See Jandl, J. H., Blood: Textbook of Hematology, 2nd Ed. Little, Brown and Company, 1996 (hereinafter "Jandl").

To compensate for phagocytosis of senescent red blood cells, it is necessary to build new erythrocytes continuously. The maturation of undifferentiated stem cells to mature erythrocytes is called erythropoiesis and takes place in the bone marrow. Erythropoiesis not only has to compensate for the continuous loss of old erythrocytes, but also for the additional loss of cells due to random breakdown, as well as due to internal and external bleeding. Furthermore, the number of red blood cells has to be adjusted to varying environmental conditions, as for instance a transition from low to high altitudes or vice versa, by increasing the rate of erythropoiesis, or, conversely, by neocytolysis, a process believed to be wherein macrophages start to phagocytose young erythrocytes (neocytes).

Figure 13:
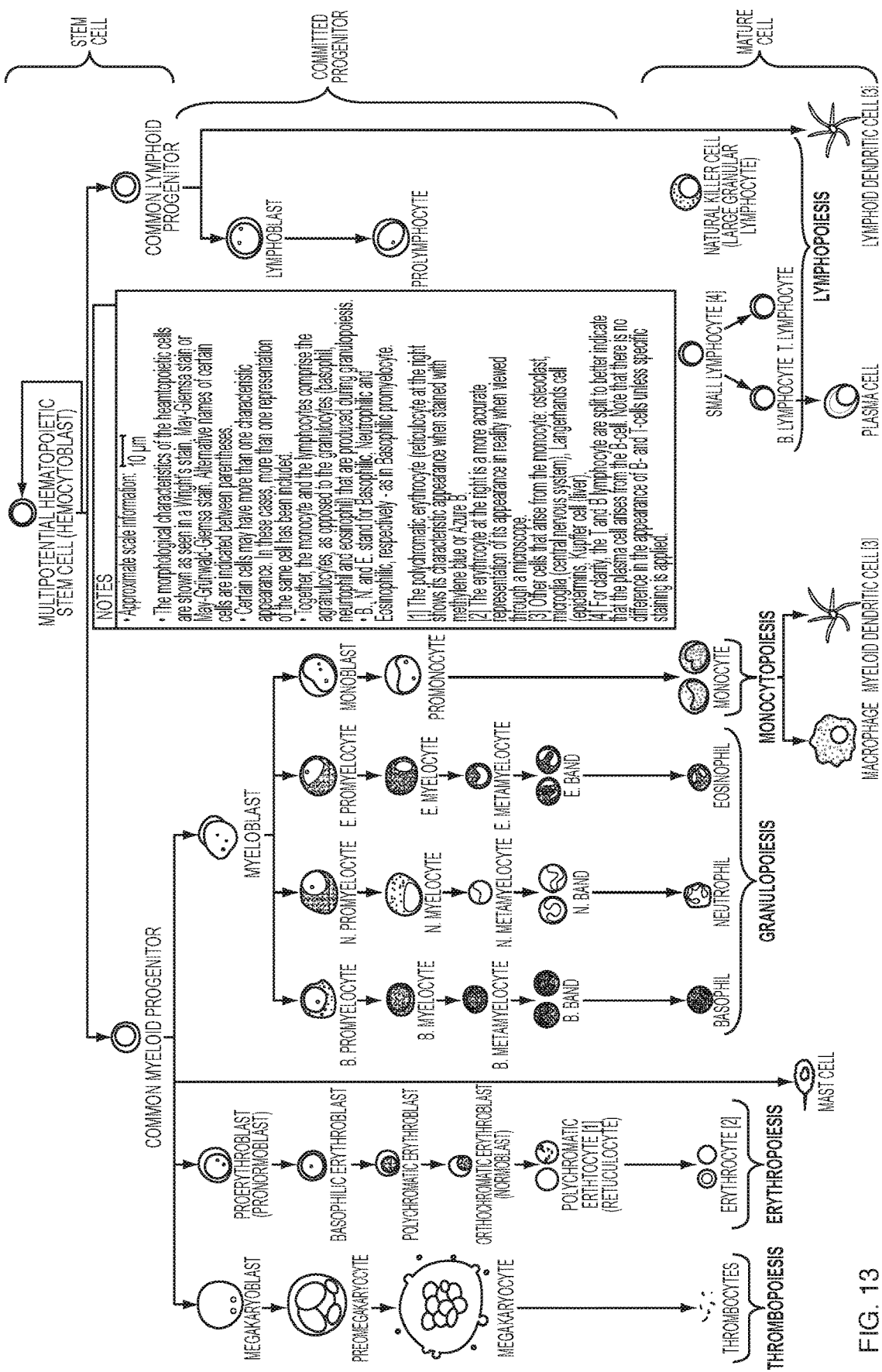
FIG. 13 illustrates the erythropoiesis in humans.

During the process of erythropoiesis, the cell population undergoes a series of proliferations and differentiations (see FIG. 13). Starting from multipotential stem cells, erythroid cells mature to BFU-Es (earliest stage of erythroid committed cells), CFU-Es, different stages of erythroblasts, and finally reticulocytes. The reticulocytes are released from the bone marrow into blood and mature within 1-2 days to erythrocytes (see FIG. 9A).

The primary control of erythropoiesis is governed by the hormone erythropoietin (EPO). EPO is released into the blood stream by the kidneys based on a negative feedback mechanism that reacts to the partial pressure of oxygen in blood. The concentration of EPO affects the number of circulating red blood cells by determining the number of cells that mature into erythrocytes, either by recruitment or by preventing apoptosis (programmed cell death), and by affecting the velocity of maturing of progenitor and precursor cells. Thus, disturbances in oxygen delivery can be adjusted for by an adaptive resetting of the rate of erythropoiesis. Additionally, as already mentioned above, there exists a physiological process which affects the selective degradation of young erythrocytes in situations of red cell excess, called neocytolysis. Neocytolysis seems to be triggered by a drop in the EPO level. See Rice, L., and Alfrey, C. P., Cellular Physiology and Biochemistry, 2005, Vol. 15, pp. 245-250 (hereinafter "Rice 2005"); Rice, L., Alfrey, C. P., Driscoll, T., Whitley, C. E., Hachey, D. L., and Suki, W., Amer. J. Kidney Diseases, 1999, Vol. 33, pp. 59-62 (hereinafter "Rice 1999"); and Rice, L., W. Ruiz, W., Driscoll, T., Whitley, C. E., Tapia, R., Hachey, D. L., Conzales, G. F., and Alfrey, C. P., Annals Internal Medicine. 2001, Vol. 134, pp. 652-656 (hereinafter "Rice 2001").

Another critical factor for effective erythropoiesis is the availability of iron which is indispensable for hemoglobin synthesis. If the body is not able to provide sufficient iron for this process, then ineffective erythropoiesis will result. See Finch, S., Haskins, D., and Finch, C. A., The Journal of Clinical Investigation. 1950, Vol. 29, pp. 1078-1086; and Lichtman, M. A., E. Beutler, E., Kipps, T. J., Seligsohn, U., Kaushansky, K., and Prchal, J. T. (editors), Williams Hematology, 7th edition, New York, McGraw-Hill, 2005 (hereinafter "Williams Hematology"). In normal subjects, the total iron content of the body stays within narrow limits (iron overload is toxic). Once an atom of iron enters the body it is conserved with remarkable efficiency and can remain in the body for more than ten years. Iron is lost via loss of cells (especially epithelial cells), bleeding and loss of very small amounts via urine and sweat. The balance of iron content is achieved by absorption and not by control of excretion. If the plasma concentration of iron is too low, then the level of the hormone hepcidin is decreased. The consequence of a lower hepcidin level is that more iron is taken up via the duodenum and more iron is released from macrophages and from the stores. See Crichton, R., Iron Metabolism. From Molecular Mechanisms to Clinical Consequences, New York, J. Wiley, 2009 (hereinafter "Crichton"); Fleming, M. D., J. Amer. Soc. Hematology, 2008, pp. 151-158 (hereinafter "Fleming"). Patients suffering from inflammation, such as dialysis patients, typically have higher hepcidin levels. Increasing iron availability in inflamed dialysis patients can be achieved by an increase of parenteral iron by increasing dose, frequency, or both, and by reducing inflammation by diagnosis and treatment of sources of inflammation, e.g., barrier breakdown (i.e., skin, periodontal disease, intestinal congestion), pulmonary or urinary tract infection, thrombosed fistulas or catheter, and by subsequent specific therapy, e.g., antibiotics, catheter removal, aseptic techniques when manipulating in-dwelling catheters, and surgical debridement of skin ulcers.

Since individual cells in the various cell populations which have to be considered have to be distinguished according to their age, age-structured population models are needed in order to describe the development of the cell populations. Besides these age-structured population models, the model of this invention includes a feedback loop including erythropoietin.

In one embodiment, a method of adjusting a patient's hematocrit and/or hemoglobin concentration to a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, the model including iron homeostasis, and employing the patient parameters and an initially selected ESA administration regimen in the model to predict the patient's hematocrit and/or hemoglobin concentration at the predetermined time with the initially selected ESA administration regimen. Examples of ESAs are provided in Table 2 (adapted from Phurrough S, Jacques L, Ciccanti M, Turner T, Koller E, Feinglass S: "Proposed Coverage Decision Memorandum for the Use of Erythropoiesis Stimulating Agents in Cancer and Related Neoplastic Conditions"; Centers for Medicare and Medicaid Services; Administrative File: CAG #000383N; May 14, 2007). See also Pfeffer, M. A., Burdmann, E. A., Chen, C-Y., Cooper, M. E., de Zeeuw, D., Eckardt, K-U., Feyzi, J. M., Ivanovich, P., Kewalramani, R., Levey, A. S., Lewis, E. F., McGill, J. B., McMurray, J. J. V., Parfrey, P., Parving, H-H., Remuzzi, G., Singh, A. K., Solomon, S. D., Toto, R., The New England Journal of Medicine, 2009, 361(21), pp. 2019-2032; and Singh, A. K., Szczech, L., Tang, K. L., Barnhart, H., Sapp, S., Wolfson, M., Reddan, D., The New England Journal of Medicine, 2006, 355(20), pp. 2085-2098 (hereinafter "Singh et al."). Note that unlike other ESAs listed in Table 2, Peginesatide is not a biologically derived EPO; it is a synthetic peptide that stimulates EPO receptors.

TABLE 2

Erythropoiesis Stimulating Agents (EPO = erythropoietin).

| Compound | Drug Names | Manufacturer |
| --- | --- | --- |
| EPO α | Epogen | Amgen |
| EPO α | Procrit | Amgen |
| EPO α (w/o serum albumin) | Eprex, Epypo Epopen, Epoxitin, Globuren | J&J subsidiary (Otho Biologics) |
| EPO β | (Neo)Recormon | Roche |
| EPO β | Erantin | Boehringer Mannheim (Spain), Roche (Spain) |
| EPO β | Epoch | Chugai |
| EPO δ in human cell lines | Dynepo Gene Activated EPO | Aventis Transkaryotic Therapies |
| EPO Ω | Epomax, Hemax, Hemax-Eritron | Baxter |
| Modified EPO α Darbepoietin | Aranesp | Amgen |
| Modified EPO α Darbepoietin | Nespo | Amgen |
| Modified EPO β Continuous EPO Receptor Activator (Pegylation) | Mircera | Roche |
| Peginesatide | Omontys | Affymax |

Optionally, if the patient's hematocrit and/or hemoglobin concentration is not predicted by the model to be in the desired range at the predetermined time with the initially selected ESA administration regimen, the method includes employing the model with one or more different ESA administration regimens until the model predicts that the patient's hematocrit and/or hemoglobin concentration will be in the desired range at the predetermined time. The method then includes administering ESA to the patient with an ESA administration regimen predicted to adjust the patient's hematocrit and/or hemoglobin concentration to a value within the desired range at the predetermined time. The ESA administration regimen can include iron administration, and the model includes iron homeostasis with iron administration, and modeling the influence of iron homeostasis on erythropoiesis. The patient parameters can include, for example, the starting hematocrit and/or hemoglobin concentration in the patient's blood, the total blood volume of the patient, the lifespan of red blood cells (RBCs) of the patient, the mean corpuscular volume of the RBCs, the rate of neocytolysis in the patient's blood, the distribution of cell hemoglobin content in the patient's blood, the distribution of red blood cell size, iron storage level of the patient, transferrin saturation (TSAT), serum transferrin receptors, red cell zinc protoporphyrin level, hypochromic red blood cells, hypochromic reticulocytes, ferritn, endogenous EPO levels, C-reactive protein (CRP) levels, interleukin-6 (IL-6) levels, and the hepcidin levels of the patient.

The starting hematocrit and/or hemoglobin concentration in the patient's blood can be obtained from routine laboratory measurements known in the art. The total blood volume (BV) of the patient can be estimated as described further below, or measured by use of radio-labeling red blood cells with chromium-51 to estimate red blood cell volume (RCV) and using the formula $$BV=RCV/(0.9*Hctv)$$

where Hctv is the venous hematocrit, obtained from routine laboratory measurements known in the art. See Albert S. N., Blood volume measurement, In: Nuclear Medicine In Vitro. 2 ed. Philadelphia: JB Lippincott Co., 1983; Bernard P. J., Nouv Rev Fr Hematol 1994, 36(2), pp. 155-157; and International Committee for Standardization in Haematology: Recommended methods for measurement of red-cell and plasma volume, J Nucl Med 1980, 21(8), pp. 793-800. The lifespan of RBCs of the patient can be estimated from endogenous alveolar carbon monoxide concentrations. See Strocchi A., Schwartz S., Ellefson M., Engel R. R., Medina A., Levitt M. D., J Lab Clin Med 1992, 120(3), pp. 392-399. The mean corpuscular volume can be obtained from routine laboratory measurements known in the art. The rate of neocytolysis in the patient's blood can be estimated from correlations with reduced expression of CD44 (homing-associated cell adhesion molecule) and CD71 (transferrin receptor). See Chang C. C., Chen Y., Modi K., Awar O., Alfrey C., Rice L., J Investig Med 2009, 57(5), pp. 650-654.

The models of this invention can track the patient's predicted hematocrit and/or hemoglobin concentration over time, such as between about 5 days and about 200 days of the ESA administration regimen. The predetermined time can be any future time after an ESA administration regimen is selected and the predicted regimen is initiated. In some embodiments, the patient undergoes a medical procedure prior, during, or after the ESA administration regimen, such as blood donation, surgery, and dialysis, or any combination thereof. For dialysis patients, the desired hematocrit is typically in the range of between about 28 percent and about 36 percent and the desired hemoglobin concentration is typically in a range of between about 9.5 g/dL and about 12 g/dL. See Driieke, T. B., Locatelli, F., Clyne, N., Eckardt, K.-U., Macdougall, I. C., Tsakiris, D., Burger, H-U., Scherhad, A., The New England Journal of Medicine, 2006, 355(20), pp. 2071-2084; Parfrey, P. S., 2006, American Journal of Kidney Diseases, 47(1), pp. 171-173; Strippoli, G. F. M., Craig, J. C., Manno, C., Schena, F. P., Journal of the American Society of Nephrology, 2004, 15, pp. 3154-3165 (hereinafter "Strippoli et al."); Volkova, N., Arab, L., Evidence-Based Systematic Literature Review of Hemoglobin/Hematocrit and All-Cause Mortality in Dialysis Patients, 2006, 47(1), pp. 24-36. For elective orthopaedic surgery patients, the desired hemoglobin concentration for males and females is typically greater than or equal to 13 g/dL, and 12 g/dL, respectively. See Goodnough L. T., Maniatis A., Earnshaw P., Benoni G., Beris P., Bisbe E., Fergusson D. A., Gombotz H., Habler O., Monk T. G., Ozier Y, Slappendel R., and Szpalski M., British Journal of Anaesthesia 106 (1) pp. 13-22 (2011).

In another embodiment, a method of determining a patient's hematocrit and/or hemoglobin concentration within a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, the model including iron homeostasis, and employing the patient parameters and an initially selected EPO administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, or a different ESA administration regimen is desired due to other considerations, the method includes employing the model with one or more different ESA administration regimens until the model predicts that the patient's hematocrit and/or hemoglobin concentration will be in the desired range at the predetermined time. The method then can include administering ESA to the patient with the ESA administration regimen predicted to adjust the patient's hematocrit and/or hemoglobin concentration to a value within the desired range at the predetermined time.

In yet another embodiment, a hemodialysis system includes a hemodialysis machine including a blood pump, a modular drug delivery device comprising at least one erythropoiesis stimulating agent (ESA) pump, at least one iron replacement product pump, at least one ESA vial holder, and at least one iron replacement product vial holder, and a housing to which the blood pump and the modular drug delivery device are secured.

Figure 16:
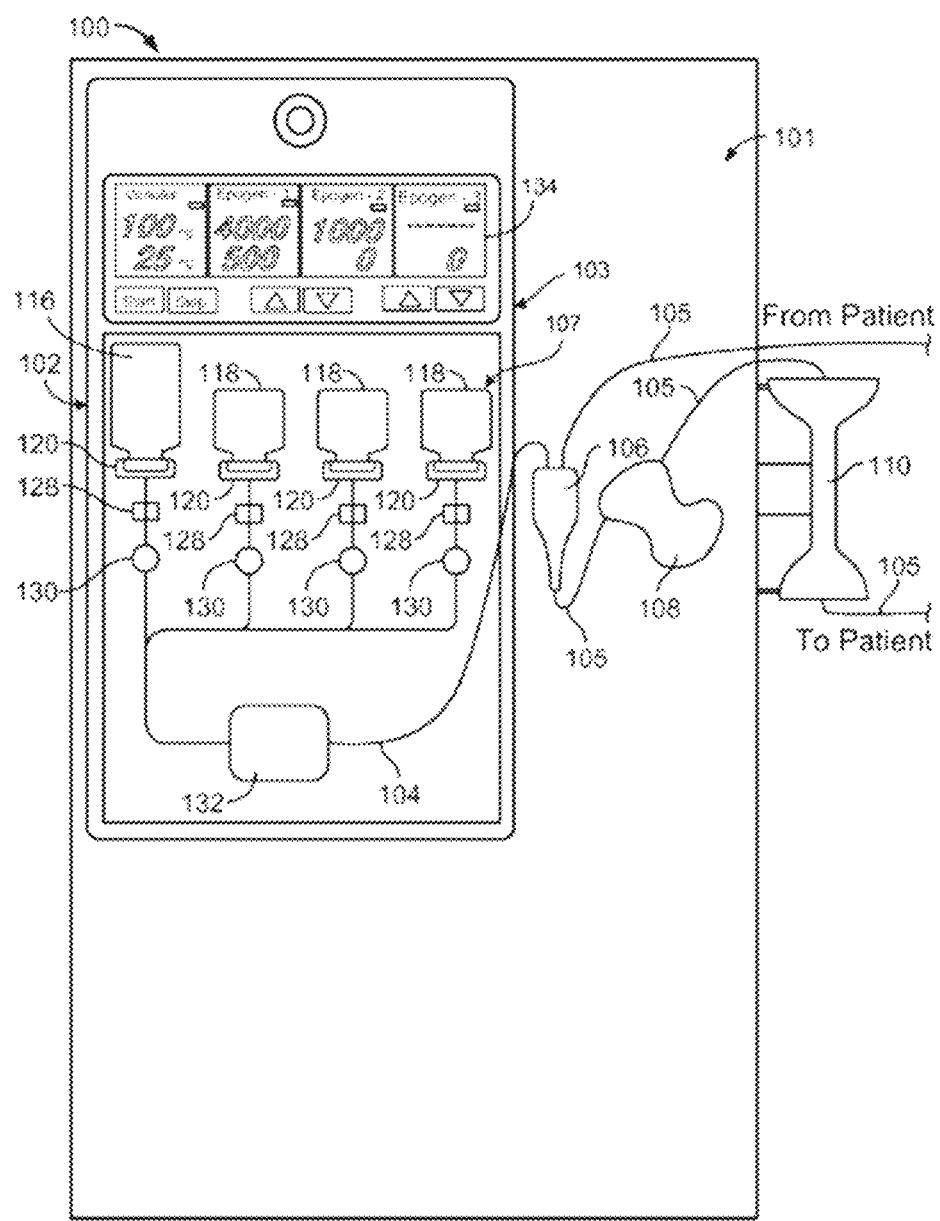
FIG. 16 is a schematic of a hemodialysis machine.
Figure 17:
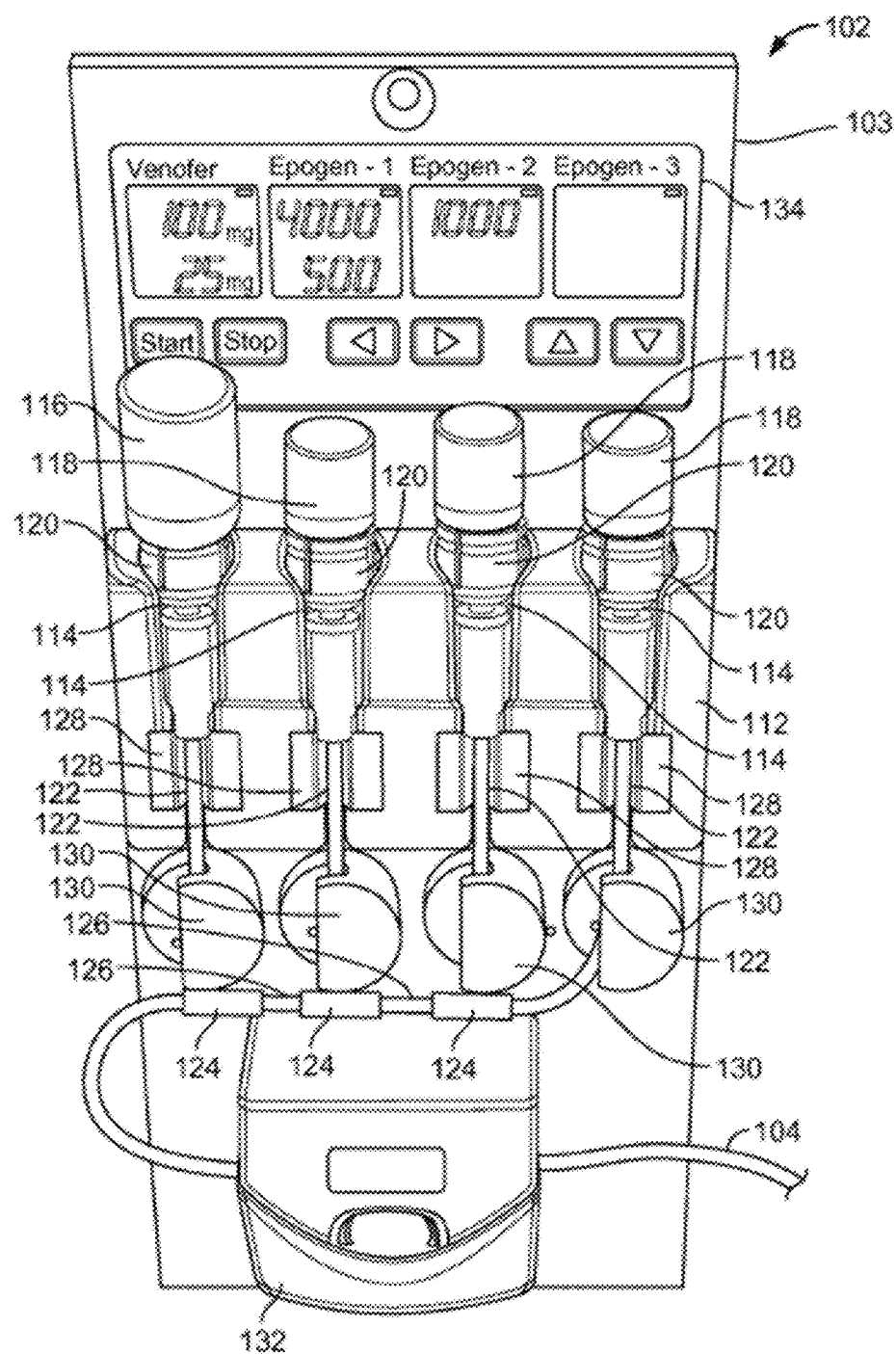
FIG. 17 is a perspective view of a drug delivery device of the hemodialysis machine of FIG. 16.

Referring to FIGS. 1-2 (reproduced herein as FIGS. 16-17) of U.S. Pat. No. 8,382,696 B2 issued to Beiriger et al. on Feb. 26, 2013, which is herein incorporated by reference in its entirely, a hemodialysis system 100 includes a hemodialysis machine 101 that has a drug delivery system 102. The drug delivery system 102 includes a modular drug delivery device 103 and a disposable drug administration fluid line set 109 that is connected to the drug delivery device 103. A drug delivery line 104 of the drug administration fluid line set 109 is fluidly connected to a blood circuit of the hemodialysis system 100. The blood circuit of the hemodialysis system 100 includes, among other things, a blood line set comprising multiple blood lines 105, a drip chamber 106, and a dialyzer 110. A blood pump (e.g., a peristaltic pump) 108 is configured to pump blood through the blood circuit during treatment. The hemodialysis system 100 also includes a dialysate circuit and various other components that, for the sake of simplicity, are not described in detail. During hemodialysis treatment, blood is drawn from the patient and, after passing through the drip chamber 106, is pumped through the dialyzer 110 where toxins are removed from the blood and collected in dialysate passing through the dialyzer. The cleansed blood is then returned to the patient, and the dialysate including the toxins (referred to as "spent dialysate") is disposed of or recycled and reused. As discussed in greater detail below, during the hemodialysis treatment, drugs (such as erythropoiesis stimulating agents, e.g., Epogen®, and iron replacement products, e.g., Venofer®) are also delivered to the drip chamber 106 using the drug delivery system 102. The drugs mix with the patient's blood within the drip chamber 106 and are then delivered to the patient along with the patient's blood.

The modular drug delivery device 103 includes a drug vial holder 112 that defines four channels 114. Each of the channels 114 is designed to hold captive a drug vial 116, 118. The channels 114 can, for example, be recesses that are formed within the drug vial holder 112 and that are sized and shaped to receive only the caps and narrow neck portions of the vials 116, 118 such that the larger body portions of the vials sit above the holder 112. In the illustrated implementation, the vial 116 furthest to the left contains Venofer® and the three vials 118 to the right of the Venofer® vial 116 contain Epogen®. Venofer® (iron sucrose injection, USP) is a sterile, aqueous complex of polynuclear iron (III)-hydroxide in sucrose that is manufactured by American Regent, Inc. Venofer® is indicated in the treatment of iron deficiency anemia in patients undergoing chronic hemodialysis who are receiving supplemental erythropoietin therapy. Epogen® is a drug that stimulates the production of red blood cells and is also commonly used in dialysis patients. Epogen® is manufactured by Amgen, Inc.

The disposable drug administration fluid line set 109 is fluidly connected to each of the vials 116, 118. The drug administration fluid line set 109 includes four drug vial spikes 120 that connect to the vials 116, 118 in a manner to allow the drugs within the vials (e.g., the Venofer® and Epogen®) to flow into feeder lines 122 via the drug vial spikes 120. Each of the feeder lines 122 is attached to a T-connector 124. The T-connectors 124 and associated tubing segments 126 connect the feeder lines 124 to the drug delivery line 104. The drug vial spikes 120 can be formed of one or more relatively rigid medical grade plastics, such as polycarbonate or alphamethylstyrene (AMS), and the various fluid lines can be formed of a more flexible medical grade plastic, such as polyvinylchloride (PVC).

Each of the feeder lines 122, passes through (e.g., is threaded through) a bubble detector 128. The bubble detectors 128 are capable of detecting air bubbles within the feeder lines 122. As a result, each of the bubble detectors 128 can determine whether its associated drug vial 116, 118 is empty during treatment, because air is drawn from the vial 116, 118 into the feeder line 122 when the vial is empty. In some implementations, the bubble detectors 122 are optical detectors. The OPB 350 bubble detector made by Optek can, for example, be used. Other types of optical detectors can alternatively or additionally be used. Similarly, other types of sensors, such as sensors utilizing ultrasound technology can be used as the bubble detectors. Examples of such sensors include the AD8/AD9 Integral Ultrasonic Air-In-Line, Air Bubble Detector and the BD8/BD9 Integral Ultrasonic Air Bubble, Air-In-Line & Liquid Level Detection Sensors (manufactured by Introtek International (Edgewood, N.Y.)). In some implementations, the bubble detector 128 includes a sensor that, in addition to sensing the presence of an air bubble within its associated feeder line 122, can sense the presence of the feeder line itself.

Downstream of the bubble detectors 128, the feeder lines 122 pass through (e.g., are threaded through) occluders 130. Each of the occluders 130 can be used to crimp the portion of the feeder line 122 disposed therein to prevent fluid from passing through the feeder line 122. In some implementations, the occluders 130 are solenoid based rams. Alternatively or additionally, other types of automated occluders can be used. The occluders 130 can be collectively operated in a manner such that only one feeder line 122 is unclamped at any particular time.

The drug delivery line 104 to which each of the feeder lines 122 is fluidly connected passes through (e.g., is threaded through) a peristaltic drug pump 132. The drug pump 132 includes multiple rollers that compress the drug delivery line 104 in a manner to create a "pillow" of fluid (i.e., a "pillow" of air or liquid) that is pinched between two points of the drug delivery line 104 that are compressed by the pump rollers. The rollers are arranged around a circumference of a rotatable frame. As the frame is rotated, the rollers force the "pillow" of fluid through the drug delivery line 104 toward the drip chamber 106. When the pump 132 is being operated and one of the occluders 130 is open (i.e., not clamping its associated feeder line 122), vacuum pressure is applied to the drug vial 116, 118 that is connected to the feeder line 122 associated with the open occluder 130. In certain cases, the initial pressure in the drug vial 116, 118 is equal to the ambient pressure and when all of the drug has been delivered, the ending pressure within the vial is about −10 psi. In other words, the pressure within the drug vial 116, 118 progresses from ambient to −10 psi as the drug is delivered. The pump 132 is configured to generate a vacuum pressure within the drug delivery line 104 and feeder line 122 that exceeds the competing vacuum within the drug vial 116, 118. As a result, the drug is drawn from the vial 116, 118, through the drug vial spike 120, through the feeder line 122, and into the drug delivery line 104.

In some implementations, each channel 114 of the drug vial holder 112 includes a sensor to sense the presence of a vial or drug container. In certain implementations, each drug channel 114 includes a system which identifies the drug vial installed. The drug vial identification system can, for example, include a bar code reader that reads bar codes on the vials. Different types of sensors can alternatively or additionally be used. In some implementations, for example, the vial identification system uses RFID technology. Other examples of suitable sensors include color sensors for sensing the color of color coded drug vials and/or for sensing the color of the drug within the vial, photo sensors (e.g., cameras) that are equipped with text recognition software to read text on the drug vial, capacitive sensors that permit different size vials to be detected, load cells or scales that detect the mass of the vial, and conductivity or electrical impedance sensors that can be used to determine the type of drug within the vial.

The drug delivery device 103 also includes a control unit (e.g., a microprocessor) that can power the various components of the drug delivery device 103. The control unit can receive signals from and send signals to the various components of the drug delivery device 103, including, but not limited to, the bubble detectors 128, the occluders 130, the drug pump 132, the drug vial ID sensors, and other sensors along the drug lines. The control unit can control the various components of the drug delivery device 103 based on information received from these components. For example, the control unit can control the occluders 130 to ensure that only one of the occluders 130 is open at a time. This helps to ensure that drug is pulled from only one of the vials 116, 118 at a time during treatment. The control unit can also determine the volume of drug delivered based on operation data of the drug pump 132 and can control the occluders 130 based on the drug volume determined to have been delivered. For example, upon determining that the prescribed volume of the drug has been delivered, the control unit can close the occluder 130 associated with that drug vial 116, 118 and open the occluder 130 associated with the next drug to be delivered.

The control unit can also control the timing with which the various occluders 130 are opened and closed. For example, after the full contents of a vial have been evacuated, air will be sucked into the feeder line 122 associated with that vial. As the air passes through the feeder line 122, the bubble detector 128 will detect the air and transmit a signal to the control unit indicating that the vial is empty. In response, the control unit can close the occluder 130 associated with the empty vial and open the occluder 130 associated with the vial containing the next drug to be delivered. Upon receiving information from the bubble detectors 128 indicating that all of the vials have been emptied, the control unit can turn off the drug pump 132.

The control unit can also control certain components of the drug delivery device 103 based on signals received from the drug vial ID sensors, which indicate the presence of a vial and/or the identity of the vial contents. Such an arrangement can help to ensure that the correct vials (e.g., the correct number of vials and the vials containing the correct contents) are used for the treatment. Upon receiving signals from the drug vial ID sensors that do not match the inputted treatment information, for example, an alarm (e.g., an audible and/or visual alarm) can be activated. Alternatively or additionally, the drug delivery device 103 can be configured so that treatment cannot be initiated until the sensors detect the correct combination of vials.

The control unit can also be configured to adjust the patient's undesired hematocrit and/or hemoglobin concentration to a value within a desired range at a predetermined time by i) employing a model for predicting the patient's hematocrit and/or hemoglobin concentration at a predetermined time, the model including iron homeostasis, and by ii) operating the blood pump, the at least one ESA pump, and the at least one iron replacement product pump to deliver blood, ESA, and iron replacement product to the drip chamber via the at least one of the blood lines connected to the drip chamber and the at least two of the drug lines connected to the drip chamber, according to an ESA administration regimen predicted to adjust the patient's hematocrit and/or hemoglobin concentration to a value within the desired range at the predetermined time. Delivery of ESA and iron replacement product to the drip chamber can be simultaneous, consecutive, or independent of one another.

The drug delivery device 103 (e.g., the control unit of the drug delivery device 103) is configured to sense if the blood pump 108 of the dialysis machine 101 is running and to pause drug delivery if the blood pump 108 is stopped. This technique prevents 'pooling' of the delivered drug in the drip chamber 106 during treatment.

The drug delivery device 103 further includes a user interface 134 that is connected to the control unit. The user interface 134 includes right/left arrow keys that allow the user to navigate through displays associated with the vials 116, 118. The user interface 134 also includes up/down arrow keys that enable the user to set the desired dosage for each of the vials 116, 118. In addition, the user interface 134 includes start and stop keys that allow the user to start and stop the drug delivery device 103.

Any of various other types of user interfaces can alternatively or additionally be used. In some implementations, the drug delivery device includes a user interface that allows the user to select a drug to infuse from a menu. In certain implementations, the user may confirm that the drug identified by the drug vial ID sensor is correct and/or make appropriate adjustments. The user interface can be used to input and/or monitor various different treatment parameters. Examples of such parameters include drug dosage, drug delivery rate, amount of drug delivered, status of the drug delivery for each drug channel, time, percent complete, percent remaining, time remaining, time delivered, date, patient ID, patient name, alarms, alerts, etc. Such user interfaces can include a color graphical display. In certain implementations, for example, the user interface is color coded according to drug, dosing, or status of drug delivery (e.g., done, running, ready, etc.).

The drug delivery device 103 also includes an alarm and/or alert system to which the control unit of the drug delivery device 103 is connected. The alarm and/or alert system can be configured to emit a visual and/or audio alarm and/or alert. The alarm and/or alert system can further include pre-programmed alarm and/or alert limitations so that when a user modifies any aspect of the system to be outside of the limitations, or the machine itself detects any aspects of the system to be outside of the limitations, the module emits an alarm and/or alert.

Turning back to modeling the life cycle of red blood cells, an erythrocyte (i.e., a red blood cell (RBC)) that reaches an age of 120 days, has traveled approximately 480 kilometers, making about 170,000 circuits, in each cycle enduring osmotic swelling and shrinkage and a number of deformations while passing through capillaries. The accumulated damage to the membrane of the RBC is believed to lead to the destruction of the cell.

About two decades ago it was observed that erythrocytes actually undergo suicidal death. The suicidal death of erythrocytes is called eryptosis. This term was chosen in order to point out the differences from and similarities to apoptosis, the programmed cell death of nucleated cells. Although there exist a number of studies concerning eryptosis, and some parts are understood in great detail, the precise process and mechanisms remain elusive.

Stimulation of eryptosis is governed by a complex signaling network and involves activation of cation channels. (F. Lang, C. Birka, S. Myssina, K. S. Lang, P. A. Lang, V. Tanneur, C. Duranton, T. Wieder, and S. M. Huber. Advances in Experimental Medicine and Biology, 559:211-217, 2004). Shortly before they are phagocytosed by macrophages, which takes place mainly in the spleen, one can observe distinctive cell shrinkage, plasma membrane microvesiculation and an exposure of phosphatidylserine (PS) on the cell surface. These PS-exposing erythrocytes are recognized, engulfed and degraded by macrophages. (D. Bratosin, J. Estaquier, F. Petit, D. Arnoult, B. Quatannens, J. P. Tissier, C. Slomianny, C. Sartiaux, C. Alonso, J. J. Huart, J. Montreuil, and J. C Ameisen. Cell Death Differ, 8(12): 1143-1156, December 2001).

The normal lifespan and senescence can be either accelerated or delayed by environmental signals. Triggers of eryptosis include osmotic shock, oxidative stress, prostaglandin E2, energy depletion, chlorpromazine, aluminum, mercury, etc. Diseases which are associated with an early expression of PS and thus accelerated eryptosis are, for instance, iron deficiency, sepsis, hemolytic uremic syndrome and sickle-cell anemia. See R. F. Zwaal, P. Comfurius, and E. B. Bevers Cellular and molecular life sciences, 62:971-988, 2005. On the other hand eryptosis may be inhibited by erythropoietin, adenosine, catecholamines, nitric oxide and activation of G-kinase. See M. Foller, S. M. Huber, and F. Lang. IUBMB Life, 60:661-668, 2008. Thus, EPO seems not only to increase the number of circulating erythrocytes by preventing apoptosis of progenitor cells but also by prolonging the lifespan of circulating RBC by inhibiting the cation channels. See F. Lang, K. S. Lang, P. A. Lang, S. M. Huber, and T. Wieder Antioxidants & Redox Signaling, 8:1183-1192, 2006; A. B. Schwartz, B. Kelch, L. Terzian, J. Prior, K. E. Kim, E. Pequinot, and B. Kahn. ASAIO transactions, 36:M691M696, 1990. The cation channels are volume-sensitive, and, after activation of the channel, phosphatidylserine asymmetry is reversed and phosphatidylserine is exposed to the outside of the erythrocyte. Binding of erythropoietin to RBC and inhibition of the channels may contribute to an increase in the erythrocyte number during erythropoietin therapy. See S. Myssina, S. M. Huber, C. Birka, P. A. Lang, K. S. Lang, B. Friedrich, T. Risler, T. Wieder, and F. Lang. Journal of American Society of Nephrology, 14:2750-2757, 2003. Surprisingly, it was recently observed that erythrocytes from erythropoietin overexpressing mice die faster ex vivo. See M. Foeller, R. S. Kasinathan, S. Koka, S. M. Huber, B. Schuler, J. Vogel, M. Gassmann, and F. Lang. American Journal of Physiology—Regulatory, Integrative and Comparative Physiology, 293:R1127R1134, 2007. This observation leaves room for discussion. It has been suggested that: "Possibly, erythropoietin stimulates the expression of genes in progenitor cells, which foster eryptosis and thus accelerate erythrocyte death as soon as the erythropoietin concentrations decline." See F. Lang, E. Gulbins, H. Lerche, S. M. Huber, D. S. Kempe, and M. Foller. Eryptosis, Cellular Physiology and Biochemistry, 22:373-380, 2008.

Erythropoiesis and its Regulatory Mechanisms

The daily production rate in a healthy adult totals about $200 \times 10^9$ red blood cells under normal conditions. This number can vary due to varying internal and environmental conditions. The body has to be able to adapt the number of erythrocytes to situations of anemia and/or hypoxia (e.g. after bleeding, due to a shortened RBC lifespan, due to an enhanced eryptosis, . . . ) as well as to situations of excessive red blood cells (e.g., high altitude dwellers descending to sea level).

The production of new erythrocytes takes place in the bone marrow. Undifferentiated stem cells in the bone marrow commit to the erythroid lineage and undergo a series of proliferations and differentiations. The earliest stage of erythroid committed cells are called BFU-Es (Burst-Forming Unit Erythroid). Within a few days the BFU-Es mature to CFU-Es (Colony-Forming Unit Erythroid), then they undergo different stages of erythroblasts, and finally they become reticulocytes. The reticulocytes are released to the blood stream and within 1-2 days they appear as mature erythrocytes. See Williams Hematology. Throughout the description below, the term progenitor cells is used to refer to BFU-E and CFU-E cells, and the term precursor cells is used to subsume proerythroblasts, basophilic erythroblasts, orthochromatophilic erythroblasts and bone marrow reticulocytes.

The primary control of erythropoiesis is governed by the hormone erythropoietin. EPO is produced mainly by peritubular cells in the renal cortex based on a negative feedback mechanism. The kidneys detect the partial pressure of oxygen in blood and react by releasing more EPO if the oxygen content is too low and vice versa. The concentration of EPO affects the number of circulating RBC by determining the number of cells that mature into erythrocytes. Erythropoietin plays a role in the recruitment of stem cells to the erythroid lineage, prevents apoptosis of progenitor cells and affects the maturation velocity of progenitor and precursor cells. Thus, disturbances in oxygen delivery can be adjusted for by an adaptive resetting of the rate of erythropoiesis. Additionally, there exists a physiological process wherein macrophages start to phagocytose young erythrocytes (neocytes), which is called neocytolysis. Neocytolysis seems to be triggered by a drop in the EPO level and helps to regulate situations of excessive red cell mass. See Rice 2001. Further, recent studies suggest that the concentration of EPO in blood influences the clearance of senescent RBCs and that EPO can prolong the lifespan of erythrocytes by inhibiting cation channels.

Progenitor and Precursor Cells

When a stem cell is committed to the erythroid lineage, it develops into an erythrocyte. The number of stem cells which enter the different hematopoietic lineages is determined by interleukines and growth factors. The immature erythrocyte undergoes a number of changes in structure, appearance and its requirements during the process of differentiation and proliferation. BFU-E cells, the first committed erythroid cells, express only a very small number of EPO-receptors (EpoR) and therefore they are almost EPO-independent for their survival. Within a few days they develop into CFU-E cells.

As cells mature to CFU-Es, the number of EpoR on the cell surface increases distinctly, and the cells become absolutely dependent on erythropoietin to prevent them from apoptosis. See H. Wu, X. Liu, R. Jaenisch, and H. F. Lodish. Cell, 83(1):59-67, 1995 (hereinafter "Wu et al."). Under normal conditions, large numbers of generated CFU-E are not surviving. After that very EPO-sensitive phase, the density of EpoRs declines sharply on early erythroblasts and EpoRs almost disappear at the stage of orthochromatophilic erythroblasts. See J. P. Greer, J. Foerster, G. M. Rodgers, F. Paraskevas, B. Glader, D. A. Arber, and R. T. Jr. Means. Wintrobe's Clinical Hematology, volume 1. Lippincott Williams & Wilkins, 12th edition, 2009 (hereinafter "Wintrobe's Clinical Hematology"). Under high levels of EPO, the marrow transit time of precursor cells is shortened, and high EPO levels result in release of still immature reticulocytes, which are referred to as stress reticulocytes. (See Williams Hematology).

One significant difference between progenitor and precursor cells is the synthesis of hemoglobin. Unlike progenitor cells, all types of precursor cells synthesize heme and the increased demand for iron for this process is reflected by a sharp increase in the number of transferrin receptors (TfR) in proerythroblasts (transferrin receptors are the path of iron uptake). TfRs reach their peak in intermediate erythroblasts and decline afterward and mature bone marrow reticulocytes express only a few TfRs (in comparison).

Neocytolysis

The body has to be able to deal with situations of too few circulating erythrocytes as well as with excessive red blood cells. Whereas it is very effective to change the rate of erythropoiesis to adapt the system to situations when red cell numbers are low, this is not an adequate regulatory mechanism in situations of red cell mass excess. This is because a decrease in the rate of erythropoiesis takes relatively long to have a noticeable effect on the number of circulating red blood cells, due to the long lifespan of erythrocytes.

A mere 20 years ago, preventing apoptosis of red cell progenitors had been thought to be the sole regulating effect of EPO. Because this would only allow for a slow adaption in situations of too many RBC, the control of the body of red cell mass would be coarse. A decline in erythropoietin level results in more progenitor cells dying, but a suppression of the hormone has no effect on maturation of erythroid precursors. Thus, no decrement in the erythrocyte production would be observable within one week after EPO has declined. However, studies done on residents at very high altitude who rapidly descended to sea level, showed a decrease in red cell mass of 10-18% in the first 7-10 days. (See Rice 2001). Persons living in hypoxic environments, like high altitude, are normally polycythemic. Thus, their hematocrit is too high under normal conditions and as a consequence the release of EPO is suppressed.

Further investigations of situations where EPO levels are lower than normal (polycythemic high altitude dwellers, anemia of renal failure, human model based on EPO administration then withdrawal), suggest that a suppression of EPO leads to selective hemolysis of young red blood cells. (See Rice 2005). This process is called neocytolysis, to stress the fact that young erythrocytes (i.e., neocytes) are uniquely susceptible. See C.-C. Chang, Y. Chen, K. Modi, O. G. Awar, C. P. Alfrey, and L. Rice. Journal of Investigative Medicine, 57:650-654, 2009; Rice 2005; M. M. Udden, Pickett M. H. Driscoll, T. B., C. S. Leach-Huntoon, and C. P. Alfrey. The Journal of Laboratory and Clinical Medicine, 125:442-449, 1995.

Neocytolysis is initiated by a fall in erythropoietin levels and in Rice 2005 it was shown that, for instance, low doses of EPO, administered to high altitude dwellers on descent, completely abrogated neocytolysis. At the moment it remains unclear whether it is the rate of decline in EPO level or the drop of EPO beneath a certain threshold that acts as a trigger for neocytolysis. See C. P. Alfrey and S. Fishbane. Nephron Clinical Practice, 106:149-156, 2007 (hereinafter "Alfrey et al."); Rice 1999. The current approach to treatment of anemia with ESAs deviates significantly from the normal internal systemic process. Neocytolysis, for instance, contributes to renal anemia. It is precipitated by the pathologic endogenous erythropoietin deficiency of renal disease and the short bursts in EPO concentration followed by sharp declines in serum levels due to administration of the hormone (especially during intravenous (i.v.) administration). It would be desirable to choose dosing schedules such that neocytolysis is minimized or totally prevented. (See Alfrey et al.; Rice 1999). A mathematical model could be very useful to define better ESA administration schemes which stimulate erythropoiesis in a more natural way and abrogate neocytolysis. Better and/or alternative administration schemes can include daily ESA administration, continuous ESA administration (e.g., via a pump), or monthly ESA administration.

Iron and Erythropoiesis

Erythropoiesis is a very complex process and even though erythropoietin is the key regulator, there are other proteins (e.g., interleukins, etc.) and substances (e.g., iron, folic acid, vitamin $B_{12}$, etc.) that are needed for an optimal erythropoiesis. Iron is a very critical factor for an effective production of red blood cells. The metal is indispensable for hemoglobin synthesis and the hemoglobin protein is the actual oxygen transporter in erythrocytes. The molecule makes up about 97% of the dry weight of red blood cells. If the body is not able to provide sufficient iron for the production of erythrocytes, then impaired erythropoiesis will result. (S. Finch, D. Haskins, and C. A. Finch. The Journal of Clinical Investigation, 29:1078-1086, 1950; Williams Hematology). In general, a healthy adult has difficulty providing sufficient iron to support production rates greater than three times basal. Higher rates may be possible when administering EPO and iron and in some diseases, e.g. hemochromatosis. (L. T. Goodnough. Nephrology Dialysis Transplantation, 17:14-18, 2002 (hereinafter "Goodnough 2002"); C. A. Finch. Blood. The Journal of American Society of Hematology, 60(6):1241-1246, 1982) (hereinafter "Finch 1982"). An undersupply of iron additionally leads to an increase in the number of hypochromic RBC. Hypochromic cells (i.e., cells in which the amount of hemoglobin is lower than the normal 26 pg) are small, have a reduced oxygen carrying capacity and are relatively fragile, and thus are likely to die earlier than normochromic erythrocytes. See D. M. Wrighting and N. C. Andrews. Iron Homeostasis and erythropoiesis. Current Topics in Developmental Biology, 82:141-159, 2008 (hereinafter "Wrighting"); A. Loria, L. Sanchez-Medal, R. Lisker, E. De Rodriguez, and J. Labardini. Br J Haematol, 13(3):294-302, May 1967.

Erythroid precursor cells are the most avid consumers of iron in the body. See P. Ponka and C. N. Lok. The International Journal of Biochemistry & Cell Biology, 31:1111-1137, 1999 (hereinafter "Ponka 1999"). The immature erythrocyte has only a few days to synthesize all the hemoglobin which the mature cell contains. Hemoglobin is a metalloprotein. The name refers to its special structure. A hemoglobin molecule consists of four subunits each composed of a globular protein embedding a heme group, and every heme group in turn contains one iron atom. Erythroid cells rely completely on transferrin receptors to take up iron. See R. Y. Chan, C. Seiser, H. M. Schulman, L. C. Kuhn, and P. Ponka. European Journal of Biochemistry, 220:683-692, 1994. Unlike progenitor cells, all types of precursor cells synthesize heme and the increased demand for iron for this process is reflected by a sharp increase in the number of TfR in proerythroblasts. Transferrin receptors reach their peak in intermediate erythroblasts followed by a decrease with further maturation.

In precursor cells, heme is essential for maintaining a "normal" number of TfR. Studies showed that inhibition of heme synthesis strongly inhibited TfR expression. It seems that there exists a positive feedback mechanism in which heme promotes a high rate of transferrin receptor synthesis. A high number of transferrin receptors enhances iron uptake and that in turn keeps hemoglobin synthesis at high levels. See P. Ponka. Blood, 89:1-25, 1997. There is evidence that precursor cells which have a low hemoglobin content are still able to proliferate but do not differentiate and undergo apoptosis. See J. A. Schmidt, J. Marshall, M. J. Hayman, P. Ponka, and H. Beug. Cell, 46:41-51, 1986 (hereinafter "Schmidt").

1. Iron Homeostasis

Iron plays a vital role in metabolic processes in all living organisms, including oxygen transport, DNA synthesis, and electron transport. It is the most important essential trace element and amounts to about 35-45 and 50-55 mg/kg body weight in adult women and men, respectively. See Williams Hematology; Ponka 1999. For a very good overview of iron homeostasis and metabolism, see Crichton and Lieu. Homeostasis is the state of equilibrium (balance between opposing pressures) in the body with respect to various functions and to the chemical compositions of the fluids and tissues. See Steadman's Medical Dictionary, 26.sup.th Edition, Williams & Wilkins, 1995.

Iron is a key component of many cellular enzymes (e.g. oxidases, catalases, peroxidases, cytochromes, etc.). These enzymes are critical in many basic cellular processes, including cell proliferation and differentiation, DNA and RNA synthesis and electron transport. Further, iron, bound in heme, is essential for oxygen transport. Under normal conditions, total body iron burden is very tightly regulated, because excessive iron leads to tissue damage. Once an atom of iron enters the body, it is conserved with remarkable efficiency and can remain in the body for more than ten years. Iron is only lost via loss of cells (epithelial cells, bleeding) and very small amounts are lost via urine and sweat. Unlike other mammals, humans are not able to actively excrete iron. Thus, because of the toxic nature of iron, it is very important to keep absorption and needs well balanced.

Iron is absorbed from dietary sources via the duodenum. The uptake is regulated by the hormone hepcidin. Under normal conditions, the daily absorption of iron amounts to 1-2 mg. In general, in the organism iron is bound to proteins, because free iron results in formation of free radicals and destroys cells. The iron exporter ferroportin is needed to egress the metal from cells (e.g. enterocytes, macrophages, hepatocytes). Ferroportin is not only the effector of cellular iron export but also the receptor of the iron regulating hormone hepcidin. See Williams Hematology.

Much of the iron in the human body can be found in circulating erythrocytes incorporated in hemoglobin (1 ml of packed cells contain about 1 mg of iron). However, most of the iron used for the production of new erythrocytes comes from hemoglobin recycling and not from absorption. When a senescent red cell is phagocytosed, the macrophage internalizes hemoglobin, degrades it, and exports it back out into blood circulation.

Iron is stored in the form of ferritin or hemosiderin, where the latter is more a kind of a long-term storage, because iron within deposits of hemosiderin is very poorly available. Storage sites can be found mainly in the liver, the spleen, and the bone marrow but, for instance, small amounts of hemosiderin can be found in almost any tissue. There are differences between men and women in the amount of iron that is stored (men: about 200-400 mg, women: about 1000 mg,). See C. Crepaldi, A. Brendolan, V. Bordoni, M. R. Carta, V. D. Intini, F. Gastaldon, P. Inguaggiato, and C. Ronco. Hemodialysis International, 7(3):216-221, 2003 (hereinafter "Crepaldi").

Iron is carried around in plasma by a transport protein, which is called transferrin. Transferrin is produced by the liver. Cells which are in need for iron express transferrin receptors, and, after transferrin forms a complex with this receptor, iron is transported into the cell. Transferrin exists in three different forms: iron-free (apotransferrin), one iron (monoferric transferrin) and two iron (differic transferrin) atoms bound. The concentration of iron and the amount of transferrin present in plasma determine the relative abundance of each form. Although iron bound to transferrin amounts to only about 3 mg of total body iron, it is the most important iron pool with the highest rate of turnover, about 30 mg/day. Approximately 80% of this iron is transported to the bone marrow and used by erythroid cells. See Lieu. The amount of transferrin-bound iron is determined by three processes: macrophage iron recycling, iron storage (hepatic) and duodenal iron absorption. See Wrighting.

In the last 15 years, understanding of the regulation of systemic iron homeostasis has changed substantially. The antimicrobial peptide hepcidin (hepatic bactericidal protein), which is secreted by the liver, was identified to be the systemic iron regulator.

Hepcidin inhibits iron transport by binding to the iron exporter ferroportin. Hence, it keeps gut enterocytes from secreting iron into circulation, thereby functionally reducing iron absorption. Further, it prevents iron release from macrophages and blocks the stores as well, by shutting off the means of transport out of cells.

There exist some sensing mechanisms in the liver that gauge the amount of iron needed to support erythropoiesis. Note that hepatocytes in the liver, which secrete hepcidin, also release transferrin into circulation and are one of the major iron storage sites. If the concentration of iron in stores is too low and/or erythropoiesis is increased, then the level of the hormone hepcidin is decreased. Thus, for instance, low hepcidin concentrations are observed in patients with absolute iron-deficiency anemia, or anemias with high erythropoietic activity. See L. T. Goodnough, E. Nemeth, and T. Ganz. Blood, 116:4754-4761, 2010 (hereinafter "Goodnough 2010"). The consequence of a lower hepcidin level is that more iron is taken up via the duodenum and more iron is released from macrophages and from the stores. See Crichton; Fleming. If iron stores are full and/or erythropoiesis is decreased, then more hepcidin is secreted by hepatocytes. As a result of the binding to the iron exporter ferroportin, dietary iron absorption, macrophage iron recycling, and release of iron from stores are partly or fully blocked.

Hepcidin is an acute phase-reactant, and, during inflammation, cytokines stimulate overproduction of hepcidin. Hence, the feedback is altered during inflammation, which is a prominent problem in chronic kidney disease. As a consequence, the body is not able to sufficiently supply developing red blood cells with iron and erythropoiesis is impaired, even though there might be more than enough iron in stores and macrophages, but it is simply not available. This paradoxical situation is called functional iron deficiency, whereas a situation when the iron content of the body is too low (depleted stores) is referred to as absolute iron deficiency.

2. A Mathematical Model for Erythropoiesis Including Iron Homeostasis

For healthy persons, one can assume that erythropoiesis is always sufficiently supplied with iron. This assumption certainly does not hold for some types of anemia and it is not valid for the majority of dialysis patients. Therefore, the model developed in this section incorporates an extensive iron model in order to expand the possible applications to all dialysis patients and to pathologies where an unbalanced iron homeostasis leads to an abnormal erythropoiesis (e.g., anemia of absolute and functional iron deficiency, hemochromatosis, etc.). The incorporation of an iron sub-model and its effects on erythropoiesis has a significant influence on the structure of the population equations.

A reduced reaction of the body to erythropoietin or ESAs is often the result of an insufficient iron availability in the body. A model which gathers the balance between developing precursor cells and iron that can be delivered to the bone marrow for hemoglobin synthesis is needed. Further, iron homeostasis itself is a very complex process. There are complex feedback mechanisms which determine how much iron is shifted around from one place to another in the body and how much is absorbed via dietary input. Unfortunately, most of these feedback mechanisms are not well understood.

A compartmental model for iron is considered and linked to a structured population model which governs the dynamics of the erythroid cell population. For a detailed explanation of amendments and modifications in the population equations for the iron model see Section 2.1. In Section 2.2 the derivation of the iron model is explained. For an overview of how the model developed in this section is organized, see FIG. 9B.

2.1. Population Model.

The structured population equations are designed to link the iron model to the cell population model in a physiologically meaningful way. Five different cell population classes (BFU-E, CFU-E, erythroblasts, marrow reticulocytes, circulating RBCs) are considered. The inclusion of iron makes it necessary to consider some physiological processes in detail. In many applications of structured population equations, the only attribute used to distinguish cells is the cell age. This concept is insufficient for the population class of the precursor cells, where iron is used to synthesize hemoglobin. Here, cells are characterized by their hemoglobin content, and the number of transferrin receptors on the cell membrane, in addition to the cell age. For mature erythrocytes, cell age and hemoglobin content are used as attributes.

The two equations describing the progenitor cell populations (BFU-Es and CFU-Es) are solely structured using cell age. These types of cells do not synthesize hemoglobin and, therefore, they are not among the major consumers of iron. Hence, these two classes can be described by population equations of the form $$\frac{\partial}{\partial t}u(t,\mu) + v(E(t))\frac{\partial}{\partial \mu}u(t,\mu) = (\beta(E(t),\mu) - \alpha(E(t),\mu))u(t,\mu),$$

where $u(t, \mu)$ is the population density of cells at time t with cell age $\mu$. The functions $\beta$ and $\alpha$ describe the rate of division and rate of apoptosis, respectively, of the cells. Further, $\upsilon$ describes the maturation velocity.

Precursor cells are the only erythroid cells that synthesize hemoglobin. In order to introduce these phenomena in the model and to keep track of the amount of hemoglobin the cells are synthesizing, two additional attributes are introduced in addition to cell age:

the number $\tau$ of TfRs per cell
the amount h of hemoglobin each cell is carrying Thus, the general population equation for precursor cells is $$\frac{\partial}{\partial t}u(t,\mu,h,\tau) + \frac{\partial}{\partial \mu}(v_1(t,\mu,h,\tau)u(t,\mu,h,\tau)) +$$

$$\frac{\partial}{\partial h}(v_2(t,\mu,h,\tau)u(t,\mu,h,\tau)) + \frac{\partial}{\partial \tau}(v_3(t,\mu,h,\tau)u(t,\mu,h,\tau)) =$$

$$8\beta(t,\mu,2h,2\tau)u(t,\mu,2h,2\tau) - (\beta(t,\mu,h,\tau) + \sigma(t,\mu,h,\sigma)u(t,\mu,h,\tau).$$

Here $u(t, \mu, h, \tau)$ denotes the population density of the cell population at time t with maturity $\mu$, hemoglobin content h and number of transferrin receptors $\tau$. Further, the functions $\beta$ and $\alpha$ describe the rate of division and rate of apoptosis of the cells. The functions $v_1$, $v_2$, $v_3$ define the rate with which the structural variables $\mu$, h, and $\tau$. are changing, respectively. For a derivation of the partial differential equation (1), see below.

Circulating red blood cells carry hemoglobin but they do not express TfRs for synthesis of the hemoglobin molecule and, therefore, a distinction is made between cells using only cell $\mu$ and hemoglobin content h as structural variables. Hence, the general population equation reads as follows $$\frac{\partial}{\partial t}u(t,\mu,h) + \frac{\partial}{\partial \mu}(v_1(t,\mu,h)u(t,\mu,h)) +$$

$$\frac{\partial}{\partial h}(v_2((t,\mu,h)u(t,\mu,h)) = -\alpha(t,\mu,h)u(t,\mu,h).$$

2.1.1. Progenitor Cells: BFU-E and CFU-E Cells.
Assumptions:

1. The number of stem cells, which commit to the erythroid lineage depends on EPO.
2. Cells normally stay in this stage for 8 days (3 days BFU-E and 5 days CFU-E).
3. The number of transferrin receptors on BFU-E and CFU-E cells is negligible.
4. EPO has no effect on the number of divisions or the rate of apoptosis of BFU-E.
5. The proliferation rate of CFU-E cells is constant.
6. The rate of apoptosis depends strongly on EPO levels.
7. The maturation velocities of BFU-E and CFU-E cells are constant.

Different kinds of growth factors affect the number of stem cells and in vitro studies suggest that high levels of EPO can result in up to 20% more stem cells committing to the erythroid lineage. BFU-E and CFU-E cells express only a very small number of transferrin receptors on the cell membrane and the influence of iron on these cells is neglected. This is not entirely true, because, like all proliferating cells, they need a small amount of iron for division. These amounts are so small compared to the consumption of iron for hemoglobin synthesis that they are neglected. Even in situations of iron deficiency, the assumption is that there is enough iron for cell divisions of progenitor cells available and only hemoglobin synthesis is impaired. Thus, the following population equation is obtained for BFU-E cells:

$$\begin{cases} \frac{\partial}{\partial t}p(t,\mu^p) + \frac{\partial}{\partial \mu^p}p(t,\mu^p) = \beta^p p(t,\mu^p), \\ p(t,0) = S_0(E(t)), \\ p(0,\mu^p) = p_0(\mu^p), \end{cases}$$

where p(t, $\mu^p$) is the population density of the cell class at time t with maturity $\mu^p$, $0 \leq \mu^p \leq \mu_{max}^p = 3$, t>0. Further, $\beta^p$ is the Constant Proliferation Rate (Assumption 4) and $P_0(\mu^p)$ is the population density at t=0. The number $S_0(E(t))$ of cells committing to the erythroid lineage is given by a sigmoidal function, $$S_0(E(t)) = \frac{a_1 - b_1}{1 + e^{-k_1 E(t) + c_1}} + b_1,$$

where E(t) is the EPO concentration at time t and $a_1$, $b_1$, $c_1$ and $k_1$ are positive constants and $a_1 > b_1$. The function $S_0$ increases monotonically with increasing EPO concentration (Assumption 1).

The equation for CFU-E cells is:

$$\begin{cases} \frac{\partial}{\partial t}q(t, \mu^q) + \frac{\partial}{\partial \mu^q}q(t, \mu^q) = (\beta^q - \alpha^q(E(t)))q(t, \mu^q), \\ q(t, \mu_{min}^q) = p(t, \mu_{max}^p), \\ q(0, \mu^q) = q_0(\mu^q), \end{cases}$$

where q(t, $\mu^q$) is the population density of the CFU-E class at time t with maturity $\mu^q$, t>0 and $3 = \mu_{min}^q \leq \mu_{max}^q = 8$. The constant $\beta^q$ describes the division rate (Assumption 4) and $\alpha^q$ (E(t)) the apoptosis rate which depends on the EPO-concentration (Assumption 5). Moreover, the number of cells leaving the BFU-E cell stage and entering the CFU-E cell stage per unit time requires the boundary condition q(t, $\mu_{min}^q$)=p(t, $\mu_{max}^p$). Finally, $q_0(\mu^q)$ is the population density at t=0.

Again, a sigmoidal function is used to describe the dependence of the rate of apoptosis on EPO, $$\alpha^q(E(t)) = \frac{a_2 - b_2}{1 + e^{k_2 E(t) - c_2}} + b_2,$$

where E(t) is the EPO concentration and $a_2$, $b_2$, $c_2$ and $k_2$ are positive constants, $a_2 > b_2$. The function $\alpha^q$ is per definition a monotonically decreasing function. Thus, a higher level of EPO causes more cells to survive.

Finally, because of Assumption 7, it is assumed that cell age equals the actual age of the cells, i.e., $v^p = v^q \equiv 1$, $\forall \geq 0$.

2.1.2. Precursor Cells: Erythroblasts and Marrow Reticulocytes.

Assumptions:

8. The class erythroblasts consists of all cell stages from proerythroblast to orthochromatophilic erythroblast.

9. Cells normally stay in this stage for 6-8 days (5 days erythroblasts and 1-3 days marrow reticulocytes).

10. Under high levels of EPO, so called "stress reticulocytes" are released.

11. All types of precursor cells synthesize hemoglobin.

12. The rate at which the amount of hemoglobin in precursor cells changes, depends on the number of TfRs on the cell surface and the currently available amount of iron.

13. The rate of change of TfRs in precursor cells depends on the cell age and the hemoglobin content of the cell.

14. Cells entering the erythroblast class may be equipped with different numbers of TfRs, i.e., TfRs need not be uniformly distributed among the erythroblast population at time t=0.

15. Hemoglobin is conserved during cell division and a mother cell divides into 2 daughter cells carrying equal amounts of hemoglobin.

16. TfRs are conserved during division and a mother cell divides into 2 daughter cells with equal numbers of TfRs.

17. The maturation velocity of erythroblasts is constant.

18. The proliferation rate of erythroblasts is constant.

19. The rate of apoptosis of erythroblasts depends on cell age and hemoglobin.

20. The maturation velocity of reticulocytes depends on EPO.

21. The rate of apoptosis of reticulocytes depends on cell age and on hemoglobin.

22. Reticulocytes mature but do not proliferate.

23. Iron that enters a precursor cell is incorporated into hemoglobin, i.e., no free iron in the cell is considered.

The number of TfRs increases sharply in the proerythroblasts and reaches its peak in intermediate erythroblasts before declining again (proerythroblasts: 300,000 TfRs/cell; basophilic erythroblasts: 800,000 TfRs/cell; mature reticulocytes: 100,000 TfRs/cell). See Wintrobe's Clinical Hematology. This reflects the increased demand of the cells for iron to synthesize hemoglobin Almost all iron contained in the cells is synthesized to hemoglobin, leaving mature erythrocytes with only a negligible amount of non-heme iron (Assumption 23). Depending on the maturity of cells different numbers of TfRs are to be expected (Assumption 13). Cells that are saturated with hemoglobin reduce the level of receptors. Further, there is evidence that in contrast to other cells, in the precursor cells the number of transferrin receptors is also controlled by a positive feedback involving the amount of already synthesized hemoglobin in the cell. In vitro hemoglobin was shown to be essential for these cells to maintain a normal number of TfRs. See Ponka 1999.

For the erythroblasts population class, the following PDE is obtained $$\begin{cases} \frac{\partial}{\partial t}r(t, \mu^r, h^r, \tau^r) + \frac{\partial}{\partial \mu^r}r(t, \mu^r, h^r, \tau^r) + v_2^r(\tau, a_1(t))\frac{\partial}{\partial h^r}r(t, \mu^r, h^r, \tau^r), \\ + \frac{\partial}{\partial \tau^r}(v_3^r(\mu^r, h^r, \tau^r)r(t, \mu^r, h^r, \tau^r)) = 8\beta u(t, \mu^r, 2h^r, 2\tau^r) - \\ (\beta + \alpha^r(\mu^r, h^r))r(t, \mu^r, h^r, \tau^r), \\ r(t, \mu_{min}^r, 0, \tau^r) = q(t, \mu_{max}) \cdot \eta(\tau^r), \\ r(t, \mu^r, h^r, \tau^r) = 0, \quad \begin{array}{l} \text{if}(\mu^r, h^r, \tau^r)\text{is a boundary point} \\ \text{and } h^r > 0, \end{array} \\ r(0, \mu^r, h^r, \tau^r) = r_0(\mu^r, h^r, \tau^r), \end{cases}$$

where r(t, $\mu^r$, $h^r$, $\tau^r$) is the population density of the erythroblast class at time t with maturity $\mu^r$, hemoglobin content $h^r$ and number of TfRs $\tau^r$, $8 = \mu_{min}^r \leq \mu^r \leq \mu_{max}^r = 13$, $0 \leq h^r \leq h_{max}^r$, $\tau_{min}^r \leq \tau^r \leq \tau_{max}^r$, t>0. The population density at t=0 is given as $r_o(\mu^r, h^r, \tau^r)$. Assumption 17 allows setting $v_\mu^r \equiv 1$, i.e., the cell age of the cell coincides with the actual age of the cell. The contact rate between the TfRs of a cell and transferrin molecules in plasma carrying iron is governed by the law of mass action:

$$d_1 \tau^r(t) a_1(t),$$

where $d_1$ is a rate constant, $\tau^r(t)$ is the number of TfRs on the cell membrane at time t and $a_1(t)$ is the concentration of iron in plasma at time t. Thus, the amount of hemoglobin in a cell evolves according to $$v_2^r(\tau^r, a_1) = d_2 \tau^r a_1, \qquad (2)$$

where $d_2$ is a rate constant that is different from $d_1$ (note that four atoms of iron are needed for one hemoglobin molecule). The change of the number of TfRs on the cell surface is described by a function $v_\tau^r$, depending on the cell age $\mu^r$ and the amount of hemoglobin $h^r$ (Assumption 13). The function $v_\tau^r$ is chosen such that it increases in the beginning and then decreases when the cells are "fully saturated" with hemoglobin.

$$v_3^r(\mu^r, h^r, \tau^r) = a_3\tau^r(h_*^r - b_3(h^r)^2) - \frac{c_3\max(\tau^r, 0)(\mu^r - \mu_{max}^q)}{1 + h^r},$$

where $a_3$, $h_*^r$, $b_3$ and $c_3$ are constants and $\mu^q_{max}$ is the maximal maturity of progenitor cells. The second term assures that cells which progress in maturation, but do not accumulate sufficient iron, lose transferrin receptors. The term $\max(\tau^r, 0)$ is needed to guarantee that the number of TfRs can not become negative. The maximum function is not differentiable, therefore it is approximated by the following function $$s\max(\tau^r) = 0.5\tau^r + 0.5\sqrt{(\tau^r)^2 + 0.01}.$$

The rate of division $\beta^r$ is constant (Assumption 15). Note that the term $8\beta\mu(t, \mu^r, 2h^r, 2\tau^r)$ in the equation arises because of Assumptions 15 and 16. For further details see below. To model the rate of apoptosis $\alpha^r$, a decrease in expression of TfRs is taken into account and leads to a decrease in iron uptake and, thus, less hemoglobin is synthesized. Cells containing small amounts of hemoglobin arrest in differentiation (proliferation is not affected) and this leads to premature cell death. See Schmidt Therefore, it is assumed that $\alpha^r$ depends on $\mu^r$ and $h^r$ (Assumption 19)

$$\alpha^r(\mu^r, h^r) = \frac{b_4(h^{} - h^r)^2}{1 + (\mu^{} - (\mu^r - \mu_{max}^q))^2}, \quad (3)$$

where $b_4$, $h^{}$, $\mu^{} > 0$ are constants. The parameters $h^{}$ and $\mu^{}$ can, for instance, be chosen as $$h^{} = h_{max}^r, \quad \mu^{} = \mu_{max}^r - \mu_{max}^q, \quad (4)$$

where $h^r_{max}$ is the maximal hemoglobin amount of precursor cells and $\mu^r_{max}$ is the maximal maturity of precursor cells.

In principle, the boundary conditions arise as a result of the fact that cells from the precedent class leave the class when they reach the maximum maturity and enter the next population class. Hence, there is a constant flux of cells from the CFU-E class to the erythroblasts class. However, the passage is more complicated because there is a flux from a population class with only one structural variable to a population class with three attributes. Thus, it has to be carefully considered at which points of the boundary the cells are entering. It is useful to keep the physiological situation in mind. Progenitor cells do not synthesize hemoglobin. Hence, there are no cells entering the erythroblasts population class with $h > 0$. On the other hand, it is not natural to apply the same assumption for transferrin receptors. For although the number of TfRs on progenitor cells is neglected, in fact, very mature CFU-E express a number of TfRs. Further, it seems reasonable to assume that at the time when they become proerythroblasts not all cells incorporate exactly the same amount of TfRs on the surface, but that there is some distribution of this attribute among the cells (Assumption 14). Thus, the concept for the boundary includes, that $$\int_{\tau_{min}}^{\tau_{max}} \eta(\tau) d\tau = 1,$$

where, for instance, $\eta(\tau)$ can be chosen such that the structural variable $\tau$ is normally distributed with a certain mean value and variance.

The revisited population equation for marrow reticulocytes reads $$\begin{cases} \frac{\partial}{\partial t}s(t, \mu^s, h^s, \tau^s) + v_1^s(E(t))\frac{\partial}{\partial \mu^s}s(t, \mu^s, h^s, \tau^s) + \\ v_2^s(\tau^s, a_1(t))\frac{\partial}{\partial h^s}s(t, \mu^s, h^s, \tau^s), \\ + \frac{\partial}{\partial \tau^s}(v_3^s(\mu^s, h^s, \tau^s)s(t, \mu^s, h^s, \tau^s)) = -\alpha^s(\mu^s, h^s)s(t, \mu^s, h^s, \tau^s), \\ v^s(E(t))s(t, \mu_{min}^s, h^s, \tau^s) = r(t, \mu_{max}^r, h^r, \tau^r), \\ s(0, \mu^s, h^s, \tau^s) = s_0(\mu^s, h^s, \tau^s), \end{cases}$$

where $s(t, \mu^s, h^s, \tau^s)$ is the population density of the marrow reticulocytes class at time $t$ with maturity $\mu^s$, amount of hemoglobin $h^s$ and number of TfRs $\tau^s$,
$13 = \mu_{min}^s \leq \mu^s \leq \mu_{max}^s = 15$, $h_{min}^s \leq h^s \leq h_{max}^s$, $\tau_{min}^s \leq \tau^s \leq \tau_{max}^s$, $t > 0$. The boundary condition $v^s(E(t))s(t, \mu_{min}^s, h^s, \tau^s) = r(t, \mu_{max}^r, h^r, \tau^r)$ describes the flux of cells leaving the erythroblast class and entering the reticulocytes population class carrying a certain amount of hemoglobin and expressing a certain number of TfRs. Finally, $s_0(\mu^s, h^s, \tau^s)$ is the population density at $t=0$.

A sigmoid function is used to describe the changes in the maturation velocity $v_\mu^s$, $$v_1^s(E(t)) = \frac{a_5 - b_5}{1 + e^{-k_5 E(t) + c_5}} + b_5,$$

where $E(t)$ is the EPO concentration at time $t$ and $a_5$, $b_5$, $c_5$ and $k_5$ are some positive constants with $a_5 > b_5$. The maturation velocity increases with a rising concentration of EPO (Assumption 10). Note, a slower maturation velocity causes the cells to reach the maximum cell age $\mu^s_{max}$ at a later point, whereas a faster maturation velocity shortens the transit time, i.e., the cells reach $\mu_s^{max}$ earlier. The change of the amount of hemoglobin $v_h^s$ in a cell, the development of TfRs $v_\tau^s$ on the cell surface and the rate of apoptosis $\alpha_s$ are described with the same functions as for the erythroblast class, i.e.

$$v_2^s = (\tau, a_1) = v_2^r(\tau, a_1), v_3^s(\mu, h, \tau) = v_3^r(\mu, h) = \alpha^r(\mu, h).$$

Further, $\beta^s = 0$ because of Assumption 22.

So far, Assumption 19 has not been accounted for. The assumption can be applied in the following way: If $E(t) > E^*$ the reticulocyte class is skipped and erythroblasts with maximal maturity directly enter the erythrocytes class.

2.1.3. Erythrocytes.

Assumptions:

24. Erythrocytes and blood reticulocytes are subsumed in one class.

25. Cells mature but do not proliferate.

26. There is a fixed random daily break-down of red blood cells (not to be confused with loss of erythrocytes due to senescence).

27. A drop in EPO concentration beneath a threshold precipitates neocytolysis.

28. Erythrocytes with age between 14-21 days are likely to be affected by neocytolysis.

29. Erythrocytes lose hemoglobin during senescence.

30. The expected life span of normochromic cells in healthy persons is 120 days, but can decrease significantly in uremic patients.

31. Cells in which hemoglobin content drops beneath a certain threshold or which reach the maximum cell age are phagocytosed.

Up to this point, it has been assumed that red blood cells carry approximately the same amount of hemoglobin. This assumption is not valid in many pathologies, different types of anemia, and the majority of dialysis patients, where a wide distribution of corpuscular hemoglobin can be observed. Additionally, it is desirable to account for hemoglobin which is lost during senescence. This loss, which amounts to about 15-20%, is a non-negligible amount of iron that flows back to the macrophages. See S. C. Gifford, J. Derganc, Y. Shevkoplyas, S. S. Yoshida, and M. W. Bitensky, British Journal of Haematology, 135:395-404, 2006; F. L. Willekens, F. H. Bosch, B. Roerdinkholder-Stoelwinder, Y. A. Groenen-Dopp, and J. M. Were, European Journal of Haematology, 58:246-250, 1997; J. M. Werre, F. Willekens, F. H. Bosch, L. D. de Haans, S. G. van der Vegt, A. G. van den Bos, and G. J. Bosman, Cellular and Molecular Biology 50 (2), 139-145, 2004; F. L. Willekens, B. Roerdinkholder-Stoelwinder, Y. A. Groenen-Dopp, H. J. Bos, G. J. Bosman, A. G. van den Bos, A. J. Verkleij, and J. M. Were, Blood, 101:747-751, 2003. Further, the binding of oxygen is pivotal for delivery of oxygen by hemoglobin, and thus a reduction of 15-20% in the hemoglobin mass will have a noticeable impact on the oxygen carrying capacity. Hence, there are several good reasons that suggest including hemoglobin content $h^m$ as a structural variable. Further, the attribute $h^m$ allows one to relatively easily compute the amount of iron which is set free when an erythrocyte is phagocytosed. Moreover, it enables tracking of how much iron is set free daily because of shedding of hemoglobin containing vesicles.

Altogether, the following equation is obtained for erythrocytes:

$$\begin{cases} \frac{\partial}{\partial t} m(t, \mu^m, h^m) + \frac{\partial}{\partial \mu^m} m(t, \mu^m, h^m) + v_2^m(\mu^m) \frac{\partial}{\partial h^m} m(t, \mu^m, h^m), \\ = -\alpha^m(E(t), \mu^m, h^m) m(t, \mu^m), \\ m(t, \mu^m, h_{min}^m) = 0, \\ m(t, 0, h^m) = \begin{cases} v^s((E(t)) \int_{\tau_{min}^s}^{\tau_{max}^s} s(t, \mu_{max}^s, h^s, \tau^s) d\tau^s & \text{for } E \leq E^*, \\ \int_{\tau_{min}^r}^{\tau_{max}^r} r(t, \mu_{max}^r, h^r, \tau^r) d\tau^r & \text{for } E > E^*, \end{cases} \\ m(0, \mu^m, h^m) = m_0(\mu^m, h^m), \end{cases}$$

where the $m(t, \mu^m, h^m)$ is the population density for the erythrocyte class at time t with maturity $\mu^m$ and cell hemoglobin $h^m$, $0 = \mu_{min}^m \leq \mu^m \leq \mu_{max}^m = 120$, $h_{min}^m \leq h^m \leq h_{max}^m$, and $t \geq 0$ and $m_0(\mu^m, h^m)$ is the population density at $t=0$. Moreover, $m(t, 0, h^m)$ is defined by the number of reticulocytes or the number of erythroblasts entering the blood stream carrying a certain amount of hemoglobin $h^m$, respectively. To describe the corpuscular hemoglobin decay, a function $v_k^m$ is used, of the form $$v_2^m(\mu^m) = b_6(\mu^m - \mu_*^m)^2 - c_6,$$

with $b_6, c_6, \mu_*^m > 0$ constant. Choosing appropriate constants $b_6, c_6$ and $\mu_*^m$ allows for a wide range of possible forms of the function $h^m(t)$, with $$\frac{dh^m(t)}{dt} = v_2^m(\mu^m(t)).$$

The mortality rate $\alpha^m(E(t), \mu^m, h^m)$ is the sum of three terms:

1. The rate of cells dying due to senescence, which is assumed to happen when the cell reaches the maximal cell age $\mu_{max}^m$ or the minimal hemoglobin content $h_{min}^m$ (Assumption 30).
2. Cells dying because of random break-down.
3. Cells dying because of neocytolysis.

Altogether, $$\alpha^m(E(t), \mu^m, h^m) = \begin{cases} \gamma^m(\mu^m, h^m) + \min\left(\frac{c_E}{E(t)^{k_E}}, b_E\right) & \text{for } E(t) < \tau_E, \mu_{min}^{m,n} \leq \mu^m \leq \mu_{max}^{m,n}, \\ \gamma^m(\mu^m, h^m) & \text{otherwise} \end{cases},$$

where $b_E, c_E, k_E$ are positive constants, $T_E$ is the threshold beneath which neocytolysis is triggered (Assumption 27). Further, $[\mu_{min}^{m,n}, \mu_{max}^{m,n}] = [14, 21]$ is the age-interval during which cells are effected by neocytolysis (Assumption 28) and $t \geq 0$. Since it is assumed that a cell is phagocytosed when it reaches the maximal cell age $\mu_{max}^m$ or the minimal cell hemoglobin $h_{min}^m$, the mortality rate $\gamma^m(\mu^m, h^m)$ needs to be chosen such that $\gamma^m(\mu^m, h^m) = \alpha_{rand}^m$ for $\mu_{min}^m \leq \mu^m \leq \mu_{max}^m - \delta$, $h_{min}^m + \delta \leq h^m \leq h_{max}^m$ with $\delta > 0$ sufficiently small and $\int_{\mu_{max}^m - \delta}^{\mu_{max}} \int_{h_{min}^m}^{h_{min}^m + \delta} \alpha^m(\mu, h) d\mu dh = \infty$. Here, $\alpha_{rand}^m$ denotes the random breakdown of the cells (Assumption 26). A possible choice for $\gamma^m(\mu^m, h^m)$ is $$\gamma^m(\mu^m, h^m) = \begin{cases} \alpha_r^m & \text{for } \mu^m \in [\mu_{min}^m, \mu_{max}^m - \delta], h^m \in [h_{min}^m + \delta, h_{max}^m], \\ \gamma_\mu^m(\mu^m) \gamma_h^m(h^m) & \text{for } \mu^m \in (\mu_{max}^m - \delta, \mu_{max}^m), h^m \in (h_{min}^m, h_{min}^m + \delta), \\ \infty & \text{for } \mu^m \geq \mu_{max}^m, h^m \leq h_{max}^m, \end{cases}$$

where $$\gamma_\mu^m(\mu^m) = \frac{3\alpha_{rand}^m \delta^2}{(\mu^m)^2 - 2(\mu_{max}^m + \delta)\mu^m + (\mu_{max}^m + 2\delta)\mu_{max}^m},$$

and $$\gamma_h^m(h^m) = \frac{3\delta^2}{(h^m)^2 - 2(h_{min}^m - \delta)h^m + (h_{min}^m - 2\delta)h_{max}^m}.$$

In case of bleeding an additional term $\alpha_{bleed}^m(t)$ needs to be added. What this term looks like depends on whether the bleeding lasts minutes or hours or is prolonged for several days or weeks.

2.1.4. Erythropoietin.

Assumptions:

32. Release of EPO is controlled by a negative feedback mechanism according to the oxygen content.

33. Oxygen carrying capacity is directly proportional to the amount of hemoglobin of circulating red blood cells.

34. The degradation rate of EPO is constant.

35. There is a slight delay in reaction of the EPO production rate to the number of RBCs but this is negligible compared to the duration of development of erythrocytes.

The equation which describes the release of EPO by the kidneys is $$E_{in}^{end}(t) = \frac{a_7 - b_7}{1 + e^{k_7 \tilde{H}b(t) - c_7}} b_7,$$

where $$\tilde{H}b(t) = \frac{Hb(t)}{TBV}$$

is the hemoglobin concentration. Here, TBV is the total blood volume and $Hb(t) = \int_{k_{min}^m}^{k_{max}^m} m(t, \mu^m, h^m) dh^m$ is the total amount of hemoglobin in blood.

Furthermore, $a_7$, $b_7$, $c_7$ and $k_7$ are positive constants with $a_7 > b_7$.

The dynamics of the endogenous EPO concentration $E^{end}(t)$ are described by the following ordinary differential equation:

$$\dot{E}^{end}(t) = \frac{1}{TBV} E_{in}^{end}(t) - c_{deg}^{end} E^{end}(t),$$

where $E^{end}(t)$ is the endogenous EPO concentration, $E_{in}^{end}$ is the amount of EPO released by the kidneys and $c_{deg}^{end}$ describes the degradation rate of endogenous EPO. The change in the concentration $E^{ex}(t)$ of an ESA reads $$\dot{E}^{ex}(t) = \frac{1}{TBV} E_{in}^{ex}(t) - c_{deg}^{ex} E^{ex}(t),$$

where $E_{in}^{ex}(t)$ is the rate at which the artificial hormone is administered $c_{deg}^{ex}$ is the rate with which the exogenous hormone is degraded. In intravenous administration, the total amount of the agent is injected into a vein, within a very short time interval. In this case $E_{in}^{ex}(t)$ can be approximated by $E_0^{ex}(t) \delta_{t_0}(t)$, where $E_0^{ex}$ is the amount of artificial hormone administered and $\delta_{t_0}(t)$ is the Dirac delta impulse located at $t_0$, the time when the administration takes place. In addition, the degradation rate for exogenous EPO $c_{deg}^{ex}$ differs from the one for endogenous EPO and varies according to the kind of ESA administered. The overall concentration of EPO in plasma consists of the naturally produced erythropoietin in the body and the administered ESA $$E(t) = E^{ex}(t) + E^{end}(t).$$

3. The Iron Submodel.

Assumptions:

37. Five iron pools are considered within the body: a plasma pool, iron in precursor cells, iron in erythrocytes, iron in the macrophages and a storage pool.

38. Other iron in the body is ignored.

39. Hepcidin regulates iron homeostasis.

40. Stressed erythropoiesis and depleted stores decrease the amount of hepcidin released into plasma.

41. Large iron stores and inflammation increase hepcidin levels.

42. The amount of iron in plasma is proportional to the amount of transferrin molecules carrying iron. (Free iron is neglected.)

43. No distinction is made between monoferric and diferric transferrin.

44. Iron is lost via loss of cells.

45. Iron lost via urine and sweat is neglected.

Iron is a part of hemoglobin which provides the means of $O_2$ transport to the tissue. The rate at which iron can be released to plasma from existing stores and macrophages may easily limit the rate of iron delivery for hemoglobin synthesis. Therefore, a strong relationship between impaired erythropoiesis and total body iron burden exists. An excellent description of iron homeostasis and its effects can be found in Crichton.

Iron is a substance which is very tightly controlled from the body as iron overload is toxic. Iron homeostasis can be only achieved by the control of absorption because the human body, unlike other mammals, is not able to influence the excretion of iron.

Under normal circumstances the average daily loss of iron is very small (men: 1 mg, women: 2 mg, because of menstruation or pregnancy).

For the iron submodel, five dynamic iron pools are considered within the body: a plasma pool, iron in precursor cells, iron in erythrocytes, iron in the macrophages and a storage pool. Hence, ferritin and hemosiderin stores are combined. Other iron in the body is ignored. The amount of iron lost via urine and sweat is neglected. Thus, in this model, excretion of iron takes place only when cells are lost. On one hand, this can be due to loss of RBCs, i.e., due to external bleeding, and on the other hand there is a daily loss of epithelial cells, which amount for about 1 mg/day. Further, it is assumed that only the precursor cells in the bone marrow uptake iron and ineffective erythropoiesis depends on the amount of iron which can be provided for erythropoiesis. Moreover, the model accounts for the loss of iron from erythrocytes during senescence.

The general form of the compartmental iron model is as follows:

$$\frac{d}{dt} a_1 = k_{41}(H) a_4 + k_{iv,1} a_{iv} + k_{gastro,1}(H) a_{gastro} + k_{51}(H) a_5 - k_{51} a_1 - k_{12} a_1,$$

$$\frac{d}{dt} a_2 = k_{12} a_1 - f_{24} - f_{23},$$

$$\frac{d}{dt} a_3 = f_{23} - f_{34} - f_{3,out},$$

$$\frac{d}{dt} a_4 = f_{24} - f_{34} a_3 - k_{41}(H) a_4 - k_{45} a_4,$$

$$\frac{d}{dt} a_5 = k_{15} a_1 + k_{45} a_4 - k_{51}(H) a_5.$$

Note, in the above equations, the dependence of particular components on t was not explicitly stated to simplify notation. Furthermore, $a_i = 1, \ldots, 5$, denotes the amount of iron in the compartment i and $k_{ij}, i, j = 1, \ldots, 5$ are the transfer rates from compartment i to compartment j, i.e., $k_{ij} a_i$ is the rate at which iron is moving from compartment i to compartment j. Further, $f_{ij}$ denote the rates at which iron is transferred from compartment i into compartment j, when it is not of the simple form $k_{ij} a_i$; $f_{3,out}$ is the amount of iron which is lost by bleeding. Additionally, $a_{iv}$ denotes the amount of iron intravenously administered, whereas $a_{gastro}$ is the amount of iron in the duodenum. Finally, $k_{iv,1}$ and $k_{gastro,1}(H)$ are the corresponding flow rates. The rate $k_{gasto,1}$ can be described by a decreasing sigmoidal function:

$$k_{gastro,1}(H(t)) = \frac{a_8 - b_8}{1 + e^{-k_8 H(t) + c_8}} + b_8,$$

where $a_8$, $b_8$, $c_8$ and $k_8$ are positive constants with $a_8 > b_8$. The function H(t) is the solution of the differential equation (5).

Since the time needed to administer iron is very short compared to other time constants in the system, the following can be taken $$k_{iv,1} a_{iv} = a_{iv,total} \delta_{t_0}.$$

Here $a_{iv,total}$ is the total amount of iron administered and $\delta_{t_0}$ is the Dirac delta function located at $t_0$.

3.1. Hepcidin Feedback.

The regulator of iron homeostasis is hepcidin, a peptide hormone produced by the liver. Hepcidin negatively regulates the availability of iron in plasma by binding to ferroportin on the membranes of iron-exporting cells. Hepcidin binding induces the endocytosis and proteolysis of ferroportin, and thereby decreases the delivery of iron to the plasma. See Nemeth E., Tuttle M. S., Powelson J., Vaughn M. B., Donovan A., Ward D. M., Ganz T., and Kaplan J., Science 306 pp. 2090-2093 (2004). Ferroportin is the iron exporter required for iron egress from iron exporting cells, as for instance, enterocytes and macrophages. Hepcidin acts as a medium to withhold iron from certain invasive bacteria, as they are not able to proliferate under conditions of insufficient iron supply. The dynamics of the hepcidin concentration in plasma is calculated according to (5)

$$\frac{d}{dt} H(t) = \frac{1}{TBV} H_{prod}(t) - c^H_{deg} H(t),$$

where $H_{prod}(t)$ is the rate at which hepcidin, produced by the hepatocytes, is released into the plasma at time t. TBV is the total blood volume, and $c^H_{deg}$ is the rate at which hepcidin is degraded. The production rate $H_{prod}(t)$ of hepcidin is obtained as the result of a feedback loop involving the total precursor cell population, the amount of iron stored and the state of inflammation of the patient $$H_{prod}(t) = f(U(t), a_5(t), i(t)).$$

Here $$U(t) = \int_{\mu^r_{min}}^{\mu^r_{max}} \int_{h^r_{min}}^{h^r_{max}} \int_{\tau^r_{min}}^{\tau^r_{max}} r(t, \mu^r, h^r) d\mu^r dh^r d\tau^r + \int_{\mu^s_{min}}^{\mu^s_{max}} \int_{h^s_{min}}^{h^s_{max}} \int_{\tau^s_{min}}^{\tau^s_{max}} s(t, \mu^s, h^s) d\mu^s dh^s d\tau^s,$$

where U(t) describes the total precursor cell population (erythroblasts+reticulocytes). Further, $a_5(t)$ is the amount of iron stored and i(t) is the inflammation status at time t. The feedback is modeled using a monotonically increasing sigmoidal function $$H_{prod}(t) = \frac{a_H - b_H}{1 + e^{k_H C(t) + c_H}} + b_H,$$

where $a_H$, $b_H$, $c_H$ and $k_H$ are positive constants with $a_H > b_H$. The function $$C(t) = -c_U U(t) + c_{a_5} a_5(t) + c_i i(t).$$

is an auxiliary equation that increases if storage amount or inflammation status rises, and decreases when more RBCs are produced. Here, $c_U$, $c_{a_5}$ and $c_i$ are positive constants.

3.2. Detailed Description of the Iron Compartments.

3.2.1. Plasma (Compartment 1).

The rate at which iron enters erythroid cells at time t is given by $$d_0 a_1(t) \left( \int_{\mu^r_{min}}^{\mu^r_{max}} \int_{h^r_{min}}^{h^r_{max}} \int_{\tau^r_{min}}^{\tau^r_{max}} \tau^r r(t, \mu^r, \tau^r, h^r) d\mu^r dh^r d\tau^r + \int_{\mu^s_{min}}^{\mu^s_{max}} \int_{h^s_{min}}^{h^s_{max}} \int_{\tau^s_{min}}^{\tau^s_{max}} \tau^s s(t, \mu^s, \tau^s, h^s) d\mu^s dh^s d\tau^s \right),$$

where $r(t, \mu^r, \tau^r, h^r)$ and $s(t, \mu^s, \tau^s, h^s)$ denote the population densities of hemoglobin synthesizing cells, erythroblasts and reticulocytes, respectively. At the same time this is the rate at which iron leaves the plasma compartment and enters the precursor cell compartment.

Only a very small amount of iron can be found in this pool (about 3 mg; ≤1%) bound to transferrin, but it is a very important compartment because of its rapid turnover rate. See Finch 1982. Iron normally turns over at least 10 times each day. See Williams Hematology. Inflow into the plasma compartment comes from macrophages, the storage pool, iron absorbed through the duodenum and via intravenously administered iron. Outflow leaves the plasma compartment to the precursor cells and the storage compartment. The flow rates $k_{41}$, $k_{gastro,1}$ and $k_{51}$ are dependent on the hepcidin concentration H(t) at time t. They decrease when the hepcidin level rises and vice versa. Inflammation and full iron stores increase the release of hepcidin from the hepatocytes in the liver, whereas a stressed erythropoiesis and depleted stores suppress the production of hepcidin. The outflow to the precursor cell compartment $k_{12} a_1$ is altered by the amount of iron needed from the cells to synthesize hemoglobin. As erythroid cells are only able to take up iron through transferrin receptors, their need for iron can be associated with the number of receptors expressed on precursor cells. Thus, the rate $k_{12}$ is given by $$k_{12} = d_0 \left( \int_{\mu^r_{min}}^{\mu^r_{max}} \int_{h^r_{min}}^{h^r_{max}} \int_{\tau^r_{min}}^{\tau^r_{max}} \tau^r r(t, \mu^r, h^r) d\mu^r dh^r d\tau^r + \int_{\mu^s_{min}}^{\mu^s_{max}} \int_{h^s_{min}}^{h^s_{max}} \int_{\tau^s_{min}}^{\tau^s_{max}} \tau^s s(t, \mu^s, h^s) d\mu^s dh^s d\tau^s \right).$$

For an explanation of the various terms see the statements concerning erythroblasts in Subsection 2.1.2. Hence, the change of amount of iron in the plasma compartment is $$\frac{d}{dt} a_1(t) =$$

$$k_{41}(H(t)) a_4(t) + a_{iv,total}(t) \delta_{t_0}(t) + k_{gastro,1}(H(t)) a_{gastro}(t) + k_{51}(H(t)) a_5(t) -$$

$$k_{15} a_1(t) - d_0 \left( \int_{\mu^r_{min}}^{\mu^r_{max}} \int_{h^r_{min}}^{h^r_{max}} \int_{\tau^r_{min}}^{\tau^r_{max}} \tau^r r(t, \mu^r, h^r) d\mu^r dh^r d\tau^r + \right.$$

$$\left. \int_{\mu_{min}^s}^{\mu_{max}^s} \int_{h_{min}^s}^{h_{max}^s} \int_{\tau_{min}^s}^{\tau_{max}^s} \tau^s s(t, \mu^s, h^s) d\mu^s dh^s d\tau^s \right) a_1(t)$$

The transfer rate $k_{41}(H(t))$ and $k_{51}(H(t))$ can be described by monotonically decreasing sigmoidal functions $$k_{41}(H(t)) = \frac{a_9 - b_9}{1 + e^{-k_9 H(t) + c_9}} + b_9, \quad (6)$$

and $$k_{51}(H(t)) = \frac{a_{10} - b_{10}}{1 + e^{-k_{10} H(t) + c_{10}}} + b_{10}, \quad (7)$$

respectively. The parameters $a_9$, $b_9$, $c_9$, $k_9$, $a_{10}$, $b_{10}$, $c_{10}$ and $k_{10}$ are positive constants with $a_9 > b_9$ and $a_{10} > b_{10}$. The hepcidin level $H(t)$ at time t is determined by equation (5).

3.2.2. Precursor Cells (Compartment 2).

Inflow into the precursor cell compartment comes from plasma. One outflow of this compartment leaves to the erythrocytes compartment and describes the amount of hemoglobin carried from reticulocytes, which enter the blood stream. Thus, the flow $f_{23}(\bullet)$ from compartment 2 to compartment 3, is defined by the cells that leave the bone marrow and the amount of hemoglobin these cells are carrying. These quantities can be calculated from the population model and $$k_{23} a_2 = f_{23}(v^s(E(t))s(t, \mu_{max}^s, \tau^s), h^s(\mu_{max}^s)),$$

where $v^s(E(t))s(t, \mu_{max}^s, \tau^s)$ determines how many cells are leaving the bone marrow at a certain time t and the distribution function $h^s(\mu_{max}^s)$ at the maximum maturity level $\mu_{max}^s$ indicates how much hemoglobin they carry. Here $v^s(E(t))$ is the maturation velocity of reticulocytes depending on EPO, $s(t, \mu_{max}^s, \tau^s)$ is the density of reticulocyte population with maximal maturity $\mu_{max}^s$, and $\tau^s \in [\tau_{min}^s, \tau_{max}^s]$ is the number of transferrin receptors at time t. The hemoglobin distribution function $h^s(\mu_{max}^s)$ arises as a result of the population model, in particular the precursor cell population part.

The second outflow of this compartment leaves to the macrophages and is defined by the precursor cells that die. Hence, the flow from compartment 2 to compartment 4 is defined by the amount of iron that dying cells carry, i.e., $$k_{24} a_4 = \int_{\mu_{min}^r}^{\mu_{max}^r} \int_{h_{min}^r}^{h_{max}^r} \int_{\tau_{min}^r}^{\tau_{max}^r} h^r \alpha^r(\mu^r, h^r) r(t, \mu^r, h^r) d\mu^r dh^r d\tau^r + \quad (8)$$

$$\int_{\mu_{min}^s}^{\mu_{max}^s} \int_{h_{min}^s}^{h_{max}^s} \int_{\tau_{min}^s}^{\tau_{max}^s} h^s \alpha^s(\mu^s, h^s) s(t, \mu^s, h^s) d\mu^s dh^s d\tau^s,$$

where $r(t, \mu^r, \tau^r)$ and $s(t, \mu^s, \tau^s)$ are the densities of the two precursor cell populations. Further, $\mu^i \in [\mu_{min}^i, \mu_{max}^i]$ denotes the maturity, $h^i \in [h_{min}^i, h_{max}^i]$ denotes the amount of hemoglobin carried by a cell and $\tau^i \in [\tau_{min}^i, \tau_{max}^i]$ denotes the number of transferrin receptors for I=r,s. The function $\alpha^i(\mu^i, h^i)$, i=r,s describes the mortality rate of precursor cells, where $\alpha^r = \alpha^s$ is determined by equations (3) and (4).

Altogether the change of amount of iron in the iron-precursors compartment is given by $$\frac{d}{dt} a_2(t) = d_0 \left( \int_{\mu_{min}^r}^{\mu_{max}^r} \int_{h_{min}^r}^{h_{max}^r} \int_{\tau_{min}^r}^{\tau_{max}^r} \tau^r r(t, \mu^r, h^r) d\mu^r dh^r d\tau^r + \right.$$

$$\left. \int_{\mu_{min}^s}^{\mu_{max}^s} \int_{h_{min}^s}^{h_{max}^s} \int_{\tau_{min}^s}^{\tau_{max}^s} \tau^s s(t, \mu^s, h^s) d\mu^s dh^s d\tau^s \right) a_1(t) -$$

$$f_{23}(v^s(E(t))s(t, \mu_{max}^s, \tau^s), h^s(\mu_{max}^s)) -$$

$$\int_{\mu_{min}^r}^{\mu_{max}^r} \int_{h_{min}^r}^{h_{max}^r} \int_{\tau_{min}^r}^{\tau_{max}^r} h^r \alpha^r(\mu^r, h^r) r(t, \mu^r, h^r) d\mu^r dh^r d\tau^r +$$

$$\int_{\mu_{min}^s}^{\mu_{max}^s} \int_{h_{min}^s}^{h_{max}^s} \int_{\tau_{min}^s}^{\tau_{max}^s} h^s \alpha^s(\mu^s, h^s) s(t, \mu^s, h^s) d\mu^s dh^s d\tau^s.$$

Note that it is not necessary to determine the function $f_{23}$, because there is no need to explicitly observe the rate of change of the precursor cell compartment. The amount of iron $a_2(t)$ in this compartment at time t can be directly computed from the population classes. It is defined by the total number of precursor cells and the amount of hemoglobin they carry:

$$a_2(t) = \int_{\mu_{min}^r}^{\mu_{max}^r} \int_{h_{min}^r}^{h_{max}^r} \int_{\tau_{min}^r}^{\tau_{max}^r} h^r r(t, \mu^r, h^r) d\mu^r dh^r d\tau^r +$$

$$\int_{\mu_{min}^s}^{\mu_{max}^s} \int_{h_{min}^s}^{h_{max}^s} \int_{\tau_{min}^s}^{\tau_{max}^s} h^s s(t, \mu^s, h^s) d\mu^s dh^s d\tau^s.$$

However, it is important to know the flux of hemoglobin to the macrophage compartment which arises from dying cells, because this flux (see equation (8)) is a source term in the macrophage compartment.

3.2.3. Erythrocytes (Compartment 3).

Inflow into the erythrocytes compartment comes from the precursor cell compartment, and iron leaves the compartment to the macrophages compartment (phagocytosis of senescent cells, random break-down of cells and neocytolysis, shedding of hemoglobin containing vesicles)

$$k_{34} a_3 = \int_{\mu_{min}^m}^{\mu_{max}^m} \int_{h_{min}^m}^{h_{max}^m} h^m \alpha^m(E(t), \mu^m, h^m) m(t, \mu^m, h^m) d\mu^m dh^m + \quad (9)$$

$$\int_{\mu_{min}^m}^{\mu_{max}^m} \int_{h_{min}^m}^{h_{max}^m} v_2^m(\mu^m) m(t, \mu^m, h^m) d\mu^m dh^m,$$

or is excreted via bleeding $$k_{3,out} a_3 = \int_{\mu_{min}^m}^{\mu_{max}^m} \int_{h_{min}^m}^{h_{max}^m} h^m \alpha_{bleed}^m(t) m(t, \mu^m, h^m) d\mu^m dh^m.$$

Here $\alpha^m$ denotes the mortality rate of erythrocytes due to phagocytosis of senescent cells, random break-down of cells and neocytolysis. Furthermore, $h^m$ is the amount of hemoglobin carried by a cell, $m(t, \mu^m, h^m)$ is the population density of erythrocytes with cell age $\mu^m$ and cellular hemoglobin $h^m$ at time t and $\alpha^m_{bleed}(t)$ is the rate with which RBCs are lost due to bleeding. Thus, the change of amount of iron in the erythrocyte compartment is $$\frac{d}{dt}a_3(t) = f_{23}(v^s(E(t))s(t, \mu^s_{max}, \tau^s), h^s(\mu^s_{max})) -$$

$$\int_{\mu^m_{min}}^{\mu^m_{max}} \int_{h^m_{min}}^{h^m_{max}} h^m \alpha^m_{bleed}(t) m(t, \mu^m, h^m) d\mu^m dh^m -$$

$$\int_{\mu^m_{min}}^{\mu^m_{max}} \int_{h^m_{min}}^{h^m_{max}} h^m \alpha^m(E(t), \mu^m, h^m) m(t, \mu^m, h^m) d\mu^m dh^m -$$

$$\int_{\mu^m_{min}}^{\mu^m_{max}} \int_{h^m_{min}}^{h^m_{max}} v_2^m(\mu^m) m(t, \mu^m, h^m) d\mu^m dh^m.$$

Similar to compartment 2, it is not necessary to observe the rate of change of the erythrocyte cell compartment to compute the amount of iron $a_3(t)$ at time t. The quantity $a_3(t)$ can be directly computed from the population class and is defined by the total number of circulating red blood cells and the amount of hemoglobin they carry:

$$a_3(t) = \int_{\mu^m_{min}}^{\mu^m_{max}} \int_{h^m_{min}}^{h^m_{max}} h^m m(t, \mu^m, h^m) dh^m d\mu^m.$$

However, the term $k_{34}a_3(t)$ needs to be known explicitly (see equation (9)). This flux, which is the rate of hemoglobin released by erythrocytes, appears as a source term in the macrophage compartment.

3.2.4. Macrophages (Compartment 4).

Inflow into the macrophages compartment comes from the erythrocytes compartment (erythrocytes phagocytosed by macrophages, iron set free by random break-down of RBCs and shedding of hemoglobin containing vesicles) and the precursor cells compartment. Outflow of this compartment leaves to the plasma and to the storage compartment. Therefore, the change of iron in the compartment is $$\frac{d}{dt}a_4(t) = \int_{\mu^m_{min}}^{\mu^m_{max}} \int_{h^m_{min}}^{h^m_{max}} h^m \alpha^m(E(t), \mu^m, h^m) m(t, \mu^m, h^m) d\mu^m dh^m +$$

$$\int_{\mu^m_{min}}^{\mu^m_{max}} \int_{h^m_{min}}^{h^m_{max}} v_2^m(\mu^m) h^m m(t, \mu^m, h^m) d\mu^m dh^m +$$

$$\int_{\mu^r_{min}}^{\mu^r_{max}} \int_{h^r_{min}}^{h^r_{max}} \int_{\tau^r_{min}}^{\tau^r_{max}} h^r r(t, \mu^r, h^r) d\mu^r dh^r d\tau^r +$$

-continued $$\int_{\mu^s_{min}}^{\mu^s_{max}} \int_{h^s_{min}}^{h^s_{max}} \int_{\tau^s_{min}}^{\tau^s_{max}} h^s s(t, \mu^s, h^s) d\mu^s dh^s d\tau^s - k_{41}(H(t))a_4(t) - k_{45}a_4(t),$$

where $k_{41}(H(t))$ is given by equation (6).

3.2.5. Storage (Compartment 5.)

Inflow into the storage compartment comes from the plasma and the macrophages compartment and iron leaves this compartment to the plasma compartment. Hence, the change of iron in the storage compartment is $$\frac{d}{dt}a_5(t) = k_{15}a_1(t) + k_{45}a_4(t) - k_{51}(H(t))a_5(t),$$

where $k_{51}(H(t))$ is given in equation (7).

The iron submodel can be applied independently of erythropoiesis to a variety of iron disorders, such as true iron deficiency states (e.g., bleeding, malabsorption), functional iron deficiencies (e.g., anemias of chronic disease, usually with chronic inflammatory disorders or malignancies), or iron overload disorders (e.g., all forms of hemochromatosis, iron intoxication, polytransfusions of blood, chronic hepatopathies, and hyper plastic erythroid disorders such as thalassemias).

4. A Complete Listing of the Equations for the Mathematical Model.

The model consists of the following structured population equations:

$$\frac{\partial}{\partial t}p(t, \mu^p) + \frac{\partial}{\partial \mu^p}p(t, \mu^p) = \beta^p p(t, \mu^p),$$

$$\frac{\partial}{\partial t}q(t, \mu^q) + \frac{\partial}{\partial \mu^q}q(t, \mu^q) = (\beta^q - \alpha^q(E(t))q(t, \mu^q)),$$

$$\frac{\partial}{\partial t}r(t, \mu^r, h^r, \tau^r) + \frac{\partial}{\partial \mu^r}r(t, \mu^r, h^r, \tau^r) + v_2^r(\tau, a_1(t))\frac{\partial}{\partial h^r}r(t, \mu^r, h^r, \tau^r),$$

$$+ \frac{\partial}{\partial \tau^r}(v_3^r(\mu^r, h^r, \tau^r)r(t, \mu^r, h^r, \tau^r) =$$

$$8\beta u(t, \mu^r, 2h^r, 2\tau^r) - (\beta + \alpha^r(\mu^r, h^r))r(t, \mu^r, h^r, \tau^r),$$

$$\frac{\partial}{\partial t}s(t, \mu^s, h^s, \tau^s) + v_1^s(E(t))\frac{\partial}{\partial \mu^s}s(t, \mu^r, h^r, \tau^r) +$$

$$v_2^s(\tau^s, a_1(t))\frac{\partial}{\partial h^s}s(t, \mu^s, h^s, \tau^s) + \frac{d}{d\tau^s}(v_3^s(\mu^s, h^s, \tau^r)s(t, \mu^s, h^s \tau^s)) =$$

$$-\alpha^s(\mu^s, h^s)s(t, \mu^s, h^s, \tau^s),$$

$$\frac{\partial}{\partial t}m(t, \mu^m, h^m) + \frac{\partial}{\partial \mu^m}m(t, \mu^m, h^m) + v_2^s(\mu^m)\frac{\partial}{\partial h^m}m(t, \mu^m, h^m) =$$

$$-\alpha^m(E(t), \mu^m h^m)m(t, \mu^m),$$

$$\frac{d}{dt}E^{end}(t) = \frac{1}{TBV}E_{in}^{end}(t) - c_{deg}^{end}E^{end}(t),$$

$$\frac{d}{dt}E^{ex}(t) = \frac{1}{TBV}E_{in}^{ex}(t) - c_{deg}^{ex}E^{ex}(t).$$

Further, the iron model can be described as follows:

$$\frac{d}{dt}a_1(t) = k_{41}\big(H(t)a_4 + a_{iv,total}(t)\delta_{t_0}(t) + k_{gastro,1}(H(t))a_{gastro}(t) + k_{51}$$

$$\big(H(t)a_5(t) - k_{15}a_1(t) - d_0\Bigg(\int_{\mu^r_{min}}^{\mu^r_{max}}\int_{h^r_{min}}^{h^r_{max}}\int_{\tau^r_{min}}^{\tau^r_{max}} \tau^r r(t,\mu^r,h^r)d\mu^r dh^r d\tau^r +$$

$$\int_{\mu^s_{min}}^{\mu^s_{max}}\int_{h^s_{min}}^{h^s_{max}}\int_{\tau^s_{min}}^{\tau^s_{max}} \tau^s s(t,\mu^s,h^s)d\mu^s dh^s d\tau^s\Bigg)a_1(t).$$

$$a_2(t) = \int_{\mu^r_{min}}^{\mu^r_{max}}\int_{h^r_{min}}^{h^r_{max}}\int_{\tau^r_{min}}^{\tau^r_{max}} h^r r(t,\mu^r,h^r)d\mu^r dh^r d\tau^r +$$

$$\int_{\mu^s_{min}}^{\mu^s_{max}}\int_{h^s_{min}}^{h^s_{max}}\int_{\tau^s_{min}}^{\tau^s_{max}} h^s r(t,\mu^s,h^s)d\mu^s dh^s d\tau^s.$$

$$a_3(t) = \int_{\mu^m_{min}}^{\mu^m_{max}}\int_{h^m_{min}}^{h^m_{max}} h^m m(t,\mu^m,h^m)dh^m d\mu^m.$$

$$\frac{d}{dt}a_4(t) = \int_{\mu^m_{min}}^{\mu^m_{max}}\int_{h^m_{min}}^{h^m_{max}} h^m \alpha^m(E(t),\mu^m,h^m)m(t,\mu^m,h^m)d\mu^m dh^m +$$

$$\int_{\mu^m_{min}}^{\mu^m_{max}}\int_{h^m_{min}}^{h^m_{max}} v_2^m(\mu^m)h^m m(t,\mu^m,h^m)d\mu^m dh^m +$$

$$\int_{\mu^r_{min}}^{\mu^r_{max}}\int_{h^r_{min}}^{h^r_{max}}\int_{\tau^r_{min}}^{\tau^r_{max}} h^r r(t,\mu^r,h^r)d\mu^r dh^r d\tau^r +$$

$$\int_{\mu^s_{min}}^{\mu^s_{max}}\int_{h^s_{min}}^{h^s_{max}}\int_{\tau^s_{min}}^{\tau^s_{max}} h^s s(t,\mu^s,h^s)d\mu^s dh^s d\tau^s - k_{41}(H(t))a_4(t) - k_{45}a_4(t),$$

$$\frac{d}{dt}a_5(t) = k_{15}a_1(t) + k_{45}a_4(t) - k_{51}(H(t))a_5(t),$$

$$\frac{d}{dt}H(t) = \frac{1}{TBV}H_{prod}(t) - c^H_{deg}H(t).$$

The boundary conditions are $$p(t,0) = S_0(E(t)),$$

$$q(t,\mu^q_{min}) = p(t,\mu^p_{min}),$$

$$r(t,\mu^r_{min},0,\tau^r) = q(t,\mu_{max})\eta(\tau^r),$$

$r(t,\mu^r,h^r,\tau^r) = 0$, if $(\mu^r,h^r,\tau^r)$ is a boundary point and $h^r > 0$, $$v^s(E(t))s(t,\mu^s_{min},h^s,\tau^s) = r(t,\mu^r_{max},h^r,\tau^r),$$

$$m(t,\mu^m,h^m_{min}) = 0$$

$$m(t,0,h^m) = \begin{cases} v^s(E(t))\int_{\tau^s_{min}}^{\tau^s_{max}} s(t,\mu^s_{max},h^s,\tau^s)d\tau^s & \text{for } E(t) \le E^*, \\ \int_{\tau^r_{min}}^{\tau^r_{max}} r(t,\mu^r_{max},h^r,\tau^r)d\tau^r & \text{for } E(t) > E^*, \end{cases}$$

and the initial values are given by $$p(0,\mu^p) = p_0(\mu^p),$$

$$q(0,\mu^q) = q_0(\mu^q),$$

$$r(0,\mu^r,h^r,\tau^r) = r_0(\mu^r,h^r,\tau^r),$$

$$s(0,\mu^s,h^s,\tau^s) = s_0(\mu^s,h^s,\tau^s),$$

$$m(0,\mu^m,h^m) = m_0(\mu^m,h^m),$$

$$E^{end}(0) = E_0^{end},$$

$$E^{ex}(0) = E_0^{ex},$$

$$a_1(0) = a_{1,0},$$

$$a_2(0) = a_{2,0},$$

$$a_3(0) = a_{3,0},$$

$$a_4(0) = a_{4,0},$$

$$a_5(0) = a_{5,0},$$

$$H(0) = H_0.$$

Moreover, there are number of auxiliary equations for the cell population model $$S_0(E(t)) = \frac{a_1 - b_1}{1 + e^{-k_1 E(t) + c_1}} + b_1,$$

$$\alpha^q(E(t)) = \frac{a_2 - b_2}{1 + e^{-k_2 E(t) + c_2}} + b_2,$$

$$v_2^r(\tau^r,a_1) = d_2\tau^r a_1,$$

$$v_3^r(\mu^r,h^r,\tau^r) = a_3\tau^r(h^r_* - b_3(h^r)^2) - \frac{c_3\max(\tau^r,0)(\mu^r - \mu^q_{max})}{(1 + h^r)},$$

$$\alpha^r(\mu^r,h^r) = \frac{b_4(h^{} - h^r)^2}{1 + (\mu^{} - (\mu^r - \mu^q_{max}))^2},$$

$$\int_{\tau^r_{min}}^{\tau^r_{max}} \eta(\tau)d\tau = 1,$$

$$v_1^s(E(t)) = \frac{a_5 - b_5}{1 + e^{-k_5 E(t) + c_5}} + b_5,$$

$$v_2^s(\tau^s,a_1) = d_2\tau^s a_1,$$

$$v_3^s(\mu^s,h^s,\tau^s) = a_3\tau^s(h^s_* - b_3(h^s)^2) - \frac{c_3\max(\tau^s,0)(\mu^s - \mu^r_{max})}{(1 + h^s)},$$

$$\alpha^s(\mu^s,h^s) = \frac{b_4(h^{} - h^s)^2}{1 + (\mu^{} - (\mu^s - \mu^r_{max}))^2},$$

$$v_2^m(\mu^m) = b_6(\mu^m - \mu^m_*)^2 - c_6,$$

$$\alpha^m(E(t),\mu^m,h^m) =$$

$$\begin{cases} \gamma^m(\mu^m,\mu^m) + \min\left(\frac{c_E}{E(t)^{k_E}},b_E\right) & \text{for } E(t) < \tau_E, \mu^{m,n}_{min} \le \mu^m \le \mu^{m,n}_{max} \\ \gamma^m(\mu^m,\mu^m) & \text{otherwise,} \end{cases}$$

$$\gamma^m(\mu^m,\mu^m) =$$

$$\begin{cases} \alpha_r^m & \text{for } \mu^m \in [\mu^m_{min},\mu^m_{max} - \delta], h^m \in [h^m_{min} + \delta, h^m_{max}], \\ \gamma^m_\mu(\mu^m)\gamma^m_h(h^m) & \text{for } \mu^m \in (\mu^m_{max} - \delta, \mu^m_{max}), h^m \in (h^m_{min},h^m_{min} + \delta), \\ \infty & \text{for } \mu^m \ge \mu^m_{max}, h^m \le h^m_{min}, \end{cases}$$

$$\gamma^m_\mu(\mu^m) = \frac{3\alpha^m_{rand}\delta^2}{(\mu^m)^2 - 2(\mu^m_{max} + \delta)\mu^m + (\mu^m_{max} + 2\delta)\mu^m_{max}},$$

$$\gamma^m_h(h^m) = \frac{3\delta^2}{(h^m)^2 - 2(h^m_{max} + \delta)h^m + (h^m_{min} - 2\delta)h^m_{max}},$$

-continued $$E_{in}^{end}(t) = \frac{a_7 - b_7}{1 + e^{\frac{k_7 Hb(t)}{(TBV)} - c_7}} + b_7,$$

$$Hb(t) = \int_{h_{min}^m}^{h_{max}^m} m(t, \mu^m, h^m) dh^m,$$

$$E(t) = E^{ex}(t) + E^{in}(t),$$

and also some auxiliary equations for the iron compartment model $$k_{gastro,1}(H(t)) = \frac{a_8 - b_8}{1 + e^{-k_8 H(t) + c_8}} + b_8,$$

$$H_{prod}(t) = \frac{a_H - b_H}{1 + e^{-k_H C(t) + c_H}} + b_H,$$

$$C(t) = -c_U U(t) + c_{a_5} a_5(t) + c_i i(t),$$

$$U(t) = \int_{\mu_{min}^r}^{\mu_{max}^r} \int_{h_{min}^r}^{h_{max}^r} \int_{\tau_{min}^r}^{\tau_{max}^r} r(t, \mu^r, h^r) d\mu^r dh^r d\tau^r + \int_{\mu_{min}^s}^{\mu_{max}^s} \int_{h_{min}^s}^{h_{max}^s} \int_{\tau_{min}^s}^{\tau_{max}^s} s(t, \mu^s, h^s) d\mu^s dh^s d\tau^s,$$

$$k_{41}(H(t)) = \frac{a_9 - b_9}{1 + e^{-k_9 H(t) + c_9}} + b_9, \text{ and } k_{51}(H(t)) = \frac{a_{10} - b_{10}}{1 + e^{-k_{10} H(t) + c_{10}}} + b_{10}.$$

Exemplification of the Above Described Models
5. Simulations for the Iron Model.

TABLE 3

Iron compartments in normal man (estimates for an average man: Height: 177 cm, weight: 70 kg. See Williams Hematology Table 40.1)

| Compartment | Iron content (mg) | Total body iron (%) |
| --- | --- | --- |
| Hemoglobin iron (Precursors + Erythrocytes) | 2200 | 67 |
| Storage iron | 1000 | 27 |
| Labile pool (macrophages) | 80 | 2.2 |
| Transport iron (plasma) | 3 | 0.08 |
| Other tissue iron | 138 | 3.72 |

TABLE 4

Parameter values for the iron model in a steady state.

| Parameter | Meaning | Value |
| --- | --- | --- |
| $k_{12}$ | transfer rate from plasma to precursor cells | 8.5 |
| $k_{15}$ | transfer rate from plasma to storage | 1.62 |
| $k_{23}$ | transfer rate from precursor cells to erythrocytes | 0.1199 |
| $k_{24}$ | transfer rate from precursor cells to macrophages | 0.0101 |
| $k_{34}$ | transfer rate from erythrocytes to macrophages | 0.0012 |
| $k_{41}$ | transfer rate from macrophages to plasma | 0.29965 |
| $k_{45}$ | transfer rate from macrophages to plasma | 0.0256 |
| $k_{51}$ | transfer rate from storage to plasma | 0.007 |

Values for the parameters of the iron submodel are assigned as described below. First, parameters are formed that are able to reflect the situation in a steady state. For this purpose, the population model and the iron model are decoded and the compartment model describing iron homeostasis is the only model investigated. Further, because of steady state, all transfer rates are assumed to be constant. Then, values are assigned to the transfer rates, such that the flow of iron from one compartment to another, and also the total amount of iron in each compartment, are assumed to be within physiological ranges. Moreover, for instance in Williams Hematology, a table can be found where the iron content for a 70 kg man is presented. See Table 3 for a list of the values.

Parameter values chosen based on this information are shown in Table 4. Note that in the steady state, losses of iron and absorption of iron are equal and, therefore, are not considered here. Thus, for the moment, iron homeostasis is considered as a closed system. Using these parameter values, a simulation was started close to the steady state values for each compartment. In addition, a situation was considered where more iron is incorporated in hemoglobin and, as a consequence, storage iron is decreased. Since, in this case the model is run with constant transfer rates and no feedback or regulation is taken into account, it takes quite a long time until the system finally reaches its steady state.

Further Development of the Erythropoiesis and Iron Hemeostasis Models

The models presented in Sections 2 and 3 above are very close to physiology and incorporate a lot of physiological mechanisms involved in erythropoiesis and iron homeostasis. As a consequence, the models are very extensive and lead to a class of extremely complicated mathematical equations. To solve the models, special numerical schemes have been developed to find numerical approximations for the population equations. See D. H. Fuertinger. A model for erythropoiesis. PhD thesis, University of Graz, Austria, 2012 (hereinafter "Fuertinger Thesis"). Although the approach chosen is very efficient, it is extremely computationally intensive, because systems of several thousands ordinary differential equations (ODE) have to be solved at every time step. Therefore, at the present time, simulations are only realizable on high performance computers, and thus not really practicable or viable in every day clinical practice and patient care, where such computers are not typically available. Since the iron component is such an important part of treatment of the anemia of renal failure, a simplified version of the models presented in Sections 2 and 3 is described hereinafter. The model presented hereinafter is still comprehensive and demanding with regard to computational costs, although the complexity of the numerical approximations reduces significantly. Instead of solving systems of several thousand ODEs, less than about a hundred ODEs have to be solved at every time step, which reduces the computational effort tremendously.

The first step is to restrict the population model presented in Section 2 to population equations with only one structural attribute, namely cell age (also called maturity of the cell). Avoidance of the structural attributes hemoglobin and transferrin receptors makes it necessary to take a step backward and reconsider how an iron model can be linked to a model describing the erythroid cell populations. Several of the assumptions made in Sections 2 and 3 have to be revisited. It is still important to keep track of how much iron is taken up by precursor cells and how much hemoglobin is contained in every cell. The lack of the structural feature hemoglobin, which allowed one to compute this quantity relatively easily, requires that other mechanisms have to be developed to replace it. The equations and assumptions are chosen such that the simplified model is as close to the one previously shown as possible. Nevertheless, these 'workarounds' only enable the description of the phenomenon of the accumulation of hemoglobin in cells and not so much the physiological mechanisms involved. Whereas this might not make a difference in most cases, the more extensive model might be needed to explain the development of RBC comprehensively for some patients with severe changes in these mechanisms.

To ensure that the description below can be read independently, a few important aspects of erythropoiesis and iron homeostasis are repeated hereinafter.

6. Erythropoiesis Model.

The aim is to develop a mathematical model which incorporates the basic mechanisms governing erythropoiesis including the control actions of erythropoietin and the potentially restricting effect of iron. Thus, the model has to include the regulatory processes for iron homeostasis, in particular describing those which are connected to erythropoiesis. The result is a comprehensive mathematical model which is able to predict red blood cell mass under EPO- and iron-therapy.

As a first step, in this chapter a model is developed which focuses solely on the effects of erythropoietin on erythroid cells. Hence, throughout this section, erythropoiesis is assumed to be sufficiently supplied with iron. Hereinafter, this model will be referred to as the Erythropoiesis Model, described in PCT Application No. PCT/US/2012/054264 published as WO 2013/036836 A2 on Mar. 14, 2013, whose contents and teachings are incorporated herein by reference in their entirety. The mathematical model developed in this section is applicable for a number of different situations, as long as it is reasonable to assume that erythropoiesis is not impaired because of a lack of iron availability. For instance, the Erythropoiesis Model is able to describe the recovery of red cell mass after blood donation, the reaction of the body to presurgical administration of ESAs, and changes in the number of erythrocytes of high altitude dwellers descending to sea level. See Fuertinger Thesis; D. H. Fuertinger, F. Kappel, S. Thijssen, N. W. Levin, and P. Kotanko. Journal of Mathematical Biology, 66(6):1209-1240, 2013. However, the Erythropoiesis Model is only applicable for a subpopulation of dialysis patients. 80-90% of dialysis patients treated with ESA suffer from functional iron deficiency at some stage in their therapy. See R. M. Schaefer and L. Schaefer. Nephrology Dialysis Transplantation, 13:9-12, 1998. It has to be considered carefully whether, even when treated with iron compounds, it is reasonable to assume that iron supply is sufficient in patients suffering from chronic kidney disease (CKD patients on dialysis treatment or not). Moreover, the Erythropoiesis Model helps to understand what the most important dynamics considering red blood cell production are. In Section 7 an Iron Model (compartment model) is developed and in Section 7.2 it is explained how this model is linked to the Erythropoiesis Model and extends it to a even more extensive and detailed model for erythropoiesis, thus providing a solid basis for a more general description of the altered processes during the very complex pathological situation of anemia of renal failure.

The Erythropoiesis Model is based on structured population models describing the different erythroid cell stages. Five different population classes of cells are considered: BFU-Es, CFU-Es, erythroblasts, marrow reticulocytes and mature erythrocytes circulating in the bloodstream (including peripheral reticulocytes). In the Erythropoiesis Model individual cells are distinguished according to their maturity, which can also be referred to as cell age. The commitment to the erythroid lineage is an irreversible event. A differentiated cell cannot regress or switch into another differentiation pathway. Thus, once a multipotent stem cell is committed to the erythroid lineage, it undergoes the complete series of differentiations until it becomes a mature red blood cell, or it dies eventually during this process. While maturing, the cell divides a number of times. Hence, age-structured population models of the form $$\frac{\partial}{\partial t}u(t,\mu) + v(E(t))\frac{\partial}{\partial \mu}u(t,\mu) = (\beta(E(t)),\mu) - \alpha(E(t),\mu))u(t,\mu), \quad (10)$$

are used in order to describe the development of the cell populations. Here $u(t,\mu)$ denotes the population density of the cell population at time t with maturity $\mu$. Further, the functions $\beta$ and $\alpha$ describe the division rate and the rate of apoptosis of the cells, respectively. The functions $\alpha$ and $\beta$ a priori depend on the maturity $\mu$ and the concentration of EPO $E(t)$, respectively, at time t. The function v describes the maturation velocity and depends on the concentration $E(t)$.

For the different population classes, the characteristic properties (proliferation rate, rate of apoptosis and maturation velocity) differ. While the cell matures, it changes its morphological characteristics, such as the number of EPO- and transferrin-receptors expressed on the surface.

Figure 9A:
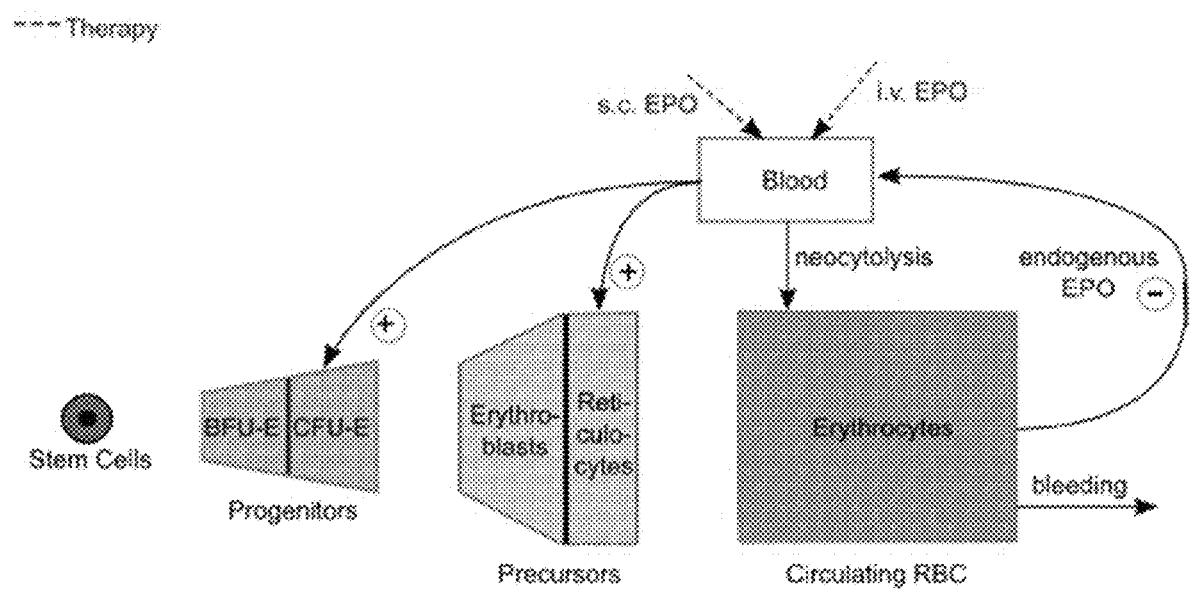
FIG. 9A is a schematic illustration of the organizational diagram of an anemia (erythropoiesis) model suitable for generating virtual patients in some embodiments of the present teachings.
Figure 9B:
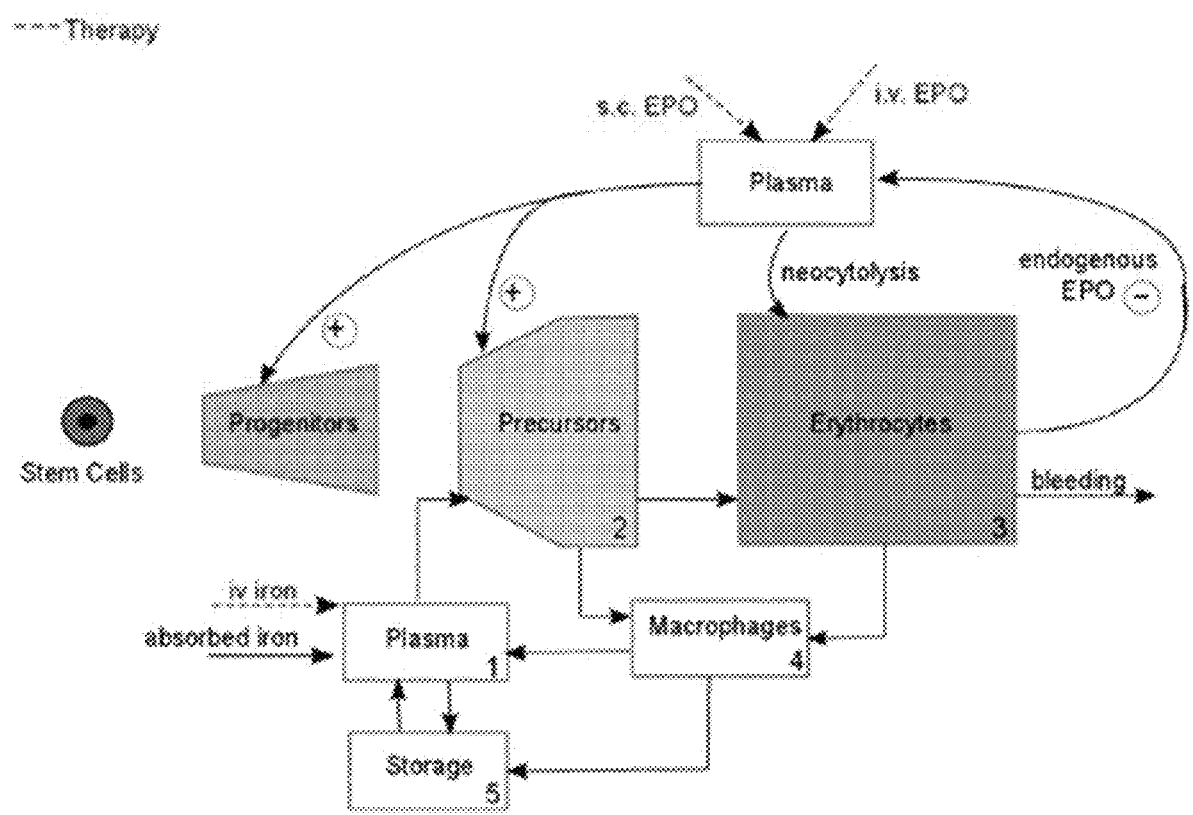
FIG. 9B is a schematic illustration of the organizational diagram of an anemia (erythropoiesis) model including an iron submodel suitable for generating virtual patients in some embodiments of the present teachings.

In the following sections, the assumptions that were made for the different population classes are listed, briefly described, and the mathematical equations that arise in consequence are stated. FIG. 9A gives an overview of the design and organization of the model.

6.1. Progenitor Cells: BFU-E and CFU-E Cells

Assumptions:

1. The number of cells, which commit to the erythroid lineage, is constant.

2. Cells normally stay in this stage for 8 days (3 days BFU-E and 5 days CFU-E).

3. EPO has no effect on the number of divisions or the rate of apoptosis of BFU-E.

4. The proliferation rate of CFU-E cells is constant.

5. The rate of apoptosis of CFU-E depends highly on EPO levels.

6. The maturation velocities of BFU-E and CFU-E cells are constant.

The process by which stem cells are recruited into proliferating progenitor population remains unclear. There are several hypotheses including an environmental dependency, that it is a random event, etc. For the moment, the number of stem cells entering the erythroid lineage is assumed to be independent of EPO and thus constant. The change in population of the progenitor cells over time are described considering two different classes of cells: namely BFU-E and CFU-E cells.

The earliest identifiable erythroid progenitor cell is the Burst-forming Unit Erythroid (BFU-E). At first these cells express only a very small number of EPO receptors on the surface. See Wintrobe's Clinical Hematology. Thus, it is reasonable to assume EPO has no effect on proliferation or apoptosis of these cells. See Wu et al. In culture it lasts around 6-7 days until human BFU-E have all the functional characteristics of the next cell stage—Colony-forming Unit Erythroid cells (CFU-E cells) (Assumption 2). See Williams Hematology. Morphologically, it is difficult to distinguish between those two types of cells, because there are cells in between these two developmental stages which show characteristic properties between BFU-E and CFU-E cells. Therefore, a distinction is valid but artificial.

The BFU-E cell class is described by the following population equation $$\begin{cases} \frac{\partial}{\partial t}p(t,\mu^p) + \frac{\partial}{\partial \mu^p}p(t,\mu^p) = \beta^p p(t,\mu^p), \\ p(t,0) = S_0 \\ p(0,\mu^p) = p_0(\mu^p), \end{cases}$$

where $p(t, \mu^p)$ is the population density of the cell class at time t with maturity $\mu^p$, $0 \leq \mu^p \leq \mu^p_{max} = 7$, $t>0$. Further, $\beta^p$ is a constant proliferation rate and $\alpha^p \equiv 0$ (Assumption 3), $S_0$ describes the number of cells committing to the erythroid lineage (Assumption 1) and $p_0(\mu^p)$ is the population density at t=0.

Once a cell reaches the maximum age for BFU-E cells, it leaves this population class and enters the CFU-E class. Consequently, there is a continual flux of cells from one population class to the next one. CFU-E are more rapidly dividing cells than BFU-E. See Wu et al. During this stage, cells are very sensitive to EPO levels, and, under normal conditions, large numbers of generated CFU-E are not surviving. See Wintrobe's Clinical Hematology. CFU-E are highly dependent on EPO to prevent them from apoptosis, i.e., the mortality for this population class depends on the EPO concentration. Altogether, the following equations for the second class are obtained:

$$\begin{cases} \frac{\partial}{\partial t}q(t,\mu^q) + \frac{\partial}{\partial \mu^q}q(t,\mu^q) = (\beta^q \alpha^q(E(t)))q(t,\mu^q), \\ q(t,\mu^q_{min}) = p(t,\mu^p_{max}), \\ q(0,\mu^q) = p_0(\mu^q), \end{cases}$$

where $q(t, \mu^q)$ is the population density of the CFU-E class at time t with maturity $\mu^q$, $t>0$ and $7=\mu^q_{min} \leq \mu^q \leq \mu^q_{max}=13$. Further on, $\beta^q$ stands for a constant proliferation rate (Assumption 4), $\alpha^q(E(t))$ denotes the apoptosis rate depending on the EPO-concentration (Assumption 5), $q(t, \mu^q)=p(t, \mu^p_{max})$ describes the number of cells leaving the BFU-E cell stage and entering the CFU-E cell stage and $q_0(\mu^q)$ is the population density at t=0.

A sigmoid function is used to describe the rate of apoptosis, $$\alpha^q(E(t)) = \frac{a_1 - b_1}{1 + e^{k_1 E(t) - c_1}} + b_1,$$

where E(t) is the EPO concentration at time t and $a_1$, $b_1$, $c_1$ and $k_1$ are positive constants with $a_1 > b_1$. The function $\alpha^q$ monotonically decreases with increasing EPO concentration. Thus, a higher level of EPO causes more cells to survive.

Note that, because of Assumption 6, the cell age of progenitor cells coincides with the actual age of the cell, i.e., one defines $v^p = v^q \equiv 1$, $\forall t \geq 0$.

6.2. Precursor Cells: Erythroblasts and Marrow Reticulocytes

Assumptions:

7. Cells stay in this stage for 6-8 days (5 days erythroblasts and 1-3 days marrow reticulocytes).

8. The class erythroblasts consists of all cell stages from proerythroblast to orthochromatophilic erythroblast.

9. EPO has no effect on the number of divisions or the rate of apoptosis of erythroblasts. The proliferation rate of erythroblasts is assumed to be constant.

10. The maturation velocity of erythroblasts is constant.

11. Reticulocytes mature but do not proliferate.

12. The maturation velocity of reticulocytes depends on EPO.

13. A constant portion of marrow reticulocytes is phagocytosed.

After a CFU-E differentiates to a proerythroblast, it takes about another 6-8 days until the cell is released from the bone marrow into the bloodstream. See Jandl. The various stages of maturation from proerythroblast to orthochromatophilic erythroblast are referred to as erythroblasts. The cells undergo several mitotic divisions until, at the stage of orthochromatophilic erythroblast, they lose their ability to divide and enter a maturation period. The erythroblastic pyramids appear normal, with no evidence of additional mitotic divisions, when production increases, i.e., the proliferation of erythroblasts is assumed to be independent of EPO levels and defined to be constant. See Williams Hematology.

Hence, the erythroblast class can be described by the following equation $$\begin{cases} \frac{\partial}{\partial t}r(t,\mu^r) + \frac{\partial}{\partial \mu^r}r(t,\mu^r) = \beta^r r(t,\mu^r), \\ r(t,\mu^r_{min}) = q(t,\mu^q_{min}), \\ r(0,\mu^r) = r_0(\mu^r), \end{cases}$$

where $r(t, \mu^r)$ is the population density of the erythroblasts at time t with maturity $\mu^r$, $t>0$ and $13=\mu^r_{min} \leq \mu^r \leq \mu^r_{max}=18$. Further, $\beta^r$ is a constant proliferation rate and $\alpha^s \equiv 0$ (Assumption 9), the maturation velocity $v^r \equiv 1$ (Assumption 10), $r(t, \mu^r_{min})=q(t, \mu^q_{max})$ describes the number of cells leaving the CFU-E stage and entering the erythroblasts cell stage, and $r_0(\mu^r)$ is the population density at t=0.

The differentiating process from orthochromatophilic erythroblasts to marrow reticulocytes involves the extrusion of the cell nucleus. Reticulocytes are not capable of cell divisions (Assumption 11), i.e., $\beta^s = 0$. In the Erythropoiesis Model, one does not account for an impaired erythropoiesis due to iron deficiency. Still, even when the erythroid cells in the bone marrow are sufficiently supplied with iron, not all precursor cells survive. Some of the reticulocytes die before they are released to the blood stream. See G. Barosi, M. Cazzola, C. Berzuini, S. Quaglini, and M. Stefanelli. British Journal of Haematology, 61:357-370, 1985; M. Stefanelli, D. P. Bentley, I. Cavill, and H. P. Roeser. The American Journal of Physiology, 247:842-849, 1984. This is why Assumption 13 is made.

A raised EPO concentration shortens the marrow transit time of precursor cells. If the EPO level is elevated, marrow reticulocytes are released prematurely. This aspect is accounted for by allowing the maturation velocity of reticulocytes to vary depending on erythropoietin concentration. Thus, although the maximum cell age of marrow reticulocytes is fixed, the actual transit time for the cells varies between 1-3 days. Hence, altogether the transit time for precursor cells is between 6-8 days (Assumption 7).

The population equation referring to marrow reticulocytes is $$\begin{cases} \frac{\partial}{\partial t}s(t,\mu^s) + v^s(E(t))\frac{\partial}{\partial \mu^s}s(t,\mu^s) = -\alpha^s s(t,\mu^s), \\ v^s(E(t))s(t,\mu^s_{min}) = r(t,\mu^r_{max}), \\ s(0,\mu^s) = r_0(\mu^s), \end{cases}$$

where $s(t, \mu^s)$ is the reticulocytes population density at time t with maturity $\mu^s$, t>0 and $18=\mu^s_{min} \leq \mu^s \leq \mu^s_{max}=20$. Further on, $v^s(E(t))$ is the maturation velocity depending on EPO (Assumption 12), $\alpha^s$ denotes the rate with which reticulocytes are phagocytosed (Assumption 13), $v^s(E(t))s(t, \mu^{min}_s) = r(t, \mu^r_{max})$ describes the number of cells leaving the erythroblast cell stage and entering the reticulocyte cell stage, and $r_0(\mu^s)$ is the population density at t=0.

A sigmoid function is used to describe the changes in maturation velocity, $$v^s(E(t)) = \frac{a_2 - b_2}{1 + e^{-k_2 E(t) + c_2}} + b_2,$$

where E(t) is the EPO concentration at time t and $a_2$, $b_2$, $c_2$ and $k_2$ are positive constants with $a_2 > b_2$. The maturation velocity increases with a rising concentration of EPO. Note that a slower maturation velocity causes the cells to reach the maximum cell age $\mu^s_{max}$ at a later point, whereas a faster maturation velocity shortens the transit time, i.e., the cells reach $\mu^s_{max}$ earlier.

6.3. Erythrocytes.

Assumptions:

14. Erythrocytes and blood reticulocytes are subsumed in one class.

15. Cells mature but do not proliferate.

16. There is a fixed random daily break-down of red blood cells (not to be confused with loss of erythrocytes due to senescence).

17. A drop in EPO concentration beneath a threshold precipitates neocytolysis.

18. Erythrocytes with age between 14-21 days are likely to be affected by neocytolysis.

19. Cells are phagocytosed when they reach the maximum age.

20. The maximum age of erythrocytes in a healthy persons is 120 days.

The reticulocytes are released from the bone marrow into the blood stream and within 1-2 days they mature to erythrocytes. Circulating red blood cells have no nuclei and therefore they are not able to proliferate and they are not able to repair themselves. Thus, the life span of these cells is limited. In healthy adults the average life span is about 120 days, but it can significantly shorten in some pathologies. See e.g., Jandl. If not otherwise stated, 120 days is used as the maximal age of erythrocytes for the Erythropoiesis Model.

Cells can be lost for different reasons: due to internal or external bleeding, because of random daily-breakdown, because neocytolysis is triggered, and, because of eryptosis of senescent cells.

Altogether, the following equation is obtained for red blood cells:

$$\begin{cases} \frac{\partial}{\partial t}m(t,\mu^m) + \frac{\partial}{\partial \mu^m}m(t,\mu^m) = -\alpha^m(E(t),\mu^m)m(t,\mu^m), \\ m(t,0) = v^s(E(t))s(t,\mu^s_{max}), \\ m(0,\mu^m) = m_0(\mu^m), \end{cases}$$

where $m(t, \mu^m)$ is the population density for the erythrocyte class at time t with maturity $\mu^m$, t>0 and $0=\mu^m_{min} \leq \mu^m \leq \mu^m_{max}=120$ (Assumption 20). Moreover, $m(t, 0) = v^s(E(t))s(t, \mu^s_{max})$ describes the number of reticulocytes entering the blood stream and $m_0(\mu^m)$ is the population density at t=0. In the population equation $\alpha^m(E(t), \mu^m)$ denotes a random daily break-down and neocytolysis $$\alpha^m(E(t),\mu^m) = \begin{cases} \gamma^m(\mu^m) + \min\left(\frac{c_E}{E(t)^{k_E}}, b_E\right) & \text{for } E(t) < \tau_E, \mu^{m,n}_{min} \leq \mu^m \leq \mu^{m,n}_{max}, \\ \gamma^m(\mu^m) & \text{otherwise,} \end{cases}$$

where $b_E$, $c_E$, $k_E$ are positive constants, $\tau_E$ is the threshold beneath which neocytolysis is triggered (Assumption 17), and $[\mu^{m,n}_{min}, \mu^{m,n}_{max}] = [14, 21]$ (Assumption 18) is the age-interval during which cells are affected by neocytolysis, and t≥0. Additionally, it is possible to add a further term $\alpha^m_{bleed}(t)$ to the mortality rate in case of bleeding. Since it is assumed that a cell is phagocytosed when it reaches its maximum age (Assumption 19), the mortality rate $\gamma^m(\mu^m)$ needs to be chosen such that $\gamma^m(\mu^m) = \alpha^m_{rand}$ for $\mu^m_{min} \leq \mu^m \leq \mu^m_{max} - \delta$ with $\delta > 0$ sufficiently small and $\int_{\mu^m_{max}-\delta}^{\mu^m_{max}} \gamma^m(\mu^m) = \infty$. Here $\alpha^r_{rand}$ is a random daily break-down (Assumption 16). A possible choice for $\gamma^m(\mu^m)$ is $$\gamma^m(\mu^m) = \begin{cases} \alpha^m_{rand} & \text{for } \mu^m \in [\mu^m_{min}, \mu^m_{max} - \delta], \\ \frac{3\alpha^m_{rand}\delta^2}{(\mu^m)^2 - 2(\mu^m_{max} + \delta)\mu^m + (\mu^m_{max} + 2\delta)\mu^m_{max}} & \text{for } \mu^m \in (\mu^m_{max} - \delta, \mu^m_{max}), \\ \infty & \text{for } \mu^m \geq \mu^m_{max}. \end{cases}$$

6.4. Erythropoietin

Assumptions:

21. Release of EPO is controlled by a negative feedback mechanism according to the oxygen content.

22. Oxygen carrying capacity is directly proportional to the number of erythrocytes.

23. The degradation rate of EPO is constant.

24. There is a slight delay in reaction of the EPO production rate to the number of RBC but this is negligible compared to the duration of development of erythrocytes.

The kidneys adjust the release of EPO according to the oxygen carrying capacity of the blood. If blood oxygen content is lower than normal, then EPO production increases and vice versa. Thus, the production of EPO is controlled by a negative feedback mechanism and allows for more red blood cells to be developed in case of an undersupply of the body with oxygen by opposing programmed cell death of erythroid progenitor cells. Further, if EPO decreases beneath a certain threshold, neocytolysis is triggered, that is, a process wherein macrophages start to phagocytose young erythrocytes (neocytes).

A sigmoid function which depends on blood oxygen partial pressure is used to model the feedback involving the release of erythropoietin $E_{in}^{end}(t)$ from the kidneys into plasma. As a consequence of Assumption 22, the amount of $E_{in}^{end}(t)$ of EPO released by the kidney per unit time can be directly computed by use of the total population of erythrocytes $M(t) = \int_0^{\mu_{max}^m} m(t, \mu^m) d\mu^m$. Recall that this class consists of all circulating red blood cells (Assumption 14).

$$E_{in}^{end}(t) = \frac{a_3 - b_3}{1 + e^{k_3 \tilde{M}(t) - c_3}} + b_3,$$

where $$\tilde{M}(t) = \frac{10^{-8} M(t)}{TBV}$$

is a scaled erythrocytes "concentration". Here, TBV is the total blood volume. The constants $a_3, b_3, c_3, k_3$ are positive and satisfy $a_3 > b_3$. The function $E_{in}^{end}(t)$ is monotonically decreasing. Thus, the release of EPO increases if the number of circulating red blood cells decreases (Assumption 21). The dynamics of the endogenous EPO concentration $E^{end}(t)$ in plasma are described by the following ordinary differential equation:

$$\frac{d}{dt} E^{end}(t) = \frac{1}{TBV} E_{in}^{end}(t) - c_{deg}^{end} E^{end}(t), \quad (11)$$

where $E^{end}(t)$ is the endogenous EPO concentration in plasma, $E_{in}^{end}$ is the amount of EPO released by the kidneys and $c_{deg}^{ex}$ describes the constant degradation rate of endogenous EPO (Assumption 23).

The degradation rate $c_{deg}^{ex}$ for exogenous EPO differs from the one for endogenous EPO and varies according to the kind of ESA administered. Therefore, an additional ODE is needed to describe the change in the plasma concentration of an ESA $$\frac{d}{dt} E^{ex}(t) = \frac{1}{TBV} E_{in}^{ex}(t) - c_{deg}^{ex} E^{ex}(t). \quad (12)$$

Here $E_{in}^{ex}(t)$ is the rate at which the artificial hormone is administered and $c_{deg}^{ex}$ is the rate with which the exogenous hormone is degraded. In intravenous administration, the total amount of the agent is injected into a vein, within a very short time interval. In this case $E_{in}^{ex}(t)$ can be approximated by $E_0^{ex}(t) \delta_{t_0}(t)$, where $E_0^{ex}$ is the amount of artificial hormone administered and $\delta_{t_0}(t)$ is the Dirac delta impulse located at $t_0$, the time when the administration takes place. The overall concentration of EPO in blood consists of the naturally produced erythropoietin in the body and the administered ESA $$E(t) = E^{ex}(t) + E^{end}(t)$$

6.5. Mathematical Model Erythropoiesis Model

For the convenience of the reader, all equations of the Erythropoiesis Model are collected in this section:

$$\frac{\partial}{\partial t} p(t, \mu^p) + \frac{\partial}{\partial \mu^p} p(t, \mu^p) = \beta^p p(t, \mu^p),$$

-continued $$\frac{\partial}{\partial t} q(t, \mu^q) + \frac{\partial}{\partial \mu^q} q(t, \mu^q) = (\beta^q - \alpha^q(E(t))) q(t, \mu^q),$$

$$\frac{\partial}{\partial t} r(t, \mu^r) + \frac{\partial}{\partial \mu^r} r(t, \mu^r) = \beta^r r(t, \mu^r),$$

$$\frac{\partial}{\partial t} s(t, \mu^s) + v^s(E(t)) \frac{\partial}{\partial \mu^s} s(t, \mu^s) = -\alpha^s s(t, \mu^s),$$

$$\frac{\partial}{\partial t} m(t, \mu^m) + \frac{\partial}{\partial \mu^m} m(t, \mu^m) = -\alpha^m(E(t), \mu^m) m(t, \mu^m),$$

$$\frac{d}{dt} E^{end}(t) = \frac{1}{TBV} E_{in}^{end}(t) - c_{deg}^{ex} E^{ex}(t),$$

$$\frac{d}{dt} E^{ex}(t) = \frac{1}{TBV} E_{in}^{ex}(t) - c_{deg}^{ex} E^{ex}(t)$$

where $$\alpha^q(E(t)) = \frac{a_1 - b_1}{1 + e^{k_1 E(t) + c_1}} + b_1,$$

$$v^s(E(t)) = \frac{a_2 - b_2}{1 + e^{-k_2 E(t) + c_2}} + b_2,$$

and $$\alpha^m(E(t), \mu^m) = \begin{cases} \gamma^m(\mu^m) + \min\left(\frac{c_E}{E(t)^{k_E}}, b_E\right), & \text{for } E(t) < \tau_E, \mu_{min}^{m,n} \le \mu^m \le \mu_{max}^{m,n} \\ \gamma^m(\mu^m), & \text{otherwise,} \end{cases}$$

with $$\gamma^m(\mu^m) = \begin{cases} \alpha_{rand}^m & \text{for } \mu^m \in [\mu_{min}^m, \mu_{max}^m - \delta], \\ \frac{3\alpha_{rand}^m \delta^2}{(\mu^m)^2 - 2(\mu_{max}^m + \delta)\mu^m + (\mu_{max}^m + 2\delta)\mu_{max}^m} & \text{for } \mu^m \in (\mu_{max}^m - \delta, \mu_{max}^m), \\ \infty & \text{for } \mu^m \ge \mu_{max}^m. \end{cases}$$

Further, the boundary conditions are given by $$p(t, 0) = S_0,$$

$$q(t, \mu_{min}^q) = p(t, \mu_{max}^p),$$

$$r(t, \mu_{min}^r) = q(t, \mu_{max}^q),$$

$$v^s(E(t)) s(t, \mu_{min}^s) = r(t, \mu_{max}^r),$$

$$m(t, 0) = v^s(E(t)) s(t, \mu_{max}^s),$$

$$m(0, \mu^m) = m_0(\mu^m),$$

and the initial values are $$p(0, \mu^p) = p_0(\mu^p),$$

$$q(0, \mu^q) = q_0(\mu^q),$$

$$r(0, \mu^r) = r_0(\mu^r),$$

$$s(0, \mu^s) = r_0(\mu^s),$$

$$E^{end}(0) = E_0^{end},$$

$$E^{ex}(0) = E_0^{ex}.$$

The feedback is described by $$E_{in}^{end}(t) = \frac{a_3 - b_3}{1 + e^{k_3 \tilde{M}(t) - c_3}} + b_3,$$

-continued where $$\tilde{M} = \frac{10^{-8} M(t)}{TBV}, \text{ with } M(t) = \int_0^{\mu_{max}^m} m(t, \mu^m) d\mu^m$$

and one has $$E(t) = E^{ext}(t) + E^{end}(t).$$

7. Iron Homeostasis.

As described above, much of the iron in the human body can be found in circulating erythrocytes incorporated in hemoglobin. However, most of the iron used for the production of new erythrocytes comes from hemoglobin recycling and not from absorption. When a senescent red cell is phagocytosed, the macrophage internalizes hemoglobin, degrades it and exports it back out into blood circulation.

Iron is stored in form of ferritin or hemosiderin, where the latter is more a kind of a long-term storage, because iron within deposits of hemosiderin is very poorly available. Storage sites can be found mainly in the liver, the spleen and the bone marrow but, for instance, small amounts of hemosiderin can be found in almost any tissue. There are differences between men and women in the amount of iron that is stored (Females about 200-400 mg, Males about 1000 mg). See Crepaldi.

Iron is carried around in plasma by a transport protein, which is called transferrin. Transferrin is produced by the liver. Cells that are in need for iron express transferrin receptors, and after transferrin has formed a complex with this receptor, iron is transported into the cell. Transferrin exists in three different forms: iron-free (apotransferrin), one iron (monoferric transferrin) and two iron (differic transferrin) atoms bound. The concentration of iron and the amount of transferrin present in plasma determine the relative abundance of each form. Although iron bound to transferrin amounts to only about 3 mg of total body iron, it is the most important iron pool with the highest rate of turnover, about 30 mg/day. Approximately 80% of this iron is transported to the bone marrow and used by erythroid cells. See Lieu et al. The amount of transferrin-bound iron is determined by three processes: macrophage iron recycling, (hepatic) iron storage and duodenal iron absorption. See Wrighting.

In the last 15 years, understanding of the regulation of systemic iron homeostasis has changed substantially. The antimicrobial peptide hepcidin, which is secreted by the liver, was identified to be the systemic iron regulator. Hepcidin inhibits iron transport by binding to the iron exporter ferroportin. Hence, it keeps gut enterocytes from secreting iron into circulation, thereby functionally reducing iron absorption. Further, it prevents iron release from macrophages and blocks the stores as well, by shutting off the means of transport out of cells.

There exist some sensing mechanisms in the liver that gauge the amount of iron needed to support erythropoiesis. Note that hepatocytes in the liver, which secrete hepcidin, also release transferrin into circulation and are one of the major iron storage sites. If the concentration of iron stores are too low and/or erythropoiesis is increased, then the level of the hormone hepcidin is decreased. Thus, for instance, low hepcidin concentrations are observed in patients with absolute iron-deficiency anemia, or anemias with high erythropoietic activity. See Goodnough 2010. The consequence of a lower hepcidin level is that more iron is taken up via the duodenum and more iron is released from macrophages and from the stores. See Crichton; Fleming. If iron stores are full and/or erythropoiesis is decreased, then more hepcidin is secreted by hepatocytes. Dietary iron absorption, macrophage iron recycling and release of iron from stores is partly or fully blocked as a result of the binding to the iron exporter ferroportin.

Hepcidin is an acute phase-reactant, and, during inflammation, cytokines stimulate overproduction of hepcidin. Hence, the feedback is altered during inflammation, which is a prominent problem in chronic kidney disease. As a consequence, the body is not able to sufficiently supply developing red blood cells with iron and erythropoiesis is impaired, although there might be more than enough iron in stores and macrophages, but it is simply not available. This paradoxical situation is called functional iron deficiency, a condition where stored iron is sufficient, but circulating iron is deficient, whereas a situation where the iron content of the body is too low (depleted stores) is referred to as absolute iron deficiency that occurs when iron stores are depleted.

7.1 Iron Model

Assumptions

25. Five iron pools are considered within the body: a plasma pool, iron in precursor cells, iron in erythrocytes, iron in the macrophages and a storage pool.

26. Other iron in the body is ignored.

27. Hepcidin regulates iron homeostasis.

28. Stressed erythropoiesis and depleted stores decrease the amount of hepcidin released into plasma.

29. Large iron stores and inflammation increase hepcidin levels.

30. The amount of iron in plasma is proportional to the amount of transferrin molecules carrying iron. (Free iron is neglected.)

31. There is no differentiation between monoferric and differic transferrin.

32. Iron is only lost via loss of cells, i.e. iron lost via urine and sweat is neglected.

Iron is a part of hemoglobin which provides the means of $O_2$ transport to the tissue. The rate at which iron can be released to plasma from existing stores and macrophages may easily limit the rate of iron delivery for hemoglobin synthesis. Therefore, a strong relationship between impaired erythropoiesis and total body iron burden exists. See Crichton for an excellent description of iron homeostasis and its effects.

Iron is a substance which is very tightly controlled from the body as iron overload is toxic. Iron homeostasis can be only achieved by the control of absorption because the human body, unlike other mammals, is not able to influence the excretion of iron. Under normal circumstances the average daily loss of iron is very small (men 1 mg, women 2 mg, because of menstruation).

For the Iron Model, five dynamic iron pools are considered within the body: a plasma pool, iron in precursor cells, iron in erythrocytes, iron in the macrophages and a storage pool. Hence, ferritin and hemosiderin stores are lumped together. Other iron in the body is ignored. The amount of iron lost via urine and sweat is neglected. Thus, in this model, excretion of iron only takes place when cells are lost. On one hand, this can be due to loss of RBCs, i.e., due to external bleeding, and, on the other hand, there is a daily loss of epithelial cells. Further, one assumes that only the precursor cells in the bone marrow uptake iron, and ineffective erythropoiesis depends on the amount of iron which can be provided for erythropoiesis. Moreover, the model accounts for the loss of iron from erythrocytes during senescence.

The general form of the compartmental Iron Model is as follows:

$$\frac{d}{dt}a_1 = k_{41}(H)a_4 + h_{iv,1}a_{iv} + k_{gastro,1}(H)a_{gastro} + k_{51}(H)a_5 - k_{15}a_1 - k_{12}a_1,$$

$$\frac{d}{dt}a_2 = k_{12}a_1 - f_{24} - f_{23},$$

$$\frac{d}{dt}a_3 = f_{23} - f_{34} - f_{3,out},$$

$$\frac{d}{dt}a_4 = f_{24} + f_{34}a_3 - k_{41}(H)a_4 - k_{45}a_4,$$

$$\frac{d}{dt}a_5 = k_{15}a_1 - k_{45}a_4 - k_{51}(H)a_5.$$

Note, in the above equations, the dependence of particular components on t was not explicitly stated to simplify notation. Furthermore, $\alpha_i$, i=1, ..., 5, denotes the amount of iron in the compartment i and $k_{ij}$, i,j=1,000, 5 are the transfer rates from compartment i to compartment j, i.e., $k_{ij}a$, is the rate at which iron is moving from compartment i to compartment j. Further, $f_{ij}$ denote the rates at which iron is transferred from compartment i into compartment j, when it is not of the simple form $k_{ij}\alpha_i$; $f_{3,out}$ is the amount of iron which is lost by bleeding. Additionally, $\alpha_{iv}$ denotes the amount of iron intravenously administered, whereas $\alpha_{gastro}$ is the amount of iron in the duodenum. Finally, $k_{iv,1}$ and $k_{gastro,1}(H)$ are the corresponding flow rates. The rate $k_{gastro,1}$ can be described by a decreasing sigmoidal function $$k_{gastro,1}(H(t)) = \frac{a_5 - b_5}{1 + e^{-k_5 H(t) + c_5}} + b_5,$$

where $a_5$, $b_5$, $c_5$ and $k_5$ are positive constants with $a_8 > b_8$. The function H(t) is the solution of the differential equation (13) below.

Since the time needed to administer iron is very short compared to other time constants in the system, the following can be taken $$k_{iv,1}a_{iv} = a_{iv,total}\delta_{t_0}.$$

Here $a_{iv,total}$ is the total amount of iron administered and $\delta_{t_0}$ is the Dirac delta function located at $t_0$.

7.1.1 Hepcidin Feedback

The regulator of iron homeostasis is hepcidin, a peptide hormone produced by the liver. Hepcidin negatively regulates the availability of iron in plasma by direct inhibition of ferroportin. Ferroportin is the iron exporter required for iron egress from iron exporting cells, as for instance, enterocytes and macrophages. Hepcidin acts as a medium to withhold iron from certain invasive bacteria, as they are not able to proliferate under conditions of insufficient iron supply. The dynamics of the hepcidin concentration in plasma is calculated according to $$\frac{d}{dt}H(t) = \frac{1}{TBV}H_{prod}(t) - c_{deg}^H H(t), \quad (13)$$

where $H_{prod}(t)$ is the rate at which hepcidin, produced by the hepatocytes, is released into the plasma at time t. TBV is the total blood volume, and $c^H_{deg}$ is the rate at which hepcidin is degraded. The production rate $H_{prod}(t)$ of hepcidin is obtained as the result of a feedback loop involving the total precursor cell population, the amount of iron stored and the state of inflammation of the patient, $$H_{prod}(t) = f(U(t), a_5(t), i(t)).$$

Here $$U(t) = \int_{\mu^r_{min}}^{\mu^r_{max}} r(t, \mu^r) d\mu^r + \int_{\mu^s_{min}}^{\mu^s_{max}} s(t, \mu^s) d\mu^s$$

where U(t) describes the total precursor cell population (erythroblasts+reticulocytes). Further, $a_5(t)$ is the amount of iron stored and i(t) is the inflammation status at time t. The feedback is modeled using a monotonically increasing sigmoidal function $$H_{prod}(t) = \frac{a_H - b_H}{1 + e^{-k_H C(t) + c_H}} + b_H$$

where $a_H$, $b_H$, $c_H$ and $k_H$ are positive constants with $a_H > b_H$. The function $$C(t) = -c_U U(t) + c_{a_5} a_5(t) + c_i i(t)$$

is an auxiliary equation that increases if stores or inflammation status rises, and decreases when more RBCs are produced. Here, $c_v$, $c_{a5}$ and $c_i$ are positive constants.

7.2. Iron Model Linked to the Erythropoiesis Mode.

Assumptions

33. All types of precursor cells synthesize hemoglobin.
34. The rate at which the amount of hemoglobin in precursor cells changes, depends on the number of transferrin receptors (TfR) on the cell membrane and the amount of iron in plasma.
35. Cells with the same age express the same amount of TfR on the membrane.
36. An erythroblast starts with 300,000 TfR on the cell membrane.
37. This number increases sharply and peaks after 1.5 days at 800,000 TfR.
38. After that time, it declines to 100,000 TfR on bone marrow reticulocytes.
39. The number of TfR on bone marrow reticulocytes is constant (100,000 TfR/cell).
40. The rate of apoptosis of precursor cells (erythroblasts AND reticulocytes) depend on cell age and hemoglobin.
41. Iron that enters a precursor cell is incorporated into hemoglobin, i.e., no free iron in the cell is considered.
42. Erythrocytes don't lose iron during senescence.

Some thought has to be given to how the iron model can be linked to the population model. Iron is consumed by precursor cells (erythroblasts and bone marrow reticulocytes) and used for hemoglobin synthesis. The amount of iron that is taken up by a cell depends on the number of transferrin receptors (TfR) expressed on the membrane and the concentration of iron in plasma. In order to simplify notation, the minimal cell age of precursor cells $\mu^r_{min}$ is set to zero, i.e., the cell age for erythroblasts is shifted from $8 = \mu^r_{min} \leq \mu^r \leq \beta^r_{max} = 13$ to $0 = \mu^r_{min} \leq \mu^r \leq \mu^r_{max} = 5$ and the cell age for bone marrow reticulocytes consequently is shifted from $13 = \mu_s^{min} \leq \mu^s \leq \mu^s_{max} = 15$ to $5 = \mu^s_{min} \leq \mu^s \leq \mu^s_{max} = 7$.

The contact rate between the TfRs of a cell and transferrin molecules in plasma carrying iron is governed by the law of mass action and thus is given by:

$$d_1 \tau(t) \frac{a_1(t)}{TBV}, \quad (14)$$

where $d_1$ is a rate constant that differs for different patients, as it depends on the volume of the active bone marrow. Further, $\tau(t)$ is the cumulative amount of TfR on cell membranes of precursor cells (erythroblasts and bone marrow reticulocytes) at time t and $\alpha_1(t)$ is the concentration of iron in plasma at time t. Note that this is at the same time the rate with which iron leaves the plasma compartment and enters the precursor cells. The cumulative sum of TfR expressed on all precursor cells $\tau(t)$ is determined by $$\tau(t) = \int_{\mu^r_{min}}^{\mu^r_{max}} \varphi(\mu^r) r(t, \mu^r) d\mu^r + \int_{\mu^s_{min}}^{\mu^s_{max}} \varphi(\mu^s) s(t, \mu^s,) d\mu^s, \quad (15)$$

where $\varphi(\mu)$ is the function describing the number of TfR on a cell with cell age $\mu$, $r(t, \mu^r)$ is the density of erythroblasts, and $s(t, \mu^s)$ is the density of bone marrow reticulocytes.

7.2.1. Function for the Transferrin Receptors.

Assumptions 35-39 govern the development of the transferrin receptors. One ensures that Assumptions 35-38 are met by choosing a polynomial of degree 3

$$\varphi(\mu) = a_4 \mu^3 + b_4 \mu^2 + c_4 \mu + d_4$$

and choosing the coefficients $a_4$, $b_4$, $c$ and $d_4$ such that the function $\varphi$ satisfies the following conditions:

$$\varphi(0) = 30, \varphi(1.5) = 80, \varphi(1.5) = 0, \varphi(5) = 10. \quad (16)$$

For computational reasons, the number of TfR is multiplied by $10^{-4}$. Then the first condition in eq. (16) coincides with Assumption 36. The second and third condition reflect Assumption 37 and, with the last condition, one ensures that there is a smooth transition in the number of TfR from erythroblastic cells to reticulocytes. Deriving and solving the linear system that arises from eq. (16) gives $a_4 = 3.3016$ $b_4 = -32.127$ $d_4 = 30$. Further, using Assumption 38, the function ø can be extended to bone marrow reticulocytes. Altogether, one has $$\varphi(u) = \quad (17)$$

$$\begin{cases} 3.3016 \ \mu^3 - 32.127 \ \mu^2 + 74.0952 \ \mu + 30, & \text{for } \mu \in [\mu^r_{min}, \mu^r_{max}], \\ 10, & \text{for } \mu \in [\mu^s_{min}, \mu^s_{max}] \end{cases}$$

7.2.2. Accumulation of Hemoglobin

Red blood cells carry hundreds of hemoglobin molecules which enables them to carry oxygen. Hemoglobin has four subunits each containing a heme group. An iron atom is embedded in the middle of the heme group. Hence, in one hemoglobin molecule four iron atoms are incorporated. In order to keep track of the accumulation of hemoglobin molecules in the precursor cells, the development of the TfR and the amount of iron available at certain times have to be considered. A consequence of Assumption 35 is that cells with the same cell age all carry the same amount of hemoglobin. The amount of hemoglobin a cell with $\bar{u}$ accumulated can vary over time t but is invariant among cells with age $\bar{u}$ at a specific time t. First, one focuses on the erythroblast population class, where one has the special case that the maturation velocity $v \equiv 1$, i.e. the cell age and the time for how long a cell has been an erythroblast, and thus had time to accumulate hemoglobin, coincide. Hereinafter, the actual age of the cell, i.e. the time that elapsed since the cell became a precursor cell, will be called calendric age. This is to emphasize the difference between the cell age and the actual age, i.e. the calendric age.

The rate with which hemoglobin increases in a cell is given by $$\frac{d}{dt}(h(t, \mu(t))) = \frac{\partial}{\partial t} h t, \mu(t)) + \frac{\partial}{\partial \mu} h(t, \mu(t)) v(E(t)) = d\varphi(\mu(t)) \frac{a_1(t)}{TBV}, \quad (18)$$

where $h(t, \mu(t))$ denotes the amount of hemoglobin in a cell with $\mu$ (t) at time t. Note that, in most cases, the dependence of the cell age $\mu$ on time t is not explicitly stated, because there is no necessity to do so. Here, one has to consider this fact, as it is important for the derivation of the function h. Further, d is a rate constant which is different from $d_1$ because here one considers hemoglobin instead of iron, see eq. (14). The ratio between d and $d_1$ is given by the fact that each hemoglobin molecule consists of four iron atoms. The function $\varphi(\mu)$ is determined by eq. (17), $\alpha_1(t)$ describes the amount of iron in the plasma compartment and TBV denotes the total blood volume. For a detailed description of how the amount of hemoglobin in a cell with age $\mu$ at time t can be calculated from eq. (18).

Maturation velocity $v \equiv 1$

Cells in the erythroblast population class in the Erythropoiesis Model satisfy the condition that cell age and calendric age of the cell coincide, see Section 6. This makes it easier to keep track of the accumulation of hemoglobin. In order to calculate the amount of hemoglobin a cell with cell age $\mu$ at time t carries, one has to consider that the cell entered the population class at time $t - \mu + \mu_{min}$, where $\mu_{min}$ denotes the minimal cell age of the population class. Further, the amount of TfR on the cell membrane of the cell that entered the population at time $t - \mu + \mu_{min}$ was $\varphi(\mu_{min})$ and the amount of iron in plasma at that time was $\alpha_1(t - \mu + \mu_{min})$. With these considerations, the amount of hemoglobin a cell with cell age .mu. at time t carries is given by the following integral $$h(\bar{t}, \bar{\mu}) = \frac{d}{TBV} \int_{\bar{t} - \bar{\mu} + \mu_{min}}^{\bar{t}} \varphi(s - \bar{t} + \bar{\mu}) a_1(s) ds$$

Note that the calculation makes use of the history of the available amount of iron in plasma from $t - \mu + \mu_{min}$ to t.

For the erythroblast population (the cell age was transformed such that $\mu^r_{min} = 0$) the above equation simplifies to $$h(t, \mu^r) = \frac{d}{TBV} \int_{t-\mu^r}^{t} \varphi(s - t + \mu^r) a_1(s) ds. \quad (19)$$

Maturation velocity $v = v(E(t))$

In the case that cells have a variable maturation velocity, it gets more difficult to keep track of the accumulation of hemoglobin. First, one has to calculate at which time $\varphi$ t̂ a cell that has cell age $\bar{\mu}$ at time $\bar{t}$ entered the population class. Therefore, the following equation has to be solved with regard to $\hat{t}$ $$\bar{\mu} = \mu_{min} + \int_{\hat{t}}^{\bar{t}} v(E(s))ds$$

i.e., one has to (numerically) find the root of the following function $$f(\hat{t}, \bar{\mu}) = \mu_{min} - \bar{\mu} + \int_{\hat{t}}^{\bar{t}} v(E(s))ds. \quad (20)$$

The value $\eta = \bar{t} - \hat{t}$ reflects the calendric age of the cell. (It represents the time that passed since the cell entered the population class and does not necessarily coincide with the cell age/maturity of the cell.)

In the Erythropoiesis model presented in Section 6, only the reticulocyte population has a variable maturation velocity. Assumption 39 states that cells in this specific population class express a constant number of TfR on their membranes. For the sake of simplicity, the special case $\varphi \equiv const$ is considered here, and the general case when $\varphi = (\mu)$ is not considered.

Thus, the amount of hemoglobin in a reticulocyte with calendric age $\eta^s \in [5,8]$ at Time t is given $$h(t, \eta^s) = h(t - \eta^s + \mu^s_{min}, \mu^r_{max}) + \varphi \frac{d}{TBV} \int_{t-\eta^s+\mu^s_{min}}^{t} a_1(s)ds. \quad (21)$$

The calendric age of the cell has been derived using the solution of eq. (20) and $h(t-\eta^s+\mu^s_{min}, \mu^r_{max})$ is derived from eq. (19).

7.2.3 Rate of Apoptosis of Precursor Cells

The construction of the rate of apoptosis of precursor cells is inspired by the fact that cells that do not synthesize hemoglobin sufficiently are more likely to die. See Schmidt.

Hereinafter, one is going to refer to cell age of the erythroblasts and the calendric age (see eq. 20) of the reticulocytes, respectively, as $\eta$. Consequently, $\eta \in [0,8]$ and denotes the time that elapsed since a cell became a precursor cell.

First, a "reference hemoglobin accumulation curve" denoted by $h^*(\eta)$ is created using eqs. (19) and (21). The construction is based on an average male healthy adult, assuming that: the person's erythropoiesis and iron homeostasis is in steady state, the total blood volume is 5 liters, and the amount of iron in plasma is 3 mg, i.e., $\alpha_1 \equiv 3$.

Further, healthy persons produce normocytic red blood cells and the amount of Hgb per cell lies within 26-32 pg. The contact rate d is chosen such that, under the above assumptions and by applying eqs. (19) and (21), respectively, the hemoglobin content of a cell lies well within this range when the cell leaves the reticulocyte population and enters the blood stream. Note that the label 'days since cell became a precursor cell' is similar to the calendric age .eta. and for erythroblast (day 0-5) coincides with the cell age, whereas for the reticulocytes the cell age and the calendric age might differ. Reticulocytes may stay in the bone marrow 1-3 days, but they all leave the bone marrow when they reach maximal maturity, i.e., when their cell age turns 2. This means that reticulocytes might have different timespans to gather iron and synthesize hemoglobin—depending on the maturation velocity $v(E(t))$, see Section 6.

Next, the reference curve is shifted, by slightly reducing or increasing, respectively, the amount of iron in plasma ($\alpha_1 \equiv 2.75$ mg and $\alpha_1 \equiv 3.25$ mg, respectively). The consequence being that a corridor develops around the reference curve. The next step is to design functions in a way that cells that leave this corridor are more likely to die, the farther they diverge from it, the higher the rate of apoptosis gets. A family of functions is created that describes this increase in mortality as cells diverge from the reference curve $$\aleph(h, \eta) = \left(\frac{c_\aleph}{(\eta+1)^3}\right)(h - h^*(\eta))^4 \quad (22)$$

where $c_\aleph$ is a constant, h denotes the amount of hemoglobin that a cell carries at cell age/calendric-age $\eta$ and $h^*$ is the reference hemoglobin value at the age $\eta$. Polynomial functions of degree 4 are used to design this function, because one of their characteristics is that they have a flat bottom (i.e. apoptosis within the corridor is low) and then increase sharply. Finally, to get the rate of apoptosis $\alpha$ for the precursor cells, a discrete set of N+1 equidistant data points $\mu_i, i=0, N$ are defined along $\mu \in [\mu_{min}^r, \mu_{max}^s]$ at which the following calculations are done calculate the amount of Hgb kin cells of age $\mu_i$ using eq. (19), (20) and (21), calculate the values of the function $\aleph$ at the grid points $\eta_i$ and the corresponding Hgb value $h_i$ interpolate the resulting values using cubic splines. The result is the function $\alpha(h,\eta)$ describing the rate of apoptosis of precursor cells. Note that the above calculations have to be repeated at every time step.

7.3. Detailed Description of the Iron Compartments.

7.3.1. Plasma (Compartment 1).

The rate at which iron enters erythroid cells at time t is given by $$d_1 a_1(t)\tau(t)$$

where the number of transferrin receptors $\tau$ on all precursor cells is $$\tau(t) = d_1 \left( \int_{\mu_{min}^r}^{\mu_{max}^r} \varphi(\mu^r) r(t, \mu^r) d\mu^r + \int_{\mu_{min}^s}^{\mu_{max}^s} \varphi(\mu^s) s(t, \mu^s) d\mu^s \right)$$

where $\varphi(\mu)$ is given by eq. (17). Further, $r(t,\mu^r)$ and $s(t,\mu^s)$ denote the population densities of hemoglobin synthesizing cells, erythroblasts and reticulocytes, respectively. At the same time this is the rate at which iron leaves the plasma compartment and enters the precursor cell compartment.

Only a very small amount of iron can be found in this pool (about 3 mg; .ltoreq.1%) bound to transferrin, but it is a very important compartment because of its rapid turnover rate. See Finch 1982. Iron normally turns over at least 10 times each day. See Williams Hematology. Inflow into the plasma compartment comes from macrophages, the storage pool, iron absorbed through the duodenum, and via intravenously administered iron. Outflow leaves the plasma compartment to the precursor cells and the storage compartment. The flow rates $k_{41}$, $k_{gastro,1}$ and $k_{51}$ are dependent on the hepcidin concentration H(t) at time t. They decrease when the hepcidin level rises and vice versa. Inflammation and full iron stores increase the release of hepcidin from the hepatocytes in the liver, whereas a stressed erythropoiesis and depleted stores suppress the production of hepcidin. The outflow to the precursor cell compartment $k_{12}a_1$ is altered by the amount of iron needed from the cells to synthesize hemoglobin. As erythroid cells are only able to take up iron through transferrin receptors, their need for iron can be associated with the number of receptors expressed on precursor cells. Thus, the rate $k_{12}$ is given by $$k_{12} = \int_{\mu_{min}^r}^{\mu_{max}^r} \varphi(\mu^r) r(t, \mu^r) d\mu^r + \int_{\mu_{min}^s}^{\mu_{max}^s} \varphi(\mu^s) s(t, \mu^s) d\mu^s \qquad (15)$$

For an explanation of the various terms see the statements about erythroblasts in Section 6.2. Hence, the change of amount of iron in the plasma compartment is $$\frac{d}{dt} a_1 = k_{41}(H(t)) a_4(t) + a_{iv,total}(t) \delta_{t_0}(t) +$$
$$k_{gastro,1}(H(t)) a_{gastro}(t) + k_{51}(H(t)) a_5(t) - k_{15} a_1(t) -$$
$$d_1 \left( \int_{\mu_{min}^r}^{\mu_{max}^r} \varphi(\mu^r) r(t, \mu^r) d\mu^r + \int_{\mu_{min}^s}^{\mu_{max}^s} \varphi(\mu^s) s(t, \mu^s) d\mu^s \right) a_1(t).$$

The transfer rate $k_{41}(H(t))$ and $k_{51}(H(t))$ can be described by monotonically decreasing sigmoidal functions $$k_{41}(H(t)) = \frac{a_6 - b_6}{1 + e^{-k_6 H(t) + c_6}} + b_6, \qquad (23)$$

and $$k_{51}(H(t)) = \frac{a_7 - b_7}{1 + e^{-k_7 H(t) + c_7}} + b_7, \qquad (24)$$

respectively. The parameters $a_6$, $b_6$, $c_6$, $k_6$, $a_7$, $b_7$, $c_7$ and $k_7$ are positive constants with $a_6 > b_6$ and $a_7 > b_7$. The hepcidin level H(t) at time t is determined by eq. (13).

7.3.2. Precursor Cells (Compartment 2).

Inflow into the precursor cell compartment comes from plasma. One outflow of this compartment leaves to the erythrocytes compartment and describes the amount of hemoglobin carried from reticulocytes, which enter the blood stream. Thus, the flow $f_{23}(\cdot)$ from compartment 2 to compartment 3, is defined by the cells that leave the bone marrow and the amount of hemoglobin these cells are carrying. First, one has to compute how long cells that leave the bone marrow at time t have actually stayed there as precursor cells. Hence, one needs to solve $f(t, \mu_{max}^s)$ and one denotes the root of eq. (20) by $\eta_{max}^s$. Note that $\eta^{smax}$ might change over time as reticulocytes are released in the blood stream faster or more slowly.

$$k_{23}a_2 = f_{23}(v^s(E(t)) s(t,\mu_{max}^s), h(t,\mu_{max}^s)),$$

where $v^s(E(t)) s(t, \mu_{max}^s)$ determines how many reticulocytes are leaving the bone marrow at a certain time t and the function $h^s(t, \eta_{max}^s)$ indicates how much hemoglobin they carry. $v^s(E(t))$ is the maturation velocity of reticulocytes depending on EPO and $s(t, \mu_{max}^s)$ is the density of the reticulocyte population with maximal maturity $\mu_{max}^s$ at time t. The function $h^s(t, \eta_{max}^s)$ is given by eq. (21).

The second outflow of this compartment leaves to the macrophages and is defined by the precursor cells that die. Hence, the flow from compartment 2 to compartment 4 is defined by the amount of iron that dying cells carry, i.e.

$$k_{24} a_4 = \int_{\mu_{min}^r}^{\mu_{max}^r} \alpha(h, \mu^r) h(t, \mu^r) r(t, \mu^r) d\mu^r + \qquad (25)$$
$$\int_{\eta_{min}^s}^{\eta_{max}^s(t)} \alpha(h, \eta^s) h(t, \eta^s) s\left(t, \mu_{min} + \int_{t-\eta^s}^{t} v(E(s)) ds\right) d\eta^s.$$

For the first part of the above equation, $\eta$ and $\mu^r$ are exchangeable without any difficulties as, for erythroblasts, both describe the cell age of the cell, see Section 6.2.

Altogether the change of amount of iron in the iron-precursors compartment is given by $$\frac{d}{dt} a_2(t) = d_0 \left( \int_{\mu_{min}^r}^{\mu_{max}^r} \varphi(\mu^r) r(t, \mu^r) d\mu^r + \int_{\mu_{min}^s}^{\mu_{max}^s} \varphi(\mu^s) s(t, \mu^s,) d\mu^s \right) a_1(t) -$$
$$f_{23}(v^s(E(t)) s(t, \mu_{max}^s), h^s(t, \mu_{max}^s)) - \int_{\mu_{min}^r}^{\mu_{max}^r} \alpha(h, \mu^r) h(t, \mu^r) r(t, \mu^r) d\mu^r -$$
$$\int_{\eta_{min}^s}^{\eta_{max}^s(t)} \alpha(h, \eta^s) h(t, \eta^s) s\left(t, \mu_{min} + \int_{t-\eta^s}^{t} v(E(s)) ds\right) d\eta^s.$$

Note that it is not necessary to determine the function $f_{23}$ as, in fact, there is no need to explicitly observe the rate of change of the precursor cell compartment. The amount of iron $\alpha^2(t)$ in this compartment at time t can be directly computed from eqs. (19), (20), (21), and the population equations for the erythroblasts and reticulocytes. It is defined by the total number of precursor cells and the amount of hemoglobin they carry:

$$a_2(t) = \int_{\mu_{min}^r}^{\mu_{max}^r} \alpha(h, \mu^r) r(t, \mu^r) d\mu^r +$$
$$\int_{\eta_{min}^s}^{\eta_{max}^s(t)} \alpha(h, \eta^s) h(t, \eta^s) s\left(t, \mu_{min} + \int_{t-\eta^s}^{t} v(E(s)) ds\right)$$

However, it is important to know the flux of hemoglobin to the macrophage compartment, which arises from dying cells, because this flux (see eq. (25)) is a source term in the macrophage compartment.

7.3.3. Erythrocytes (Compartment 3)

Inflow into the erythrocytes compartment comes from the precursor cell compartment, and iron leaves the compartment to the macrophages compartment (phagocytosis of senescent cells, random break-down of cells and neocytolysis)

$$k_{34} a_3 = \int_{\mu_{min}^m}^{\mu_{max}^m} h(t - \mu^m, \eta_{max}) \alpha^m(E(t), \mu^m) m(t, \mu^m) d\mu^m, \qquad (26)$$

or is excreted via bleeding $$k_{3,out}a_3 = \int_{\mu_{min}^m}^{\mu_{max}^m} h(t-\mu^m, \eta_{max}^s)\alpha_{bleed}^m(t)m(t,\mu^m)d\mu^m$$

An erythrocyte of age $\mu^m$ left the reticulocyte population at time $t-\mu^m$ and, making use of Assumption 42, the amount of hemoglobin it carries can be computed using eq. (21). Further, $\alpha^m$ denotes the mortality rate of erythrocytes due to phagocytosis of senescent cells, random break-down of cells, and neocytolysis. Furthermore, h is the amount of hemoglobin carried by a cell, $m(t, \mu^m)$ is the population density of erythrocytes with cell age $\mu^m$ at time t, and $\alpha^m{}_{bleed}$ is the rate with which RBCs are lost due to bleeding.

Thus, the change of the amount of iron in the erythrocyte compartment is $$\frac{d}{dt}a_3(t) = f_{23}(v^s(E(t))s(t,\mu_{max}^s), h^s(t,\mu_{max}^s)) -$$

$$\int_{\mu_{min}^m}^{\mu_{max}^m} h(t-\mu^m, \eta_{max}^s)\alpha^m(E(t),\mu^m)m(t,\mu^m)d\mu^m -$$

$$\int_{\mu_{min}^m}^{\mu_{max}^m} h(t-\mu^m, \eta_{max}^s)\alpha_{bleed}^m(t)m(t,\mu^m)d\mu^m.$$

Similar to compartment 2, it is not necessary to observe the rate of change of the erythrocyte cell compartment to compute the amount of iron $\alpha_3(t)$ at time t. The quantity $\alpha_3(t)$ can be directly computed from the population class and is defined by the total number of circulating red blood cells and the amount of hemoglobin they carry:

$$a_3(t) = \int_{\mu_{min}^m}^{\mu_{max}^m} h(t-\mu^m, \eta_{max}^s)m(t,\mu^m)d\mu^m$$

However, the term $k_{34}\alpha_3(t)$ needs to be known explicitly (see eq. (26)). This flux, which is the rate of hemoglobin released by erythrocytes, appears as a source term in the macrophage compartment.

7.3.4 Macrophages (Compartment 4)

Inflow into the macrophages compartment comes from the erythrocytes compartment (erythrocytes phagocytosed by macrophages, iron set free by random break-down of RBCs and shedding of hemoglobin containing vesicles) and the precursor cells compartment. Outflow of this compartment leaves to the plasma and to the storage compartment. Therefore, the change of iron in the compartment is $$\frac{d}{dt}a_4(t) = \int_{\mu_{min}^r}^{\mu_{max}^r} \alpha(h,\mu^r)h(t,\mu^r)r(t,\mu^r)d\mu^r +$$

$$\int_{\mu_{min}^s}^{\eta_{max}(t)} \alpha(h,\eta^s)h(t,\eta^s)s\left(t, \mu_{min} + \int_{t-\eta^s}^{t} v(E(s))ds\right)d\eta^s +$$

$$\int_{\mu_{min}^m}^{\mu_{max}^m} h(t-\mu^m, \eta_{max}^s)\alpha^m(E(t),\mu^m)m(t,\mu^m)d\mu^m -$$

$$k_{41}(H(t))a_4(t) - k_{45}a_4(t),$$

where $k_{41}(H(t))$ is given by eq. (23).

7.3.5. Storage (Compartment 5)

Inflow into the storage compartment comes from the plasma and the macrophages compartment and iron leaves this compartment to the plasma compartment. Hence, the change of iron in the storage compartment is $$\frac{d}{dt}a_5(t) = k_{15}a_1(t) + k_{45}a_4(t) - k_{51}(H(t))a_5(t)$$

where $k_{51}(H(t))$ is given in eq. (24).

7.4. Mathematical Model Iron Model

For the convenience of the reader, all equations of the Iron Model are collected in this section:

$$\frac{d}{dt}a_1(t) =$$
$$k_{41}(H(t))a_4(t) + a_{iv,total}(t)\delta_{t_0}(t) + k_{gastro,1}(H(t))a_{gastro}(t) + k_{51}(H(t))a_5(t) -$$
$$k_{15}a_1(t) - d_1\left(\int_{\mu_{min}^r}^{\mu_{max}^r}\varphi(\mu^r)r(t,\mu^r)d\mu^r + \int_{\mu_{min}^s}^{\mu_{max}^s}\varphi(\mu^s)s(t,\mu^s)d\mu^s\right)a_1(t),$$

$$a_2(t) = \int_{\mu_{min}^r}^{\mu_{max}^r}\alpha(h,\mu^r)r(t,\mu^r)d\mu^r +$$
$$\int_{\mu_{min}^s}^{\eta_{max}^s(t)}\alpha(h,\eta^s)h(t,\eta^s)s\left(t,\mu_{min}+\int_{t-\eta^s}^{t}v(E(s))ds\right)d\eta^s$$

$$a_3(t) = \int_{\mu_{min}^m}^{\mu_{max}^m} h(t-\mu^m,\eta_{max}^s)m(t,\mu^m)d\mu^m$$

$$\frac{d}{dt}a_4(t) = \int_{\mu_{min}^r}^{\mu_{max}^r}\alpha(h,\mu^r)h(t,\mu^r)r(t,\mu^r)d\mu^r +$$
$$\int_{\mu_{min}^s}^{\eta_{max}^s(t)}\alpha(h,\eta^s)h(t,\eta^s)s\left(t,\mu_{min}+\int_{t-\eta^s}^{t}v(E(s))ds\right)d\eta^s +$$
$$\int_{\mu_{min}^m}^{\mu_{max}^m} h(t-\mu^m,\eta_{max}^s)\alpha^m(E(t),\mu^m)m(t,\mu^m)d\mu^m -$$
$$k_{41}(H(t))a_4(t) - k_{45}a_4(t),$$

$$\frac{d}{dt}a_5(t) = k_{15}a_1(t) - k_{51}(H(t))a_5(t),$$

$$\frac{d}{dt}H(t) = \frac{1}{TBV}H_{prod}(t) - c_{deg}^H H(t)$$

where the initial values are given by $a_1(0) = a_{1,0}$, $a_2(0) = a_{2,0}$, $a_3(0) = a_{3,0}$, $a_4(0) = a_{4,0}$, $a_5(0) = a_{5,0}$, $H(0) = H_0$.

Moreover, a number of auxiliary equations are needed $$k_{gastro,1}(H(t)) = \frac{a_5 - b_5}{1 + e^{-k_5 H(t) + c_5}} + b_5,$$

$$k_{41}(H(t)) = \frac{a_6 - b_6}{1 + e^{-k_6 H(t) + c_6}} + b_6,$$

-continued $$k_{51}(H(t)) = \frac{a_7 - b_7}{1 + e^{-k_7 H(t) + c_7}} + b_7,$$

where the hepcidin feedback is given by $$H_{prod}(t) = \frac{a_H - b_H}{1 + e^{-k_H C(t) + c_H}} + b_H,$$

$$C(t) = -c_U U(t) + c_{a_5} a_5(t) + c_i i(t),$$

$$U(t) = \int_{\mu^r_{min}}^{\mu^r_{max}} r(t, \mu^r) d\mu^r + \int_{\mu^s_{min}}^{\mu^s_{max}} s(t, \mu^s) d\mu^s$$

Furthermore, we have $$\varphi(\mu) = \begin{cases} 3.3016\,\mu^3 - 32.127\,\mu^2 + 74.0952\,\mu + 30, & \text{for } \mu \in [\mu^r_{min}, \mu^r_{max}], \\ 10, & \text{for } \mu \in [\mu^s_{min}, \mu^s_{max}] \end{cases}$$

$$h(t, \mu^r) = \frac{d}{TBV} \int_{t-\mu^r}^{t} \varphi(s - t + \mu^r) a_1(s) ds$$

$$h(t, \eta^s) = h(t - \eta^s + \mu^s_{min}, \mu^r_{max}) + \phi \frac{d}{TBV} \int_{t-\eta^s+\mu^s_{min}}^{t} a_1(s) ds.$$

The calendric age η of cells is calculated using $$f(\hat{t}, \overline{\mu}) = \mu_{min} - \overline{\mu} + \int_{\hat{t}}^{\overline{t}} v(E(s)) ds,$$

and η=t−t̂.

Further, to create the function α(hη) (for η either $\mu^r$ or $\eta^s$ can be inserted) a discrete set of N+1 equidistant data points $\mu_i, \ldots, N$, along $\mu \in [\mu_{min}{}^r, \mu_{max}{}^r]$ is defined and at every time step the following calculations are done calculate the amount of Hgb $h_i$ in cells of age $\mu_i$ using the formula for η, $f(t,\mu)$, $h(t,\mu^r)$ and $h(t,\mu^s)$, calculate the values of the function ℵ at the grid points $\eta_i$ and the corresponding Hgb value $h_i$ $$\aleph(h, \eta) = \left(\frac{c_\aleph}{(\eta+1)^3}\right)(h - h^*(\eta))^4$$

interpolate the resulting values using cubic splines.
Derivation of Population Equations
A.1. Population Equations with One Structural Variable.
Let u(t,•) denote the density of the population at time t, i.e., for 0≤a<b is the number of cells with maturity level $\int_a^b u(t,x)dx$. The rate of change is $$\frac{d}{dt}\int_a^b u(t, x) dx = \int_a^b u_t(t, x) dx, \, t \geq 0, \, 0 \leq a < b.$$

Here, u is assumed to be continuously differentiable with respect to t. The rate of change with respect to t of the number of cells with maturity level in [a,b] is the sum of several components: the flux of cells across the boundary points a and b at time t because of changing maturity; the rate at which cells with maturity in [a,b] die at time t; the rate at which cells with maturity in [a, b] proliferate.

a) Flux Across a and b.

The flux of cells across maturity level is denoted x at time t by q(t,x) and assume that the maturity of a cell is changing according to $$\dot{x}(t) = v(t, x(t)), t \geq 0$$

where the "velocity" v is continuous in t and Lipschitzean with respect to x, t≥0, 0≥0. Moreover, it is assumed that v(t,x)>0, i.e., the maturity of a cell is always strictly increasing.

Then the flux of cells across a maturity level x is given by $$q(t,x) = v(t,x)u(t,x), t \geq 0, x \geq 0$$

Consequently, the net flux of cells at time t into the interval [a, b] is $$q(t, a) - q(t, b) = \quad\quad\quad\quad\quad\quad\quad\quad (A.2)$$
$$v(t, a)u(t, a) - v(t, b)u(t, b) = -\int_a^b ((v(t, x)u(t, x))_x dx, \, t \geq 0.$$

b) Mortality.

Let $x_i^N = a + \Delta x$, i=0, ..., N with Δx=(b−a)/N be a uniform mesh on [a,b]. By the mean value theorem for integrals, the number of cells with maturity level x∈$[x_i^N, x_{i+1}^N]$ at time t for some $x_i^* \in [x_i^N, x_{i+1}^N]$ is given by $$u(t,x_i^*)\Delta x.$$

The rate at which cells with maturity in $[x_i^N, x_{i+1}^N]$ die at time t is assumed to be proportional to the number of cells with maturity in this interval and therefore is given by $$\alpha(t, x_i^{**})u(t, x_i^*)\delta x,$$

where α(t,x)≥0, t≥0, x≥0, is the mortality rate which is assumed to be a continuous function and xi**∈$[x_{Ni}, x^N_i+1]$. Summing i=0, ..., N−1 and taking N→∞ yields $$\int_a^b \alpha(t,x)u(t,x)dx, t \geq 0, \quad\quad\quad\quad (A.3)$$

for the rate at which cells with maturity level in [a,b] die at time t.

c) Proliferation.

The assumption concerning proliferation is that a cell with maturity level x dividing at time t gives rise to two daughter cells with maturity x. By analogous considerations as in the case of mortality, the following expression is obtained for the rate at which cells enter the interval [a,b] at time t because of proliferation:

$$2\int_a^b \beta(t,x)u(t,x)dx - \int_a^b \beta(t,x)u(t,x)d = \int_a^b \beta(t,x)u(t,x)dx,$$
$$t \geq 0, \quad\quad\quad\quad\quad\quad\quad\quad (A.4)$$

where β(t,x)≥0 t≥0, x≥0, is the proliferation rate in the population which is assumed to be continuous.
d) The Model.
Using (A.1)-(A.4) yields $$\int_a^b u_t(t, x)dx = -\int_a^b \bigl((v(t, x)u(t, x))_x dx - \quad (A.4)$$
$$\int_a^b \alpha(t, x)u(t, x)dx + \int_a^b \beta(t, x)u(t, x)dx, \, t \geq 0, \, x \geq 0.$$

Assuming that the integrands in the above integrals are continuous and observing that the interval [a, b]⊂$R_+$ is arbitrary yields $$u_t(t,x) + ((v(t,x)u(t,x))_x = (\beta(t,x) - \alpha(t,x))u(t,x), t \geq 0, x \geq 0. \quad (A.5)$$

In addition to this equation, an initial condition needs to be prescribed as $$u(0,x)=u_0(x), x \geq 0$$

and a boundary condition for x=0. Assuming v(t, 0)>0, t≥0, this boundary condition is written as a flux condition at x=0:

$$v(t,0)u(t,0)=f_0(t), t \geq 0.$$

A.2. Population Equations with Several Structural Variables.

Models for populations structured by several attributes can be derived analogously to those for populations with just one attribute. For simplicity of notation, populations are restricted to three structural variables and cell populations with the attributes cell age x, amount of hemoglobin in the cell y, and amount of transferrin receptors on the cell membrane z are considered.

Let u(t,x,y,z) be the density of the cell population and $\Omega$ be a subset of the positive cone $R^3_+$ in $R^3$ which is the admissible set for the attributes. Then the number of cells with attributes (x,y,z)∈$\Omega$ at time t is given by $$\int_\Omega u(t,x,y,z)d\omega.$$

Of interest is the rate at which the number of cells with attributes in $\Omega$ at time t changes, i.e., in the quantity $$\frac{d}{dt}\int_\Omega u(t, x, y, z)d\omega = \int_\Omega u_1(t, x, y, z)d\omega, \quad (A.6)$$

where it is assumed that u is continuously differentiable with respect to t. The rate at which the number of cells with attributes in $\Omega$ changes at time t is composed of several components: the flux of cells across $\partial \Omega$ because the attributes change; the rate at which cells with attributes in $\Omega$ die at time t; the rate at which cells enter or leave $\Omega$ at time t because of proliferation.

a) Flux Across $\partial \Omega$.

The attributes of a cells change according to $$\dot{x}(t)=f(t,x(t),y(t),z(t)),$$

$$\dot{y}(t)=g(t,x(t),y(t),z(t)),$$

$$\dot{z}(t)=h(t,x(t),y(t),z(t)), \quad (A.7)$$

where $f$, g, h are functions $R_+ \times R^3_+ \to R$ which are continuous with respect to t and Lipschitzean with respect to x, y, z. Then the flux of cells at time t and at (x, y, z)∈$R^3_+$ is given by $$F(t, x, y, z) = u(t, x, y, z)\begin{pmatrix} f(t, x, y, z) \\ g(t, x, y, z) \\ h(t, x, y, z) \end{pmatrix}$$

Consequently the flux of cells across $\partial \Omega$ at time t is given by $$\int_{\partial\Omega}\langle F(t,x,y,z), v(x,y,z)\rangle d\sigma, \quad (A.8)$$

where v(x,y,z) denotes the unit outside normal to $\partial \Omega$ at the point (x,y,z). By Gauss' integral theorem we get $$\int_{\partial\Omega}\langle F(t, x, y, z), v(x, y, z)\rangle d\sigma = \quad (A.9)$$

-continued
$$\int_\Omega div F(t, x, y, z) d\omega = \int_\Omega ((f(t, x, y, z)u(t, x, y, z))_x +$$
$$(g(t, x, y, z)u(t, x, y, z))_y + (h(t, x, y, z)u(t, x, y, z))_z)d\omega.$$

b) Mortality.

Let $\Omega = \cup_{i=1}^N \Omega_i$ such that diam $\Omega_i < \epsilon$, i=1, ..., N. By the mean value theorem for integrals, the number of cells with attributes in $\Omega_i$ at time t is given by $\mu(t, x_i^*, y_i^* z_i^*)\Delta\Omega_i$, where $\Delta\Omega_i$ denotes the volume of $\Omega_i$ and $(x_i^*, y_i^*, z_i^*)\Delta\Omega_i$. It is assumed that the rate at which cells with attributes in $\Omega_i$ die at time t is proportional to the number of cells with attributes in $\Omega_i$ at time t, i.e., it is given by $$\alpha(t, x_i^{}, y_i^{}, z_i^{**})u(t, x_i^*, y_i^*, z_i^*)$$

where $(x_i^{}, y_i^{}, z_i^{**})$, $(x_i^*, y_i^*, z_i^*) \in \Omega_i$ and $\alpha(t,x,y,z)$ is the mortality rate, i.e., the rate at which cells with attributes (x,y,z) die at time t. Summing up and taking .epsilon..fw-darw.0, the rate at which individuals with attributes in $\Omega$ die at time t is given by $$\int_\Omega \alpha(t,x,y,z)u(t,x,y,z)d\omega. \quad (A.10)$$

c) Proliferation.

A basic assumption for proliferation is that division at time t of a cell with cell age x, amount of hemoglobin y and amount of transferrin receptors z results in two cells each with cell age x, amount of hemoglobin y/2 and amount of transferrin receptors z/2. Furthermore, the rate at which cells with attributes (x,y,z) divide at time t is assumed to be given by $\beta(t,x,y,z)$.

For a subset $\Omega \subset R^3_+$ the subsets $$\Omega^{(\frac{1}{2})},$$

$\Omega^{(2)} \subset R^3_+$ are defined by $$\Omega^{(\frac{1}{2})} = \{(x, y, z) \mid (x, 2y, 2z) \in \Omega\}, \Omega^{(2)} = \left\{(x, y, z) \mid \left(x, \frac{y}{2}, \frac{z}{2}\right) \in \Omega\right\}$$

From now on, it is assumed that $$\Omega^{(\frac{1}{2})} \cap \Omega = \phi \text{ and } \Omega^{(2)} \cap \Omega = \phi. \quad (A.11)$$

The following results are important when the equations governing the development of a structured population are derived:

Lemma A.1 For any $(x_0,y_0,z_0)\in R^3_+$ with $y_0 > 0$ or $z_0 > 0$ there exists a subset $\Omega \subset R^3_+$ with $(x_0, y_0, z_0)\in \Omega$ satisfying condition (A.11).

Proof. The case $y_0 > 0$ is the only case considered. For $$\varepsilon = \frac{y_0}{3} > 0$$

set $$\Omega = \{(x,y,z) \in R^3_+ \mid |x-x_0|<\epsilon, |y-y_0|<\epsilon, |z-z_0|<\epsilon\}$$

and assume that (x, y, z)∈$\Omega \cap \Omega^{(1/2)}$. By the definition of $\Omega^{(1/2)}$, this is equivalent to $$|x-x_0|<\epsilon, |y-y_0|<\epsilon, |2y-y_0|<\epsilon, |z-z_0|<\epsilon, \text{ and } |2z-z_0|<\epsilon$$

The inequalities for y and the definition of $\epsilon$ imply that $y > y_0 - \epsilon = 2y_0/3$ and $y(y_0+\epsilon)/2 = 2y_0/3$, a contradiction, which proves that $\Omega^{1/2} \cap \Omega = \emptyset$. The proof for $\Omega 2 \cap \Omega = \emptyset$ is analogous. The rate of change of the number of cells with attributes in $\Omega$ due to proliferation equals the rate at which the daughter cells of cells with attributes in $\Omega_2$ move into $\Omega$ the rate at which the daughter cells of cells with attributes in $\Omega$ leave $\Omega$ (and move to $\Omega^{(1/2)}$). By analogous considerations as in the case of the effect of mortality, the following expression is obtained for the rate at which the number of cells with attributes in $\Omega$. changes because of proliferation:

$$2\int_{\Omega^{(2)}} \beta(t,\tilde{x},\tilde{y},\tilde{z}) d\tilde{\omega} - \int_{\Omega} \beta(t,x,y,z) u(t,x,y,z) d\omega = 8\int_{\Omega} \beta(t,x,2y,2z) u(t,x,2y,2z) d\omega - \int_{\Omega} \beta(t,x,y,z) u(t,x,y,z) d\omega. \quad (A.12)$$

d) The model.

Using (A.6), (A.9), (A.10) and (A.12) yields $$\int_{\Omega} u_t(t,x,y,z) d\omega =$$
$$- \int_{\Omega} ((f(t,x,y,z) u(t,x,y,z))_x + (g(t,x,y,z) u(t,x,y,z))_y +$$
$$(h(t,x,y,z) u(t,x,y,z))_z) d\omega -$$
$$\int_{\Omega} (\alpha(t,x,y,z) + \beta(t,x,y,z)) u(t,x,y,z) d\omega +$$
$$8 \int_{\Omega} \beta(t,x,2y,2z) u(t,x,2y,2z) d\omega.$$

Assuming that the integrands in the above integrals are continuous and using Lemma 1 yields $$u_t(t,x,y,z) + (f(t,x,y,z) u(t,x,y,z))_x + \quad (A.13)$$
$$(g(t,x,y,z) u(t,x,y,z))_y + (h(t,x,y,z) u(t,x,y,z))_z =$$
$$-(\alpha(t,x,y,z) + \beta(t,x,y,z)) u(t,x,y,z) +$$
$$8\beta(t,x,2y,2z) u(t,x,2y,2z), \, t \geq 0, x > 0, y > 0, z > 0.$$

An initial condition is prescribed $$u(0,x,y,z) = u_o(x,y,z), x > 0, y > 0, z > 0$$

and boundary conditions which, because of their special form, are considered directly in Section 2.

A.3. List of Parameters for models described in Sections 6 and 7

TABLE 5

List of parameters and their meaning.

| Parameter | Meaning |
|---|---|
| $\beta^p$ | proliferation rate for BFU-E cells |
| $\beta^q$ | proliferation rate for CFU-E cells |
| $\beta^r$ | proliferation rate for erythroblasts |
| $\mu_{max}^p$ | maximal maturity for BFU-E cells |
| $\mu_{min}^q$ | minimal maturity for CFU-E cells |
| $\mu_{max}^q$ | maximal maturity for CFU-E cells |
| $\mu_{min}^r$ | minimal maturity for erythroblasts |
| $\mu_{max}^r$ | maximal maturity for erythroblasts |
| $\mu_{min}^r$ | minimal maturity for marrow reticulocytes |
| $\mu_{max}^r$ | maximal maturity for marrow reticulocytes |
| $\alpha_{rand}^m$ | intrinsic mortality rate for erythrocytes |
| $a_1, b_1, c_1, k_1$ | constants for the sigmoid apoptosis rate for CFU-E cells |
| $a_2, b_2, c_2, k_2$ | constants for the sigmoid maturation velocity for marrow reticulocytes |

TABLE 5-continued

List of parameters and their meaning.

| Parameter | Meaning |
|---|---|
| $d_1$ | rate constant for transferrin to bind to its receptor |
| $d$ | rate constant with which hemoglobin is synthesized after transferrin bound to the TfR |
| $a_3, b_3, c_3, k_3$ | constants for the sigmoid function governing the release of endogenous EPO |
| $\mu_{min}^{m,n}$ | lower bound of erythrocytes which are possibly exposed to neocytolysis |
| $\mu_{max}^{m,n}$ | lower bound of erythrocytes which are possibly exposed to neocytolysis |
| $\mu_{max}$ | maximal life span for erythrocytes |
| $C_E$ | constant in the mortality rate for erythrocytes |
| $\tau_E$ | EPO threshold for neocytolysis |
| $c_{deg}^{end}$ | degradation rate of EPO released by the kidneys |
| $c_{deg}^{ex}$ | degradation rate of administered EPO (Epoetin alfa) |
| $S_0$ | number of cells committing to the erythroid lineage |
| TBV | total blood volume |
| $a_4, b_4, c_4, k_4$ | constants for the polynomial function describing the number of TfR expressed on erythroblasts |
| $\eta$ | calendric age of the cell |
| $\eta^s$ | calendric age of the reticulocyte |
| $c_8$ | constant in the function describing the apoptosis rate for cells with age $\eta$ at time t |
| $h^*$ | reference hemoglobin value |
| $k_{ij}$ | transfer rates from iron compartment i to iron compartment j |
| $a_{iv}$ | the amount of iron administered intravenously |
| $a_{gastro}$ | the amount of iron in the duodenum |
| $a_5, b_5, c_5, k_5$ | constants for the sigmoid function governing the flow rate from the duodenum into the plasma compartment |
| $a_H, b_H, c_H, k_H$ | constants for the sigmoid function governing the release of hepcidin by the liver |
| $c_U, c_{a5}, c_i$ | constants for the auxiliary equation used in the sigmoid function governing the release of hepcidin by the liver |
| $c_{deg}^H$ | degradation rate of hepcidin |
| $a_6, b_6, c_6, k_6$ | constants for the sigmoid function describing the flow rate from the macrophages into the plasma compartment |
| $a_7, b_7, c_7, k_7$ | constants for the sigmoid function governing the flow rate from the storage into the plasma compartment |

A.4. Derivation of the Hgb Accumulation Function.

Let $h(t,\mu)$ respectively $\emptyset(\mu)$ denote the amount of hemoglobin in a cell of maturity $\mu \geq \mu_{min}$ at time $t \in R$ respectively the number of transferrin receptors on the membrane of a cell of maturity $\mu \geq \mu_{min}$. Then the rate at which $h(t,\mu)$ changes in time is given by $$\frac{d}{dt} h(t,\mu(t)) = \frac{\partial}{\partial t} h(t,\mu(t)) + \frac{\partial}{\partial t} h(t,\mu(t)) v(t) = d\emptyset(\mu(t)) a_1(t), \quad (A.4.1)$$
$$t \in R$$

where $d > 0$ is a constant, $\alpha_1(t)$ denotes the iron concentration in plasma at time t and $v(t)$ is the velocity at which the maturity of a cell increases, $v(t) = \mu(t)$. For equation (A.4.1) one has the boundary condition $$\mu(t,\mu_{min}) = 0, t \in R \quad (A.4.2)$$

We solve the problem (A.4.1), (A.4.2) using the method of characteristics. Let $s \to (t(s), \mu(s), u(s))$, $x \geq 0$ be the characteristic through a point $(t_0, \mu_{min}, 0)$. Then the functions $t(s)$, $\mu(s)$ and $u(s)$ are solutions of the following initial value problem ("prime(')"=d/ds):

$$t'(s) = 1, t(0) = t_0,$$

$$\mu'(s) = v(t(s)), \mu(0) = \mu_{min},$$

$$u'(s) = d\emptyset(\mu(s)) a_1(t(s)), u(0) = 0 \quad (A.4.3)$$

This gives, for $s \geq 0$, $t(s)=t_0+s$, (A.4.4)

$\mu(s)=\mu_{min}+\int_0^s v(t_0+\sigma)d\sigma$, (A.4.5)

$u(s)=h(t(s),\mu(s))=d\int_0^s \emptyset(\mu_{min}+\int_0^\sigma v(t_0+\rho)d\rho)a_1(t_0+\sigma)d\sigma$ (A.4.6)

In order to determine $h(\bar{t}, \bar{\mu})$ with $\bar{t} \in R$ and $\bar{\mu} \geq \mu_{min}$ one has to compute two numbers $\bar{s} \geq 0$ and $\hat{t} \in R$ such that $\bar{t}=t(\bar{s})$, $\bar{\mu}=\mu(\bar{s})$ and $h(\bar{t}, \bar{\mu})=u(\bar{s})$ where $t(\cdot)$, $\mu(\cdot)$ and $u(\cdot)$ solve system (A.4.3) with $t_0=\hat{t}$. From equations (A.4.4) and (A.4.5) for $s=\bar{s}$ we get $\hat{t}=\bar{t}-\bar{s}, \bar{\mu}=\mu_{min}+\int_0^{\bar{t}-\hat{t}} v(\hat{t}+\sigma)d\sigma=\mu_{min}+\int_{\hat{t}}^{\bar{t}} v(\sigma)d\sigma$.

This implies $\bar{s}=\bar{t}-\hat{t}$ and that $\hat{t}$ has to satisfy the equation $g(\hat{t})=\int_{\hat{t}}^{\bar{t}} v(\sigma)d\sigma=\bar{\mu}-\mu_{min}$ (A.4.3)

The function $\hat{t} \rightarrow g(\hat{t})$ is monotonically decreasing with $g(\bar{t})=0$. Equation (A.4.7) has a unique solution $\hat{t}<\bar{t}$ if, for instance, $v(t) \geq \delta$ for $t \in [T, \bar{t}]$ with $\delta T \geq \mu_{max}-\mu_{min}$ or if for some $t^* \in R$ one has $\int_{-\infty}^{t^*} v(\sigma)d\sigma=\infty$ In case $v \equiv 1$ one gets $\bar{\mu}=\mu_{min}+\bar{t}-\hat{t}$ and $\bar{s}=\bar{t}-\hat{t}$, i.e., $\hat{t}=\bar{t}-(\bar{\mu}-\mu_{min})$ and $\bar{s}=\bar{\mu}-\mu_{min}$.

Furthermore, one has $h(\bar{t},\bar{\mu})=u(\bar{s})=d\int_0^{\bar{\mu}-\mu_{min}} \emptyset(\mu_{min}+\sigma)a_1(\sigma+\bar{t}-(\bar{\mu}-\mu_{min}))d\sigma$ $=d\int_{-(\bar{\mu}-\mu_{min})}^0 \emptyset(\bar{\mu}+\sigma)a_1(\bar{t}+\sigma)d\sigma$ Anemia of Renal Disease Anemia affects almost all patients with chronic kidney disease (CKD). It is caused by failure of renal excretory and endocrine function. It often develops once renal function decreases to 50% and the degree of anemia increases with severity of renal failure. See Strippoli, et. al. Anemia develops because of a deficiency in endogenous erythropoietin production by the kidneys, increased blood losses, functional or absolute iron deficiency and decreased red cell survival. See J. B. Wish, Clinical Journal of the American Society of Nephrology, 1:S4-S8, 2006. Concerning endogenous erythropoietin production by the kidneys, one has to note that kidneys of end-stage renal disease patients can still produce some EPO, and thus can maintain higher hemoglobin levels than those found in anephric patients. Reasons for blood losses can be purpura, gastrointestinal and gynecologic bleeding (which occur in one third to one half of all CKD patients), frequent blood sampling, blood left in the extracorporeal circuit, multiple vascular surgeries, etc. Furthermore, neocytolysis contributes to renal anemia and it explains the often demonstrable hemolytic component and the worsening of hemolysis with more pronounced renal disease. A description of neocytolysis is provided above. It further explains the responsiveness of hemolysis to ESA therapy and the increased efficiency of subcutaneous (s.c.) compared to intravenous therapy (i.v.), because in s.c. administration nadirs in EPO levels which precipitate neocytolysis are avoided. See Rice 1999. In general, renal anemia is normocytic and normochromic and the number of reticulocytes is normal or slightly decreased, which is inappropriate in the context of a reduced RBC population. Certain deficiency states, especially iron, but also folate or vitamin B.sub.12 deficiency may alter the nature of the anemia. See Finch 1982; M. Polenakovic and A. Sikole, Journal of American Society of Nephrology, 7:1178-1182, 1996.

Untreated anemia is associated with decreased oxygen delivery to the tissues. For compensatory reasons, cardiac output increases, resulting in left ventricular hypertrophy. Cardiac disease is the most common cause of death among patients who are on maintenance dialysis. Partial correction of anemia in these patients was shown to reduce cardiac ischemia and ameliorate cardiomegaly, thus reducing cardiac related morbidity. See A. Besarab, W. K. Bolton, J. K. Browne, J. C. Egrie, A. R. Nissenson, D. M. Okamoto, S. J. Schwab, and D. A. Goodkin, The New England Journal of Medicine, 339:584-590, 1998. Further consequences of uncorrected anemia are decreased cognition and mental acuity and overall decrease in patient welfare.

ESA Therapy

Erythropoiesis stimulating agents have been used to treat anemia in patients suffering from chronic renal failure for more than two decades. Optimal hemoglobin targets are still a matter of discussion. Studies have shown (see e.g. Singh et al.; Strippoli et al., R. N. Foley, B. M. Curtis, and P. S. Parfrey. Clinical Journal of the American Society of Nephrology, 4:726-733, 2009 (hereinafter "Foley et al.") that a partial correction of anemia is preferable to a full correction. A number of complications can occur in patients with CKD when they have near-normal/normal hemoglobin levels, i.e., higher vascular access thrombosis, hypertension and greater requirements for antihypertensives, cardiovascular events, earlier need for renal replacement therapy and higher mortality. Normal hemoglobin levels for women are in a range of between about 12 g/dl and 16 g/dl, and in a range of between about 13 g/dl and about 17.5 g/dl for men.

Defining an optimal hemoglobin target is not the only issue regarding ESA therapy. Another problem is: how can the target hemoglobin be achieved and how to keep the patient near this hemoglobin level over a long time period? The dose and frequency of administration of an ESA treatment regimen are most often determined based on the prior experience of the physician and on established guidelines. This approach bears some limitations and level of hemoglobin tends to fluctuate greatly and cycling phenomena are observed. An analysis of 31,267 patients on hemodialysis in the Fresenius Medical Care-North America database found that only 5% of patients persistently remained within a desired Hb range of 11-12 g/dl for a period of 6 months. See A. J. Collins, R. M. Brenner, J. J. Ofman, E. M. Chi, N. Stuccio-White, M. Krishnan, C. Solid, N. J. Ofsthun, and J. M. Lazarus. American Journal of Kidney Diseases, 46:481-488, 2005 (hereinafter "Collins et al."). Fishbane et al. analyzed data of dialysis patients collected over five years in a hospital and came to a similar conclusion. See S. Fishbane and J. S. Berns. Kidney International, 68:1337-1343, 2005 (hereinafter "Fishbane et al."). More than 90% of the patients experienced hemoglobin cycling. The authors state that changes in ESA dose were the most important driver and were associated with hemoglobin excursion in about 80% of cases. The ESA dose adjustment protocol that was used was similar to the protocol used in most dialysis centers.

Therapy with ESAs is quite different than biological erythropoietin secretion. In hemodialysis patients, i.v. administration route is primarily used, because of the availability of venous access. Intravenous treatment involves short, intermittent, non-physiologic bursts of EPO concentration. The bursts are followed by a fast decline to very low levels of EPO. These fluctuations in plasma concentration do not coincide, either temporally or in magnitude, with physiologic perturbations. Therefore, it may not be surprising that Hb levels fluctuate widely and that it is extremely difficult for physicians to adjust dosing schemes such that no cycling phenomena occur. Note that fluctuations in hemoglobin result in varying oxygen delivery to vital organs. Consequences include repeated episodes of relative ischemia and compensatory mechanisms in organs (e.g., heart) that may result in disordered growth signals, pathologic organ function and worsened patient outcomes. (See Fishbane et al.).

A predictive model of erythropoiesis can help deal with this situation. For instance, a physician can try different ESA treatment regimens and observe their effects on hemoglobin levels over the next few months. Dosing regimens can be tested/chosen with regard to avoidance of neocytolysis, minimal amounts of ESA administered and avoidance of cycling patterns in Hb concentration.

Iron Therapy

Patients with anemia of chronic kidney disease have to be followed for symptoms of iron deficiency. See J. W. Fisher. Experimental Biology and Medicine, 28:1-24, 2003. 80-90% of dialysis patients on ESA therapy will require iron at some stage. See R. M. Schaefer and L. Schaefer. Nephrology Dialysis Transplantation, 13:9-12, 1998. This very pronounced need for supplementary iron has different reasons. On one hand iron stores can be depleted (absolute iron deficiency). Iron loss in hemodialysis patients (due to continuous gastrointestinal, purpural and gynecological bleeding, frequent blood sampling, surgeries, . . . ) is about 1500-3000 mg/year, as compared to iron loss for a healthy adult that is about 400-800 mg/year, and can be even higher under certain circumstances. Hence, the daily need for iron can be well above the absorptive capacity of the intestinal. This is aggravated by the fact that the uptake via the duodenum is often impaired in these patients. On the other hand, a functional iron deficiency is often observed in renal anemia. During ESA therapy, the number of erythroid progenitor and precursor cells in the bone marrow increase drastically and this imposes a lot of stress on systemic iron homeostasis. Supply and demand often do not match. It is difficult, even for healthy persons, to increase the rate at which iron is released from stores and is recycled from hemoglobin to deliver enough iron to the bone marrow to keep up with supraphysiologic rates of RBC production during ESA treatment. Matters are further complicated in chronic kidney disease because of inflammation, which frequently occurs with various degrees of severity. Thus, iron utilization is regularly decreased in renal insufficiency. See above for a detailed description of the effects of inflammation on systemic iron homeostasis.

In the pre-ESA era iron overload, because of excessive blood transfusions, was a major cause of morbidity in dialysis patients. Its significance in the post-EPO era remains unclear. See K. Kalantar-Zadeh, D. L. Regidor, C. J. McAllister, B. Michael, and Warnock D. G., Journal of American Society of Nephrology, 16:3070-3080, 2005. A continuous administration of i.v. iron certainly results in overfilled iron-stores and imposes serious health risks. Hence, decisions on when to supply the patient with i.v. iron and when to withdraw therapy have to be thoroughly evaluated. A mathematical model can help keep track of the current iron status of a patient and can help to make decisions on adaptations of treatment.

Finally, there is a very complex interaction between hemoglobin cycling and iron storage whose dynamical behavior under ESA and iron treatment, even for an experienced physician, is barely predictable. In Alfrey et al., the authors suggest that: "[ . . . ] the current therapeutic paradigm of hemoglobin monitoring, iron treatment, and rHuEPO treatment results in recurrent nonphysiologic cycling of hemoglobin levels in hemodialysis patients."

Computation of Hematocrit and Hemoglobin Concentrations

In order to compute the hematocrit (HCT) and the hemoglobin concentration (Hb) for a subject from the model output (which is the number of red blood cells circulating in blood), estimates of the total blood volume of the subject are needed. The Nadler and Allen formula (see Nadler, S. B., Hidalgo, J. U., and Bloch, T., Surgery, 1962, Vol. 51, pp. 224-232) can be used to estimate the total blood volume (TBV) of a healthy subject according to her/his weight and height:

Women: TBV [ml]=183.3+356.1.times.(height [m])$^3$+33.08.times.weight [kg],

Men: TBV [ml]=604.1+366.9.times. (height [m])$^3$+32.19.times.weight [kg].

The TBV for a dialysis patient can be measured by radio-labeling red blood cells with chromium-51 as described above. Using these estimates for the total blood volume, the hematocrit (HCT) and the hemoglobin concentration (Hb) can be computed for a patient from the number of red blood cells circulating in blood via the following formulae:

$$HCT\ [\%] = \frac{(M(t) \times MCV[\text{fl}])}{TBV\ [\text{ml}]}$$

where $M(t)=\int_0^{\mu_{max}^m} m(t, \mu^m) d\mu^m$ is the total number of erythrocytes circulating in blood and MCV is the mean corpuscular volume of a RBC which is obtained from measurement, a $$Hb\left[\frac{g}{l}\right] = 1000 \times \frac{(M(t) \times MCV[pg])}{TBV\ [\text{ml}]}$$

where MCH is the mean cellular hemoglobin, which is also obtained via measurements.

Implementation in a Computer Network

Figure 14:
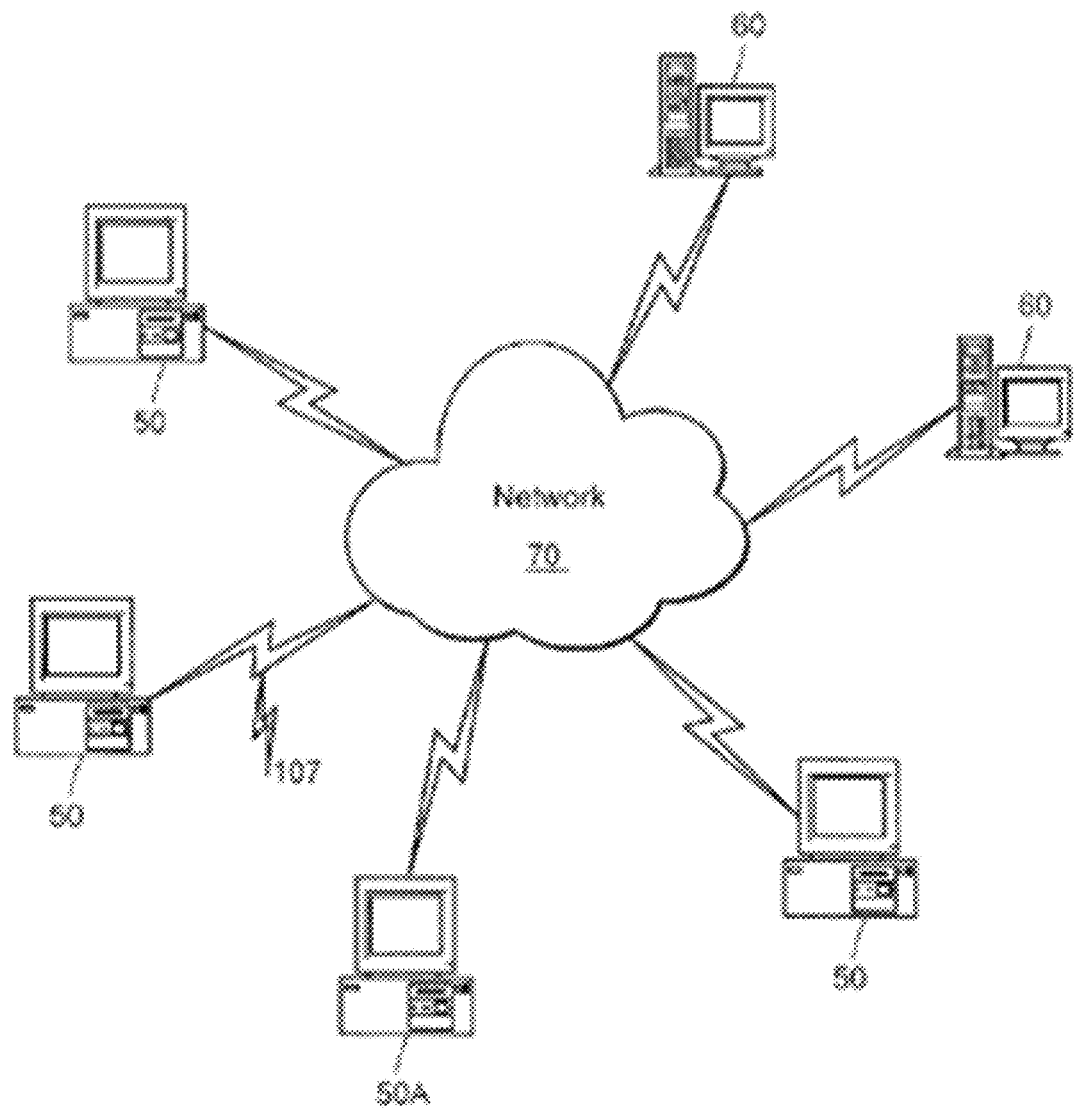
FIG. 14 is a schematic view of a computer network in which some embodiments of the present invention can be implemented.

FIG. 14 illustrates a computer network or similar digital processing environment in which the present invention can be implemented.

Computer(s)/devices 50 and server computer(s) 60 provide processing, storage, and input/output devices executing application programs and the like. Computer(s)/devices 50 can also be linked through communications network 70 to other computing devices, including other devices/processes 50, digital processor dialysis machines 50A, including machines with integrated modular drug delivery devices, and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 15:
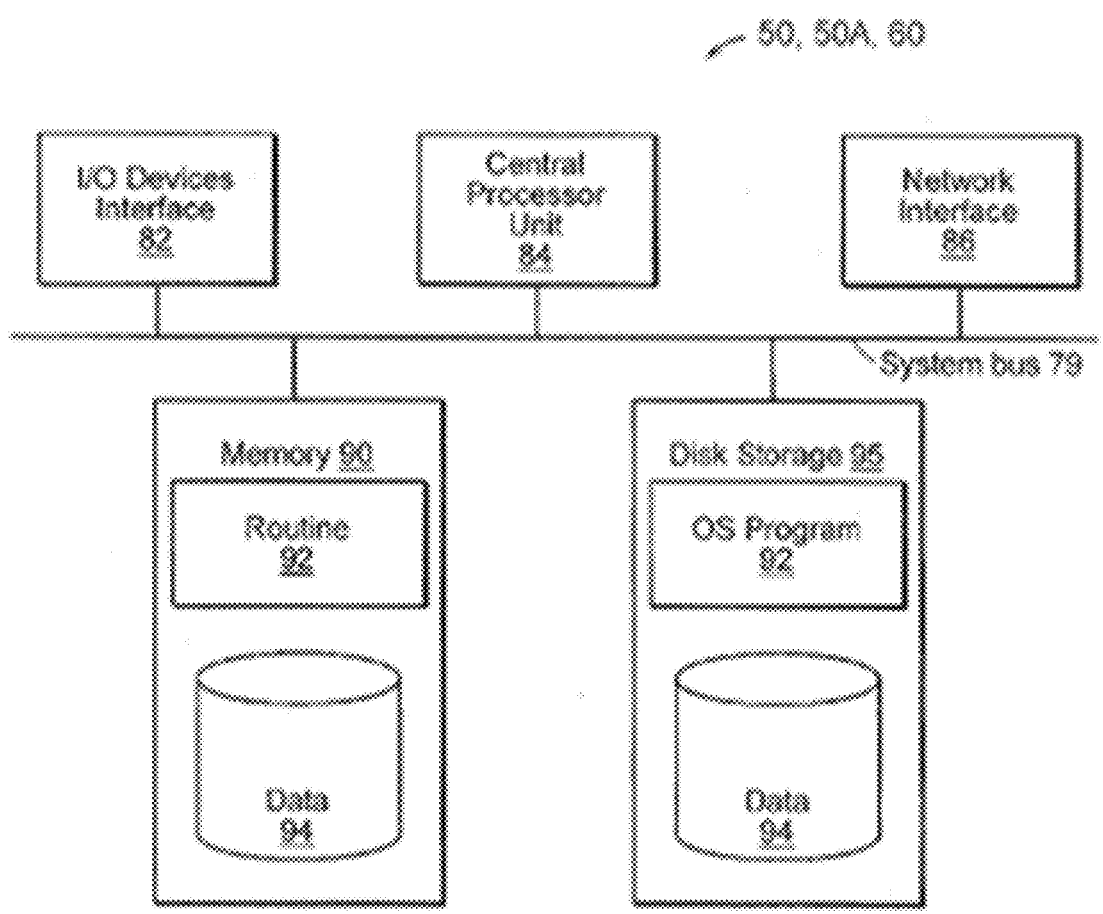
FIG. 15 is a block diagram of a computer of the network of FIG. 14.

FIG. 15 is a diagram of the internal structure of a computer (e.g., processor/device 50, digital processor dialysis machines 50A, or server computers 60) in the computer system of FIG. 14. Each computer 50, 50A, 60 contains a system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements which could be data collected during a treatment, but also instructions to a machine with integrated modular drug delivery devices to follow a drug delivery scheme provided by a central erythropoiesis modeling engine. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 14). Memory 90 provides volatile storage for computer software instructions 92 and data 94 used to implement an embodiment of the present invention (e.g., Eqs. described above and listed in Section 4 or any other erythropoiesis modeling engine detailed above). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the system. Computer program product 92 can be installed by any suitable software installation procedure, as is well known in the art. In another embodiment, at least a portion of the software instructions can also be downloaded over a cable, communication and/or wireless connection. In other embodiments, the programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 can receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

The relevant teachings of all patents, published patent applications and literature references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

The meanings of method steps of the invention(s) described herein are intended to include any suitable method or manner of causing one or more other parties or entities to perform the recited steps, consistent with the patentability of the following claims, unless a different meaning is expressly provided or otherwise clear from the context. Such parties or entities need not be under the direction or control of any other party or entity, and need not be located within a particular jurisdiction.

Thus for example, a description or recitation of "adding a first number to a second number" is meant to include causing one or more parties or entities to add the two numbers together. For example, if person X engages in an arm's length transaction with person Y to add the two numbers, and person Y indeed adds the two numbers, then both persons X and Y perform the step as recited: person Y by virtue of the fact that he actually added the numbers, and person X by virtue of the fact that he caused person Y to add the numbers. Furthermore, if person X is located within the United States and person Y is located outside the United States, then the method is performed in the United States by virtue of person X's participation in causing the step to be performed.

What is claimed is:

1. A method for determining efficacy of a therapy, comprising:
   a) generating in silico a plurality of virtual patients for modeling a health condition based on data collected from a population of previously treated patients;
      wherein the collected data represents at least one measured biological response of said previously treated patients to a previously administered therapeutic regimen, and wherein each virtual patient comprises at least one mathematical model representing a physiological system and exhibiting a one-to-one correspondence with one of the population of previously treated patients, wherein the at least one mathematical model for each virtual patient is fitted to data of the corresponding previously treated patient;
   b) applying a simulated therapy to said virtual patients over a simulated period of time;
   c) determining one or more physiological parameters in said virtual patients in response to said simulated therapy over the simulated period of time;
   d) applying at least one adjusted simulated therapy to said virtual patients over the same simulated period of time based on said determined one or more physiological parameters of said virtual patients;
   e) determining one or more physiological parameters in said virtual patients in response to said at least one adjusted simulated therapy over the same simulated period of time;
   f) determining an optimal simulated therapy from among the simulated therapy and the at least one adjusted simulated therapy, wherein determining the optimal simulated therapy comprises repeating steps d)-e) until the one or more determined physiological parameters in said virtual patients are within a desired range; and
   g) recommending the optimal simulated therapy to a plurality of actual patients.

2. The method of claim 1, further comprising determining whether at least one of said determined physiological parameters of at least one of said virtual patients is indicative of an adverse effect from said simulated therapy.

3. The method of claim 1, wherein the simulated therapy includes a simulated non-compliance with a prescribed therapy.

4. The method of claim 1, wherein the determining step further comprises determining values of said one or more physiological parameters at a plurality of times over a predetermined time interval.

5. The method of claim 4, wherein the one or more physiological parameters comprises one or more metabolic parameters.

6. The method of claim 5, wherein the one or more metabolic parameters comprise blood parameters and/or urine parameters.

7. The method of claim 6, wherein the blood parameters comprise any of hemoglobin concentration and hematocrit level.

8. The method of claim 1, wherein the at least one model is an erythropoiesis model.

9. The method of claim 1, further comprising applying a plurality of different simulated therapies to each of said virtual patients, determining one or more physiological parameters in said virtual patients in response to each simulated therapy, and evaluating each simulated therapy based on the corresponding physiological parameters.

10. The method of claim 1, wherein the therapy comprises any of at least one of: a pharmacological therapy, a non-pharmacological therapy, and a combination thereof.

11. The method of claim 10, wherein the at least one pharmacological therapy comprises an anemia therapy.

12. The method of claim 11, wherein the anemia therapy comprises administering at least one of an erythropoiesis stimulating agent (ESA), iron, a drug stimulating endogenous erythropoietin release and/or synthesis, a biosimilar, or a combination thereof.

13. The method of claim 12, wherein the erythropoiesis stimulating agent comprises exogenous erythropoietin.

14. The method of claim 10, wherein the one or more non-pharmacological therapies comprises a fluid therapy, a dietary therapy, an exercise therapy, an extracorporeal therapy, a radiotherapy, a therapy using sound and/or ultrasound, an electrotherapy, or a combination thereof.

15. The method of claim 1, wherein the data collected from the population of previously treated patients comprises gender, age, weight, height, ethnicity, metabolic/chemistry parameters, complete blood count, or a combination thereof.

16. The method of claim 15, wherein the data collected further comprises medications used by the previously treated patients, past medical history data, past surgical history data or a combination thereof.

17. The method of claim 16, wherein the past medical history data comprises information regarding diabetes, blood pressure/hypertension, cancer, congestive heart failure, or a combination thereof.

18. A method for performing a clinical trial, in silico, for a health condition comprising:
   a) generating in silico one or more virtual patients, wherein the one or more virtual patients are based on data collected from a population of previously treated patients suffering from said health condition and wherein each virtual patient comprises at least one mathematical model representing a physiological system and exhibiting a one-to-one correspondence with one of the population of previously treated patients, wherein the at least one mathematical model for each virtual patient is fitted to data of the corresponding previously treated patient;
   b) applying a simulated therapy to each of the one or more virtual patients, wherein each of the one or more virtual patients exhibits an initial value for one or more physiological parameters when the simulated therapy is initially applied thereto;
   c) determining whether said one or more physiological parameters in each of said one or more virtual patients is maintained within a desired range in response to said simulated therapy;
   d) performing iteratively the following steps so as to determine an optimal therapy for application to a plurality of actual patients exhibiting said health condition:
      i. modifying one or more parameters of said simulated therapy to create a modified simulated therapy;
      ii. administering said modified simulated therapy to each of the one or more virtual patients, wherein each of said one or more virtual patients respectively exhibits said initial value for said one or more physiological parameters corresponding to that virtual patient when the modified simulated therapy is initially applied thereto; and
      iii. determining whether said one or more physiological parameters in said one or more virtual patients is maintained within said desired range in response to said modified simulated therapy; and
   e) recommending the optimal therapy for application to the plurality of actual patients.

19. The method of claim 18, further comprising determining whether at least one of said determined physiological parameters of at least one of said virtual patients is indicative of an adverse effect from said simulated therapy.

20. The method of claim 18, wherein the simulated therapy includes a simulated non-compliance with a prescribed therapy.

21. The method of claim 18, wherein the determining step further comprises determining values of said one or more physiological parameters at a plurality of times over a predetermined time interval.

22. The method of claim 21, wherein the one or more physiological parameters comprises one or more metabolic parameters.

23. The method of claim 22, wherein the one or more metabolic parameters comprise blood parameters and/or urine parameters.

24. The method of claim 23, wherein the blood parameters comprise any of hemoglobin concentration and hematocrit level.

25. The method of claim 18, wherein the at least one model is an erythropoiesis model.

26. The method of claim 18, further comprising applying a plurality of different simulated therapies to each of said virtual patients, determining one or more physiological parameters in said virtual patients in response to each simulated therapy, and evaluating each simulated therapy based on the corresponding physiological parameters.

27. The method of claim 18, wherein the simulated therapy comprises any of at least one pharmacological therapy, at least one non-pharmacological therapy, and combinations thereof.

28. The method of claim 27, wherein the one or more pharmacological therapies comprises exogenous erythropoietin.

29. A computer system for determining an efficacy of a therapy comprising:
a processor configured to:
generate in silico a plurality of virtual patients for modeling a health condition based on data collected from a population of previously treated patients suffering from said health condition;
wherein the collected data represents at least one measured biological response of said previously treated patients to a previously administered therapeutic regimen,
wherein each virtual patient comprises at least one mathematical model of erythropoiesis that exhibits a one-to-one correspondence with one of the population of previously treated patients, wherein the at least one mathematical model for each virtual patient is fitted to data of the corresponding previously treated patient;
apply a simulated therapy to said virtual patients over a simulated period of time;
determine one or more physiological parameters of said virtual patients in response to said simulated therapy over the simulated period of time;
determine an optimal simulated therapy from among the simulated therapy and at least one adjusted simulated therapy by iteratively performing the following steps until the one or more determined physiological parameters in said virtual patients are within a desired range:
apply at least one adjusted simulated therapy to said virtual patients over the same simulated period of time based on said determined one or more physiological parameters of said virtual patients; and
determine one or more physiological parameters of said virtual patients in response to said at least one adjusted simulated therapy over the same simulated period of time; and
recommend the optimal simulated therapy for application to a plurality of actual patients.

30. The computer system of claim 29, wherein said one or more physiological parameters of at least one of said virtual patients is indicative of an adverse effect from said simulated therapy.

31. The computer system of claim 29, wherein the processor is further configured to determine values of said one or more physiological parameters at a plurality of times over a predetermined time interval.

32. The computer system of claim 29, wherein the one or more physiological parameters comprises one or more metabolic parameters.

33. The computer system of claim 32, wherein the one or more metabolic parameters comprises blood parameters and/or urine parameters.

34. The computer system of claim 33, wherein the blood parameters comprise any of hemoglobin concentration and hematocrit level.

35. The computer system of claim 29, wherein the erythropoiesis model comprises $$\frac{\partial}{\partial t} p(t, \mu^p) + \frac{\partial}{\partial \mu^p} p(t, \mu^p) = \beta^p p(t, \mu^p),$$

$$\frac{\partial}{\partial t} q(t, \mu^q) + \frac{\partial}{\partial \mu^q} q(t, \mu^q) = (\beta^q - \alpha^q(E(t))) q(t, \mu^q),$$

$$\frac{\partial}{\partial t} r(t, \mu^r) + \frac{\partial}{\partial \mu^r} r(t, \mu^r) = \beta^r r(t, \mu^r),$$

$$\frac{\partial}{\partial t} s(t, \mu^s) + v^s(E(t)) \frac{\partial}{\partial \mu^s} s(t, \mu^s) = -\alpha^s s(t, \mu^s),$$

$$\frac{\partial}{\partial t} m(t, \mu^m) + \frac{\partial}{\partial \mu^m} m(t, \mu^m) = -\alpha^m(E(t), \mu^m) m(t, \mu^m),$$

$$\frac{d}{dt} E^{end}(t) = \frac{1}{TBV} E_{in}^{end}(t) - c_{dog}^{end} E^{end}(t),$$

$$\frac{d}{dt} E^{ex}(t) = \frac{1}{TBV} E_{in}^{ex}(t) - c_{dog}^{ex} E^{ex}(t),$$

where $$\alpha^q(E(t)) = \frac{a_1 - b_1}{1 + e^{k_1 E(t) - \kappa_1}} + b_1,$$

$$v^s(E(t)) = \frac{a_2 - b_2}{1 + e^{-k_2 E(t) + c_2}} + b_2.$$

and $$\alpha^m(E(t), \mu^m) = \begin{cases} \gamma^m(\mu^m) + \min\left(\frac{c_E}{E(t)^{k_E}}, b_E\right), & \text{for } E(t) < \tau_E, \mu_{min}^{m,n} \leq \mu^m \leq \mu_{max}^{m,n}, \\ \gamma^m(\mu^m), & \text{otherwise,} \end{cases}$$

with $$\gamma^m(\mu^m) = \begin{cases} \alpha_{rand}^m & \text{for } \mu^m \in [\mu_{min}^m, \mu_{max}^m - \delta], \\ \frac{3\alpha_{rand}^m \delta^2}{(\mu^m)^2 - 2(\mu_{max}^m + \delta)\mu^m + (\mu_{max}^m + 2\delta)\mu_{max}^m} & \text{for } \mu^m \in [\mu_{max}^m - \delta, \mu_{max}^m), \\ \infty & \text{for } \mu^m \geq \mu_{max}^m. \end{cases}$$

-continued and $$\frac{d}{dt}a_1(t) = k_{41}(H(t))a_4(t) + a_{fv,total}(t)\delta_{t_0}(t) + k_{gastro,t}(H(t))a_{gastro}(t) +$$
$$k_{31}(H(t))a_5(t) - k_{15}a_1(t) -$$
$$d_1\left(\int_{\mu_{min}^r}^{\mu_{max}^r} \varphi(\mu^r)r(t,\mu^r)d\mu^r + \int_{\mu_{min}^s}^{\mu_{max}^s} \varphi(\mu^s)s(t,\mu^s)d\mu^s\right)a_1(t),$$

$$a_2(t) = \int_{\mu_{min}^r}^{\mu_{max}^r} \alpha(h,\mu^r)r(t,\mu^r)d\mu^r +$$
$$\int_{\mu_{min}^s}^{\eta_{max}^s(t)} \alpha(h,\eta^s)h(t,\eta^s)s\left(t,\mu_{min} + \int_{t-\eta^s}^{t} v(E(s))ds\right)d\eta^s$$

$$a_3(t) = \int_{\mu_{min}^m}^{\mu_{max}^m} h(t-\mu^m, \eta_{max}^s)m(t,\mu^m)d\mu^m$$

$$\frac{d}{dt}a_4(t) = \int_{\mu_{min}^r}^{\mu_{max}^r} \alpha(h,\mu^r)h(t,\mu^r)r(t,\mu^r)d\mu^r +$$
$$\int_{\eta_{min}^s}^{\eta_{max}^s(t)} \alpha(h,\eta^s)h(t,\eta^s)s\left(t,\mu_{min} + \int_{t-\eta^s}^{t} v(E(s))ds\right)d\eta^s +$$
$$\int_{\mu_{min}^m}^{\mu_{max}^m} h(t-\mu^m, \eta_{max}^s)\alpha^m(E(t),\mu^m)m(t,\mu^m)d\mu^m -$$
$$k_{41}(H(t))a_4(t) - k_{45}a_4(t),$$

$$\frac{d}{dt}a_5(t) = k_{15}a_1(t) + k_{45}a_4(t) - k_{51}(H(t))a_5(t),$$

$$\frac{d}{dt}H(t) = \frac{1}{TBV}H_{good}(t) - c_{deg}^H H(t).$$

36. The computer system of claim 29, wherein the therapy comprises any of at least one pharmacological therapy, at least one non-pharmacological therapies, and a combination thereof.

37. The computer system of claim 36, wherein the at least one pharmacological therapy comprises an anemia therapy.

38. The computer system of claim 37, wherein the anemia therapy comprises administering at least one of an erythropoiesis stimulating agent (ESA), iron, a drug stimulating endogenous erythropoietin release and/or synthesis, a biosimilar, or a combination thereof.

39. The computer system of claim 38, wherein the erythropoiesis stimulating agent comprises exogenous erythropoietin.

40. The computer system of claim 36, wherein the one or more non-pharmacological therapies comprises a fluid therapy, a dietary therapy, an exercise therapy, an extracorporeal therapy, a radiotherapy, a therapy using sound and/or ultrasound, an electrotherapy, or a combination thereof.

41. The computer system of claim 29, wherein the data collected from the population of previously treated patients comprises gender, age, weight, height, ethnicity, metabolic/chemistry parameters, and/or complete blood count.

42. The computer system of claim 41, wherein the data collected further comprises medications used by the previously treated patients, past medical history data, and past surgical history data.

43. The computer system of claim 42, wherein the past medical history data comprises information regarding diabetes, blood pressure/hypertension, cancer, congestive heart failure, or a combination thereof.

\* \* \* \* \*